United States Patent
Carabe-Fernandez et al.

(10) Patent No.: US 11,701,526 B2
(45) Date of Patent: Jul. 18, 2023

(54) DETERMINING QUANTITIES OF INTEREST FOR PARTICLE THERAPY

(71) Applicant: The Trustees of the University of Pennsylvania, Philadelphia, PA (US)

(72) Inventors: Alejandro Carabe-Fernandez, Philadelphia, PA (US); Alejandro Bertolet Reina, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 481 days.

(21) Appl. No.: 16/818,683

(22) Filed: Mar. 13, 2020

(65) Prior Publication Data

US 2021/0283426 A1    Sep. 16, 2021

(51) Int. Cl.
*A61N 5/10* (2006.01)
*G16H 20/40* (2018.01)
*G16H 50/50* (2018.01)

(52) U.S. Cl.
CPC ......... *A61N 5/1071* (2013.01); *A61N 5/1031* (2013.01); *G16H 20/40* (2018.01); *G16H 50/50* (2018.01); *A61N 2005/1034* (2013.01); *A61N 2005/1087* (2013.01)

(58) Field of Classification Search
CPC .. A61N 5/1065; A61N 5/1077; A61N 5/1043; A61N 5/1031
See application file for complete search history.

(56) References Cited

PUBLICATIONS

"A Kernel-based algorithm for spectral fluence of clinical proton beams to calculate dose-average LET and other dosimetric quantities of interest", A. Bertolet, Mar. 2, 2020 (Year: 2020).*
Agostinelli et al., "Geant4-a simulation toolkit," Nucl. Instruments Methods Phys Res. Sect A Accel Spectrometers, Detect Assoc Equip., vol. 506, No. 3, 2003, pp. 250-303.
Allison et al., "Geant4 developments and applications," IEEE Trans. Nucl. Sci., vol. 53, No. 1, 2006, pp. 270-278.
Allison et al., "Recent developments in Geant4," Nucl. Instruments Methods Phys Res. Sect A Accel Spectrometers, Detect Assoc. Equip., vol. 835, 2016, pp. 186-225.
An et al., "Robust intensity-modulated proton therapy to reduce high linear energy transfer in organs at risk," Med. Phys., vol. 44, No. 12, 2017, pp. 6138-6147.
Barendsen GW, "The relationships between RBE and LET for different types of lethal damage in mammalian cells biophysical and molecular mechanisms," Radiat Res., vol. 139, 1994, pp. 257-270.

(Continued)

*Primary Examiner* — Don K Wong
(74) *Attorney, Agent, or Firm* — BakerHostetler

(57) ABSTRACT

Methods and systems are described for determining quantities of interest for particle therapy. An example method can comprise determining one or more first functions indicative of spectral fluence associated with a particle therapy. The one or more first functions can be based on a plurality of simulations of a particle beam. The method can comprise determining, based on the one or more first functions and a second function associated with calculating a quantity, data indicative of the quantity. The method can comprise causing output of the data indicative of the quantity.

20 Claims, 22 Drawing Sheets
(13 of 22 Drawing Sheet(s) Filed in Color)

(56) References Cited

PUBLICATIONS

Belli et al., "RBE-LET relationships for cell inactivation and mutation induced by low energy protons in V79 cells: further results at the LNL facility," Int. J. Radiat. Biol. Vol. 74, 1998, pp. 501-509.

Bellinzona et al., "On the parametrization of lateral dose profiles in proton radiation therapy," Phys. Medica., vol. 31, 2015, pp. 484-492.

Berger et al., "Stopping-Power; Range Tables for Electrons, Protons, and Helium Ions," NIST. NIST Standard Reference Database 124, https://www.nist.gov/pml/stopping-power-range-tables-electrons-protons-and-helium-ions. Published 2017, Accessed Dec. 19, 2018.

Bernal et al., "Track structure modeling in liquid water: a review of the Geant4-DNA very low energy extension of the Geant4 Monte Carlo simulation toolkit," Phys. Medica., vol. 31, 2015, pp. 861-874.

Bertolet et al., "A kernel-based algorithm for the spectral fluence of clinical proton beams to calculate dose-averaged LET and other dosimetric quantities of interest," Med. Phys. [ACCEPTED], 2020.

Bertolet et al., "Calculation of clinical dose distributions in proton therapy from microdosimetry," Med. Phys., vol. 46, 12, 2019, pp. 5816-5823.

Bertolet et al., "Dose-averaged LET calculation for proton track segments using microdosimetric Monte Carlo simulations," Med. Phys., vol. 46, No. 9, 2019, pp. 4184-4192.

Bertolet et al., "Segment-averaged LET concept and analytical calculation from microdosimetric quantities in proton radiation therapy," Med. Phys., vol. 46, 9, 2019, pp. 4204-4214.

Bue'e et al., "Tau protein isoforms, phosphorylation and role in neurodegenerative disorders," Brain Research Reviews 33 (2000) 95-130.

Cao et al., "Linear energy transfer incorporated intensity modulated proton therapy optimization," Phys. Med. Biol., vol. 63, 2018, 015013, 10 pages.

Cortés-Giraldo et al., "A critical study of different Monte Carlo scoring methods of dose average linear-energy-transfer maps calculated in voxelized geometries irradiated with clinical proton beams," Phys. Med. BioL, vol. 60, No. 7, 2015, pp. 2645-2669.

Crowley et al., "Niementowski-type synthesis of pyrido[3,2-e][1,2,4]triazines: potent aza-analogs of pyrido[2,3-b]pyrazine fungicides," Tetrahedron Letters 51 (2010) 2652-2654.

Deng et al., "Hybrid 3D analytical linear energy transfer calculation algorithm based on precalculated data from Monte Carlo simulations," Med. Phys., 2019, doi:10.1002/mp.13934.

Fager et al., "Linear Energy Transfer Painting With Proton Therapy: A Means of Reducing Radiation Doses With Equivalent Clinical Effectiveness," Int. J. Radiat. Oncol., vol. 91, No. 5, 2015, pp. 1057-1064.

Giantsoudi et al., "Linear energy transfer-guided optimization in intensity modulated proton therapy: Feasibility study and clinical potential," Int. J. Radiat. Oncol. Biol. Phys., vol. 87, No. 1, 2013, pp. 216-222.

Grassberger et al., "Elevated LET components in clinical proton beams," Phys. Med. Biol., vol. 56, No. 20, 2011, pp. 6677-6691.

Grassberger et al., "Variations in linear energy transfer within clinical proton therapy fields and the potential for biological treatment planning," Int. J Radiat Oncol. Biol. Phys., vol. 80, 5, 2011, No. 1559-1566.

Guan et al., "RBE model-based biological dose optimization for proton radiobiology studies," Int. J. Part. Ther., vol. 5, No. 1, 2019, pp. 160-171.

Hawkins et al., "A Microdosimetric-Kinetic Model for the Effect of Non-Poisson Distribution of Lethal Lesions on the Variation of RBE with LET," Radiat Res., vol. 160, 1, 2003, pp. 61-69.

Hawkins RB, "A microdosimetric-kinetic model of cell death from exposure to ionizing radiation of any LET, with experimental and clinical applications," Int. J Radiat Biol., vol. 69, 6, 1996, pp. 739-755.

Hirayama et al., "An analytical dose-averaged LET calculation algorithm considering the off-axis LET enhancement by secondary protons for spot-scanning proton therapy," Med. Phys., vol. 45, 7, 2018, pp. 3404-3416.

Hong et al., "A pencil beam algorithm for proton dose calculations," Phys. Med. Biol., vol. 41, 1996, pp. 1305-1330.

Huang et al., "Validation and clinical implementation of an accurate Monte Carlo code for pencil beam scanning proton therapy," J. Appl. Clin. Med. Phys., vol. 19, No. 5, 2018, pp. 558-572.

Inaniwa et al., "Adaptation of stochastic microdosimetric kinetic model for charged-particle therapy treatment planning," Phys. Med. Biol., vol. 63, No. 9, 2018, pp. 0-17.

Inaniwa et al., "Treatment planning of intensity modulated composite particle therapy with dose and linear energy transfer optimization," Phys. Med. Biol., vol. 62, No. 12, 2017, pp. 5180-5197.

Incerti et al., "Comparison of GEANT4 very low energy cross section models with experimental data in water," Med. Phys., vol. 37, 2010, pp. 4692-4708.

Incerti et al., "Geant4-DNA example applications for track structure simulations in liquid water: a report from the Geant4-DNA Project," Med. Phys., vol. 45, 2018, pp. e722-e739.

Incerti et al., "The Geant4-DNA project," Int. J. Model Simul Sci. Comput., vol. 1, 2010, pp. 157-178.

Kase et al., "Biophysical calculation of cell survival probabilities using amorphous track structure models for heavy-ion irradiation," Phys. Med. Biol., vol. 53, No. 1, 2008, pp. 37-59.

Kase et al., "Microdosimetric calculation of relative biological effectiveness for design of therapeutic proton beams," J. Radiat Res., vol. 54, No. 3, 2013, pp. 485-493.

Kase et al., "Microdosimetric Measurements and Estimation of Human Cell Survival for Heavy-Ion Beams," Radiat Res., vol. 166, No. 4, 2006, pp. 629-638.

Kellerer AM, "Analysis of patterns of energy deposition," In: Ebert HG, ed. Second Symposium on Microdosimetry, Stresa, Italy: Commission of the European Communities; 1970, pp. 107-136.

Kellerer AM, "Fundamentals of microdosimetry," In: Kase KR, Bjarngard BE, Attix FH, eds. The Dosimetry of Ionization Radiation, vol. I, Cambridge: Academic Press Inc; 1985, pp. 77-162.

Kellerer et al., "Concepts of microdosimetry—I. Quantities," Radiat Environ Biophys., vol. 12, 1975, pp. 61-69.

Kellerer et al., "Concepts of microdosimetry—II. Probability distributions of the microdosimetry variables," Radiat Environ. Biophys., vol. 12, 1975, pp. 205-216.

Kellerer et al., "Concepts of microdosimetry—III. Mean values of the microdosimetric distributions," Radiat Environ. Biophys., vol. 12, 1975, pp. 321-335.

Kellerer et al., "The theory of dual radiation action. In: Ebert M, Howard A, eds. Current Topics in Radiation Research," vol. VIII, Manchester, UK: American Elsevier Publishing Company; 1974, pp. 85-156.

Kimstrand et al., "A beam source model for scanned proton beams," Phys. Med. Biol., vol. 52, No. 11, 2007, pp. 3151-3168.

Laplante et al., "Characterization of the Human Cytomegalovirus Protease As an Induced-Fit Serine Protease and the Implications to the Design of Mechanism-Based Inhibitors," J. Am. Chem. Soc., 121 (1999), 2974-2986.

Lei et al., "Tau protein: Relevance to Parkinson's disease," The International Journal of Biochemistry & Cell Biology, 42 (2010) 1775-1778.

Lin et al., "A benchmarking method to evaluate the accuracy of a commercial proton monte carlo pencil beam scanning treatment planning system," J. Appl. Clin. Med. Phys., vol. 18, 2017, pp. 44-49.

Lindborg et al., "Microdosimetry, Experimental Methods and Applications," CRC Press; 2017.

Marsolat et al., "Analytical linear energy transfer model including secondary particles: Calculations along the central axis of the proton pencil beam," Phys. Med. Biol., vol. 61, No. 2, 2016, pp. 740-757.

McMahon et al., "LET-weighted doses effectively reduce biological variability in proton radiotherapy planning," Phys. Med. Biol., vol. 63, 2018, 225009.

Newpower et al., "Using the Proton Energy Spectrum and Microdosimetry to Model Proton Relative Biological Effectiveness," Int. J. Radiat. Oncol. Biol. Phys., vol. 104, No. 2, 2019, pp. 316-324.

(56) References Cited

PUBLICATIONS

Olko P., "The microdosimetric one-hit detector model for calculating the response of solid state detectors," Radiat Meas., vol. 35, 2002, pp. 255-267.

Paganetti et al., "Report of the AAPM TG-256 on the relative biological effectiveness of proton beams in radiation therapy," Med. Phys., vol. 46, No. 3, 2019, pp. e53-e78.

Paganetti H., "Relative biological effectiveness (RBE) values for proton beam therapy, Variations as a function of biological endpoint, dose, and linear energy transfer," Phys. Med Biol., vol. 59, No. 22, 2014, pp. R419-R472.

Pedroni et al., "Experimental characterization and physical modelling of the dose distribution of scanned proton pencil beams," Phys Med. Biol., vol. 50, No. 3, 2005, pp. 541-561.

Peeler et al., "Clinical evidence of variable proton biological effectiveness in pediatric patients treated for ependymoma," Radiother Oncol., vol. 121, No. 3, 2016, pp. 395-401.

Perales et al., "Parameterising microdosimetric distributions of mono-energetic proton beams for fast estimates of yD and y," Biomed. Phys. Eng. Express, vol. 5, No. 4, 2019, doi:10.1088/2057-1976/ab236a.

Romano et al., "A Monte Carlo study for the calculation of the average linear energy transfer (LET) distributions for a clinical proton beam line and a radiobiological carbon ion beam line," Phys. Med. Biol., vol. 59, No. 12, 2014, pp. 2863-2882.

Rossi et al., "Microdosimetry and Its Applications," Berlin: Springer; 1996.

Rossi HH., "Spatial distribution of energy deposition by ionizing radiation source," Radiat. Res., vol. 2, 1960, pp. 290-299.

Saini et al., "Dosimetric evaluation of a commercial proton spot scanning Monte-Carlo dose algorithm: comparisons against measurements and simulations," Phys. Med. Biol., vol. 62, 2017, pp. 7659-7681.

Sanchez-Parcerisa et al., "Analytical calculation of proton linear energy transfer in voxelized geometries including secondary protons," Phys. Med. Biol., vol. 61, 4, 2016, pp. 1705-1721.

Sanchez-Parcerisa et al., "MultiRBE: Treatment planning for protons with selective radiobiological effectiveness," Med. Phys., 2019, doi:10.1002/mp.13718.

Schmidt et al., "Tau isoform profile and phosphorylation state in dementia pugilistica recapitulate Alzheimer's disease," Acta. Neuropathol, 101 (2001), 518-524.

Shively et al., Dementia Resulting From Traumatic Brain Injury: What Is the Pathology?, Arch. Neurol., 69(10) (2012) 1245-1251.

Smith et al., "Protein Accumulation in Traumatic Brain Injury," NeuroMolecular Medicine, 4 (2003), 59-72.

Sorriaux et al., "Experimental assessment of proton dose calculation accuracy in inhomogeneous media," Phys. Medica., vol. 38, 2017, pp. 10-15.

Soukup et al., "A pencil beam algorithm for intensity modulated proton therapy derived from Monte Carlo simulations," Phys. Med. Biol., vol. 50, No. 21, 2005, pp. 5089-5104.

Souris et al., "Fast multipurpose Monte Carlo simulation for proton therapy using multi- and many-core CPU architectures," Med. Phys., vol. 43, No. 4, 2016, pp. 1700-1712.

Stephen M. Seltzer, "New ICRU Recommendations on Key Data for Ionizing Dosimetry," CIRMS, (2016), 27 pages.

Ulmer W., "Theoretical aspects of energy-range relations, stopping power and energy straggling of protons," Radiat Phys. Chem., vol. 76, No. 7, 2007, pp. 1089-1107.

Ulmer W., "Theoretical methods for the calculation of Bragg curves and 3D distributions of proton beams," Eur. Phys. J. Spec. Top., vol. 190, No. 1, 2010, pp. 1-81.

Unkelbach et al., "Reoptimization of Intensity Modulated Proton Therapy Plans Based on Linear Energy Transfer," Int. J. Radiat. Oncol. Biol. Phys., vol. 96, No. 5, 2016, pp. 1097-1106.

Varian Medical Systems, Eclipse Scripting API Reference Guide, Version 15, 2015.

Varian, Eclipse Proton Algorithms Reference Guide, v13.7, 2015.

Wilkens et al., "Analytical linear energy transfer calculations for proton therapy," Med. Phys., vol. 30, No. 5, 2003, pp. 806-815.

Wilkens et al., "Three-dimensional LET calculations for treatment planning of proton therapy," Z. Med. Phys., vol. 14, No. 1, 2004, pp. 41-46.

Zhang et al., "The Microtubule-Stabilizing Agent, Epothilone D, Reduces Axonal Dysfunction, Neurotoxicity, Cognitive Deficits, and Alzheimer-Like Pathology in an Interventional Study with Aged Tau Transgenic Mice," The Journal of Neuroscience, 32(11), (2012), 3601-3611.

* cited by examiner

DETERMINING QUANTITIES OF INTEREST FOR PARTICLE THERAPY

BACKGROUND

Analytical pencil beam algorithms in proton therapy are now widely used and accepted as a reliable method for dose calculation due to their accuracy and computational efficiency[1-3]. This kind of algorithms use generally a model for the response (absorbed dose) for a proton beamlet, i.e., a kernel, to be convolved with the input beam, computed from a source beam model[4,5]. Similarly, the kernel approach is also commonly used for dose-averaged LET (LETd) calculations[6-8]. Most of these kernel approaches, although keep accuracy in central axis calculations, are not able to describe accurately the lateral profile observed when calculating LETd in proton beams using MC. More generally, pencil beam algorithms are not as accurate as Monte Carlo (MC) techniques, which can be considered as the gold standard[6], especially when dealing with inhomogeneities[7-9]. These shortcomings of the kernel based models makes necessary to add ad-hoc corrections or to use more complex models[9].

Pencil beam algorithms also require dedicated functions for each quantity to calculate, doubling the workload if both dose and LETd need to be determined. Again, MC methods are able to overcome this limitation since in a single simulation it is possible to score several quantities in a volume of interest. However, the computation requirements for MC simulations in terms of time and resources are clearly higher than for analytical algorithms.

Thus, there is a need for more sophisticated approaches to determining therapy related quantities.

SUMMARY

Methods and systems are described for determining quantities of interest for particle therapy. An example method can comprise determining one or more first functions indicative of spectral fluence associated with a particle therapy. The one or more first functions can be based on a plurality of simulations of a particle beam. The method can comprise determining, based on the one or more first functions and a second function associated with calculating a quantity, data indicative of the quantity. The method can comprise causing output of the data indicative of the quantity.

An example device can comprise one or more processors; and memory storing instructions that, when executed by the one or more processors, cause the device to determine one or more first functions indicative of spectral fluence associated with a particle therapy. The one or more first functions can be based on a plurality of simulations of a particle beam. The instructions can cause the device to determine, based on the one or more first functions and a second function associated with calculating a quantity, data indicative of the quantity. The instructions can cause the device to cause output of the data indicative of the quantity.

An example system can comprise a particle generator configured to generate a particle beam for a therapy. The example system can comprise one or more processors configured to determine one or more first functions indicative of spectral fluence associated with a particle therapy. The one or more first functions can be based on a plurality of simulations of the particle beam. The one or more processors can be configured to determine, based on the one or more first functions and a second function associated with calculating a quantity, data indicative of the quantity. The one or more processors can be configured to cause output of the data indicative of the quantity.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to limitations that solve any or all disadvantages noted in any part of this disclosure.

Additional advantages will be set forth in part in the description which follows or may be learned by practice. It is to be understood that both the foregoing general description and the following detailed description are exemplary and explanatory only and are not restrictive.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute a part of this specification, illustrate embodiments and together with the description, serve to explain the principles of the methods and systems.

DETAILED DESCRIPTION OF ILLUSTRATIVE EMBODIMENTS

Figure 1A:
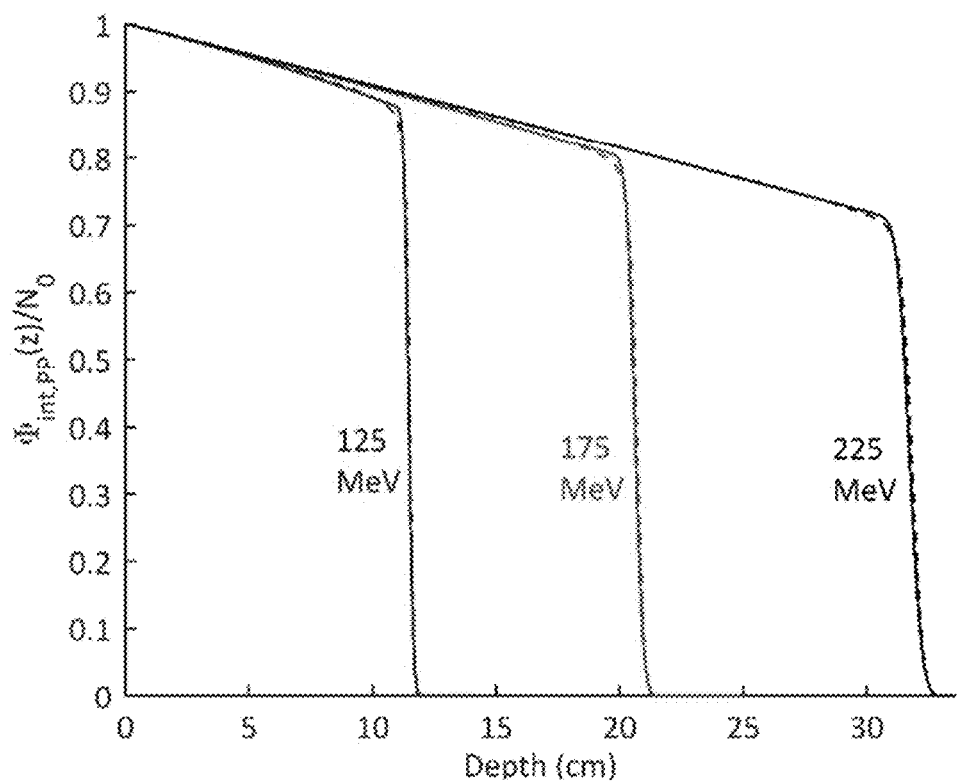
FIG. 1A shows example integrated fluence at each depth for primary protons obtained from simulations.

Disclosed herein is a new analytical methodology to calculate quantities of interest in particle radiotherapy inside the treatment planning system. Models are disclosed for calculating dose-averaged LET (LETd) in proton radiotherapy.

The disclosed techniques can comprise a kernel-based approach for the spectral fluence of particles is developed by means of analytical functions depending on depth and lateral position. These functions can be obtained by fitting them to data calculated with a simulation. An example simulation can comprise a Monte Carlo (MC) simulation. An example simulation can be based on water. An example simulation can be specific to an energy range (e.g., 50 MeV to 250 MeV). An example simulation can comprise Monte Carlo (MC) simulations using Geant4 in liquid water for energies from about 50 MeV to about 250 MeV. Contributions of primary, secondary protons and alpha particles can be modeled separately. For example, the primary protons can be modeled separately from the second protons and/or the alpha particles. The secondary protons can be modeled separately from the first protons and/or alpha particles. The alpha particles can be modeled separately from the primary protons and/or the secondary protons. The modeling can comprise modeling (e.g., or simulating) lateral profiles and/or spectra. Lateral profiles and/or spectra can be modeled as Gaussian functions to be convolved with the fluence coming from the nozzle. A variety of different quantities can be obtained, such as LETd. As an example, LETd can be obtained by integrating the stopping power curves from the PSTAR and ASTAR databases weighted by the spectrum at each position. The fast MC code MCsquare is employed to benchmark the results.

The results described further herein show that the disclosed techniques provide for accurate and efficient calculation of various quantities of interest. Considering the nine energies simulated, fits for the functions modeling the fluence in-depth provide an average $R^2$ equal to 0.998, 0.995 and 0.986 for each one of the particles considered. Fits for the Gaussian lateral functions yield average $R^2$ of 0.997, 0.982 and 0.993, respectively. Similarly, the Gaussian functions fitted to the computed spectra lead to average $R^2$ of 0.995, 0.938 and 0.902. LETd calculation in water shows mean differences of −0.007±0.008 keV/μm with respect to MCsquare if only protons are considered and 0.022±0.007 keV/μm including alpha particles. In a prostate case, mean difference for all voxels with dose greater than 5% of prescribed dose is 0.28±0.23 keV/μm.

The new spectral fluence-based methodology disclosed herein allows for simultaneous calculations of quantities of interest in proton radiotherapy such as dose, LETd or microdosimetric quantities. The method also enables the inclusion of more particles by following an analogous process.

Introduction

In this work, an approach different than conventional approaches described above is proposed to address calculations of different quantities of interest (QOIs) in proton therapy, and particularly, LETd. Instead of using specific quantity-depending kernels (e.g., such as dose kernels or LET kernels), a more general kernel for the spectrum of proton beams (e.g., in terms of kinetic energy or, equivalently, range of the particles) at each spatial point (e.g., spectral fluence) is proposed. This allows for a more MC-alike approach since the information about the density of particles present and their energy is taken into account along their whole path. Then, simultaneous calculations for poly-energetic beams can be carried out by integrating the corresponding function on the energy for each QOI. As described further herein particular results for LETd can be determined by using the stopping power data from NIST. Additionally, in previous works we have developed some functions dependent on the kinetic energy of protons to calculate dose-mean linear energy ($y_D$) and LETd from microdosimetry by using MC simulations[10,11]. The method presented here also enables calculations of three-dimensional distributions of these microdosimetric QOIs.

Methods and Material:

General Calculations of QOIs

Stopping power for protons and other particles is generally available in terms of the kinetic energy of the particle from different databases[12,13]. Such energy-dependent functions can rely on the knowledge of the particle spectrum to be used. In this way, if $\phi(r)$ is the fluence at a point r, given the spectral fluence $\phi_E(E;r) \equiv d\phi(r)/dE$ at a certain point r, the average value for a generic energy-dependent function q=q(E) at that point will be given by $$\bar{q}(r) = \frac{\int q(E)\phi_E(E;r)dE}{\int \phi_E(E;r)dE} \quad (1)$$

Possible simple examples of quantities based on electronic stopping power S(E) that can be calculated with equation (1) are: (i) dose, by introducing $q(E)=S(E)/(A\rho)$ in the integration, where A is the cross-sectional area of a voxel and p is the physical density of water; or (b) track-averaged LET, $\bar{L}_T$, by simply exchanging q(E)=S(E). Furthermore, more complex quantities can be calculated as well, such as dose-averaged LET ($\bar{L}_D$), by computing separately equation (1) with $q(E)=S^2(E)$ and q(E)=S(E) and dividing the final results. The latter example is used in this work to show results. Therefore, this work is centered on how to determine $\phi_E(E;r)$ as this quantity allows for a variety of different calculations of interest.

In equation (1), the spectral fluence $\phi_E(E)$ acts as a weight for each spectral component in the energy-dependent function q(E). Equivalently, if the relation between energy and range in the continuous slow-down approximation (CSDA) is known, R=R(E), then the average value for q at a point r can be alternatively computed as $$\bar{q}(r) = \frac{\int q(R)\phi_R(R;r)dR}{\int \phi_R(R;r)dR} \quad (2)$$

where $\phi_R(R;r) \equiv d\phi(r)/dR$ is the fluence range-density, e.g., the relative number of particles per cross-sectional unit area with CSDA range equal to R with respect to the total number of particles per cross-sectional unit area at r. This second approach is preferred because of practical reasons. Concretely, the variation of stopping power and other QOIs with the CSDA range is smoother than with the particle energy, assuming as this relation $R(E)=\alpha E^p$, i.e. the Bragg-Kleeman rule[14]. Therefore, if the energy-dependent functions $\{q_j(E)\}$ and the transform rule to CSDA range R=R(E) are known, according to equation (2), our problem is reduced to the determination of $\phi_R(R;r)$ at each point of interest.

Application to Clinical Beams

A clinical beam is generally composed of the superposition of several layers, being each one of them calculated independently. In a pencil beam scanning (PBS) system, a beam is composed of spots that are magnetically scanned to achieve a conformal dose distribution. Note that a layer may be defined by a nominal energy, a reference system (beam angle and isocenter position) and a two-dimensional map of spot-fluence weights. In this context, $\phi_R(R;r)$ is the total resulting fluence range-density and can be obtained as a combination of the fluence range-density for each beam, which, in turn, is a combination of the individual fluence coming from each spot. Let $N_L$ be the number of layers present in a given beam and $\phi_{R,i}(R;r)$ the fluence range-density for the i-th layer. If $\phi_i(r)$ is the total fluence that the i-th layer carries to the point r, then $$\phi_R(R;r) = \frac{\sum_{i=1}^{N_L} \phi_i(r)\phi_{R,i}(R;r)}{\sum_{i=1}^{N_b} \phi_i(r)} \quad (3)$$

Equation (3) represents a weighted average for the different spectral fluence converging at a point r, in which the weights are their corresponding fluences. Consequently, it becomes necessary to determine the number of particles per area unit carried by each layer at each point. This determination, however, is a problem frequently solved in pencil beam algorithms as follows. A treatment planning system (TPS) with pencil beam scanning (PBS) system, should provide the following information of a layer: (i) its nominal energy with a certain initial spread $\tau_{ini}$; and (ii) the lateral width of the spots $\sigma_{lat,spot}(z)$ on that layer at a certain reference depth, normally the isocenter[15]. In this sense, $\phi_{R,i}(r)$ can be obtained by summing the contributions from every individual spot composing it and, in turn, that contribution for each spot is obtained from the composition of different infinitely narrow beam, usually called beamlets. Then, it is convenient to separate the problem of determining $\phi_{beamlet}(r)$ for each beamlet into two different functions: one depending only on the depth in water (integrated fluence, e.g., total number of particles at each depth) and the other depending on the lateral distance to the beam propagation axis $\rho$ at each depth z, $\phi_{beamlet}(r)=(\Phi_{int}(z)/\Phi_0) \phi_{lat,beamlet}(\rho;z)$, where $\Phi_{int}(z)/\Phi_0$ represents the fraction of particles arriving at each depth with respect to the total number of particles coming from the water surface.

Now, $\sigma_{lat,spot}(z)$ refers to the width of the spot's lateral profile for the fluence at a depth z for a layer, which becomes larger as it goes away from the source due to the beam divergence. Furthermore, when those particles travel through matter (particularly, water), they undergo scattering processes, and thus, the lateral distribution of particles becomes broader. This can be incorporated by generating a lateral kernel for a beamlet, which, essentially, represents the probability density for a particle to reach each lateral position. In other words, if at a certain depth z the probability density for a single particle to be scattered up to a lateral distance $\rho$ is given by $K_w(\rho;z)=\phi_{lat,beamlet}(\rho;z)$, then the fluence for a spot at that point will be given by the convolution $$\phi_{spot}(R) = \frac{\Phi_{int}(z)}{\Phi_0} \int \phi_{lat,spot}(\rho';z)K_w(\rho'-\rho;z)d\rho' \quad (4)$$

Here, again, $\phi_{lat,spot}(\rho;z)$ represents the fluence for each spot coming from the nozzle taking into account the beam divergence and it is usually provided by the TPS and modeled as a single Gaussian function thus $\phi_{lat,spot}(\rho;z)=\exp(-\rho^2/(2\sigma_{lat,spot}^2(z)))$. Finally, the fluence for the overall i-th layer can be obtained by convolving again the fluence for a single spot at each depth, $\phi_{spot}(r)$, with its two-dimensional map of spot weights produced by the PBS system, $w(x, y)$:

$$\phi_i(r) = \int \phi_{spot}(x',y';z) w(x-x', y-y') dx' dy' \quad (5)$$

where now lateral coordinates have been transformed from cylindrical to Cartesian. This way equation (5) provides the weights in the weighted average of spectral fluences shown in equation (3).

Beam Components

Generally, one can distinguish between two different types of particle components present in a beam according to their different behavior in depth and laterally. In this disclosure, as an example, distinction provided by the MC package Geant4[16-18] can be used: primary particles can be those that have undergone only electromagnetic and hadronic elastic collisions while secondary particles are those generated in nuclear inelastic collisions and in charge-exchange processes. Furthermore, one can differentiate between secondary particles with equal or different nature than the primaries, e.g. in a proton beam. The following three categories may be used (e.g., modeled separately): primary protons, secondary protons, and the rest of secondary particles. Each one of these categories comprise particles with diverse behavior. In other words, the functions $\Phi_{CAX,P}(z)$ and $K_{w,P}(\rho; z)$ vary depending on the type of particle P considered. Additionally, the fluence range-density $\phi_{R,i}(R; r)$ also depends on the type of particle so that each category can be considered separately up to equation (3). Then, equation (2) becomes $$\bar{q}(r) = \frac{\int \sum_{P=1}^{N_P} q_P(R) \phi_{R,P}(R; r) dR}{\int \sum_{P=1}^{N_P} \phi_{R,P}(R; r) dR} \quad (6)$$

where $N_p$ is the number of types of particles and $q_p(R)$ and $\phi_{R,P}(R; r)$ are, respectively, the function of interest and the outcome of equation (2) for the type of particle P.

Models for Proton Beams: Monte Carlo Simulations

A new methodology is disclosed herein that is different than a conventional pencil beam algorithm. Pencil beam algorithms traditionally model the dose (or LET) deposited by a beamlet (e.g., a kernel). Then, the total dose for a broad beam is computed by convolving the kernel across the plurality of beamlets that a beam is composed of. It is important to remark that the disclosed techniques do not use dose- or LET-based kernels, but rather fluence (e.g., number of particles per area unit, which is closely related to dose) and, particularly, spectral fluence (e.g., distribution of energy of the particles in a beamlet). The proposed kernels and procedures for obtaining spectral fluence are new and nonconventional in comparison to the techniques used in pencil beam based approaches.

The value $q(r)$ can be determined based on determining the functions $\phi_{R,P}(R; r)$, $\Phi_{int,P}y(z)$ and $K_{w,P}(\rho; z)$ for all the components of the beam to be considered. Disclosed herein are analytical forms for these functions applied to the case of proton beams with energies in the typical clinical range: from 50 MeV to 250 MeV at intervals of 25 MeV. MC simulations for the transport of $5 \cdot 10^7$ protons in liquid water have been performed with Geant4 v 10.5.0 for each one of these energies; QGSP_BIC_HP with the most accurate physics list, G4EmStandardPhysics option4, was used. Three types of particles can be distinguished: primary protons, secondary protons and secondary alpha particles. The rest of the particles generated in such interactions can be disregarded in this model due to their low proportion[19] for the sake of simplicity and efficiency.

It is worth to note that, apart from the explicit dependencies already shown, the functions to model can also depend on the nominal energy of the layer under consideration, $E_0$, therefore this dependency is introduced explicitly as well. As seen in equation (4), the function $K_{w,P}(\rho; z; E_0)$ can first be convolved with $\Phi_{lat,spot}$, which is usually a Gaussian function given by the TPS, and later with the spot weights map $w(x, y)$, as shown in equation (5). As the convolution operation between Gaussian functions becomes as easy as a quadratic sum of the $\sigma$ parameters, we look for single or multiple Gaussians to model $K_{w,P}(\rho; z; E_0)$ by fitting these functions to the lateral distributions obtained from our MC simulations. For the depth dependency no special operations are needed so that $\Phi_{int,P}(z; E_0)$ is open to any functional form able to produce good agreement with MC data. Finally, $\phi_{R,P}(R; r)$ can be modeled as any well-behaved function to perform the integrations in equation (6).

Number of Particles with Depth in Water

The dependency of the number of primary protons (PP) at each depth can be modeled (e.g., according to Ulmer's work[4]) by a function as the following one:

$$\frac{\Phi_{int,PP}(z; E_0)}{\Phi_0(E_0)} = \left(1 - \frac{\xi(E_0)z}{R(E_0)}\right) \frac{1}{2} \left(1 + \mathrm{erf}\left(\frac{R(E_0) - z}{\sqrt{2}\,\tau(E_0)}\right)\right) \quad (7)$$

where $\Phi_0(E_0)$ is the number of protons reaching the water surface (z=0), $R(E_0)$ is the CSDA range of protons with energy $E_0$ and $\xi(E_0)$ and $\tau(E_0)$ are the parameters of the model. The dependency on the nominal energy of the layer can be addressed as follows: the function proposed in equation (7) can be fitted against the results from MC simulations for each one of the simulated energies. Therefore, a set of values for the parameters $\xi(E_0)$ and $\tau(E_0)$ are obtained. To calculate the function $\Phi_{int,PP}(z; E_0)$ for an energy $E'_0$ between two simulated energies, we first can define the depth-scaled to the range $z_{sc}(E_0) = z/R(E_0)$. Then, $\Phi_{int,PP}(z_{sc}^\uparrow; E_0^\uparrow)$ and $\Phi_{int,PP}(z_{sc}^\downarrow; E_0^\downarrow)$ can be computed according to equation (6), where $E_0^\uparrow$ and $E_0^\downarrow$ are, respectively, the immediately higher and lower simulated energies to $E'_0$ and $z_{sc}^\uparrow$ and $z_{sc}^\downarrow$ are the depth-scaled to the range corresponding to those energies. Finally, a linear interpolation between those two values can be performed so that $$\Phi_{int,PP}(z; E'_0) = \qquad (8)$$
$$\Phi_{int,PP}(z_{sc}^\downarrow; E_0^\downarrow) + \left(\Phi_{int,PP}(z_{sc}^\uparrow; E_0^\uparrow) - \Phi_{int,PP}(z_{sc}^\downarrow; E_0^\downarrow)\right) \frac{E'_0 - E_0^\downarrow}{E_0^\uparrow - E_0^\downarrow}$$

This is an example approach that can be followed to compute all the functions here presented for any nominal energy between the simulated ones.

For the number of secondary protons (SP) at each depth, the following function can be used:

$$\frac{\Phi_{int,SP}(z; E_0)}{\Phi(E_0)} = \frac{\xi(E_0)z}{R(E_0)} \frac{1}{2}\left(1 + \mathrm{erf}\left(\frac{R(E_0) - z}{\sqrt{2}\,\tau(E_0)}\right)\right)(\alpha_0(E_0) - \alpha_1(E_0)z^{\alpha_2(E_0)}) \quad (9)$$

where $\Phi_0(E_0)$, $R(E_0)$, $\xi(E_0)$ and $\tau(E_0)$ are the same as in equation (7) and $\alpha_0(E_0)$, $\alpha_1(E_0)$ and $\alpha_2(E_0)$ are the parameters to be determined. These parameters have no physical meaning since the function has been selected to achieve a good fit to the MC results.

A similar function can be proposed to model the proportion of alpha particles (AP) in depth:

$$\frac{\Phi_{int,AP}(z; E_0)}{\Phi_0(E_0)} = P_4(z; E_0)\left(1 + \text{erf}\left(\frac{R(E_0) - z}{\sqrt{2}\,\tau_{AP}(E_0)}\right)\right) \quad (10)$$

where $\Phi_0(E_0)$ and $R(E_0)$ are the same as in equation (7), $\tau_{AP}(E_0)$ is a parameter and $P_4(z; E_0)$ is a fourth-grade polynomial function that carries five additional parameters for each simulated energy.

Lateral Kernel

Lateral kernels for fluence are similar to other pencil beam algorithms use for dose. Here, the lateral kernel $K_{w,PP}(\rho; z; E_0)$ for the fluence of primary protons is modeled simply as a single Gaussian centered at the central axis and normalized:

$$K_{w,PP}(\rho; z; E_0) = \frac{1}{\sqrt{2\pi}\,\sigma_{lat,PP}(z; E_0)} \exp\left(-\frac{\rho^2}{2\sigma_{lat,PP}^2(z; E_0)}\right) \quad (11)$$

The parameter $\sigma_{lat,PP}(z; E_0)$ can be used characterize the function although its dependency on depth can be determined. In order to do that, for each simulated nominal energy $E_0$, we fit $K_{w,PP}(\rho; z; E_0)$ to the obtained lateral distributions at each depth z with intervals of 0.5 mm and obtain $\sigma_{lat,PP}(z; E_0)$. The dependency of this parameter with depth can be modeled, for each nominal energy $E_N$, as a polynomial function:

$$\sigma_{lat,PP}(z;E_0)=a_{0,PP}(E_0)+a_{1,PP}(E_0)z+a_{2,PP}(E_0)z^2+a_{3,PP}(E_0)z^3 \quad (12)$$

Lateral distributions for secondary protons have a more prominent tale than for primaries, so that a second Gaussian can be used for a better fit to the MC results. Therefore, the following may be used $$K_{w,SP} = \frac{w_{SP}(z; E_0)}{\sqrt{2\pi}\,\sigma_{l1,SP}(z; E_0)} \exp\left(-\frac{\rho^2}{2\sigma_{l1,SP}^2(z; E_0)}\right) + \frac{(1 - w_{SP}(z; E_0))}{\sqrt{2\pi}\,\sigma_{l2,SP}(z; E_0)} \exp\left(-\frac{\rho^2}{2\sigma_{l2,SP}^2(z; E_0)}\right) \quad (13)$$

where now three parameters are used to characterize the kernel: $w_{SP}(z; E_0)$, $\sigma_{l1,SP}(z; E_0)$ and $\sigma_{l2,SP}(z; E_0)$ These parameters can be obtained for each depth according to polynomial functions of first, second and third-grade, respectively, similar to the one in equation (12).

For the lateral distribution of alpha particles fluence, a single Gaussian can be used so that $$K_{w,AP}(\rho; z; E_0) = \frac{1}{\sqrt{2\pi}\,\sigma_{lat,AP}(z; E_0)} \exp\left(-\frac{\rho^2}{2\sigma_{lat,AP}^2(z; E_0)}\right) \quad (14)$$

where $\sigma_{lat,AP}(z; E_0)$ is obtained as a function of depth by fitting a third-grade polynomial function, as in the case of primary protons shown in equation (12).

Fluence Range-Density or Spectrum in Terms of CSDA Range

While the previous functions are intended to provide fluences similarly as done in other pencil beam algorithms, the disclosed formalism differs when characterizing the kernels for beamlets' spectra. In order to determine the spectral components of the beam at each point, here $\phi_{R,P}(R; r; E_0)$ represents the probability density for the CSDA range at each spatial position when a single particle of energy $E_0$ is considered. For all types of particles here presented, $\phi_{R,P}(R; r; E_0)$ is modeled as a single normalized Gaussian function, which is fully characterized by two parameters: mean $\mu_{R,P}(r; E_0)$ and standard deviation $\sigma_{R,P}(r; E_0)$. This means that, at each point r, the probability density for a particle of type P and initial energy $E_0$ corresponding to a given CSDA range can be given by $$\phi_{R,P}(R; r; E_0) = \frac{1}{\sqrt{2\pi}\,\sigma_{R,P}(r; E_0)} \exp\left(-\frac{(R - \mu_{R,P}(r; E_0))^2}{\sigma_{R,P}^2(r; E_0)}\right) \quad (15)$$

When a particle penetrates in water, its probability to appear at a certain point decreases with the distance from the central axis. In the same way, the particle energy spectrum also depends on the position. Concretely, in a central axis point, the particle likely will have a higher energy than in a radial point. In other words, the mean of $\phi_{R,P}(R; r; E_0)$ decreases radially. Proposed, in a similar way than for the fluence, is an example decomposition in terms of depth and lateral components thus $$\mu_{R,P}(r;E_0)=\mu_{CAX,P}(z;E_0)K_{\mu_{R,P}}(\rho;z;E_0) \quad (16)$$

where $K_{\mu_{R,P}}(\rho; z; E_0)=\exp(-\rho^2/2\sigma_{lat,\mu_{R,P}}^2(z; E_0))$ is taken again as a Gaussian function on the radial position to the central axis, as in equation (11) and represents the lateral variation for the mean CSDA range $\mu_{R,P}(r; E_0)$. The dependency of parameters $\mu_{CAX,P}(z; E_0)$ and $\sigma_{lat,\mu_{R,P}}(z; E_0)$ with depth is modeled again by polynomial functions. An exception is the case of primary protons, in which the mean of the spectrum in terms of CSDA range is taken as the residual range, i.e. $\mu_{CAX,P}(z; E_0)=R(E_0)-z$. Note that $K_{\mu_{R,P}}(\rho; z; E_0)$ is, by itself, a new lateral kernel, so that the actual mean value $\mu_{R,P}(r; E_0)$ at a point r for a spot with lateral fluence in air $\Phi_{lat,spot}(\rho; z)$ can be given by a new convolution:

$$\mu_{R,P}^{spot}(r;E_0)=\mu_{CAX,P}(z;E_0)\int\Phi_{lat,spot}(\rho';z)K_{w,P}(\rho'-\rho;z) K_{\mu_{R,P}}(\rho'-\rho;z;E_0)d\rho' \quad (17)$$

where the explicit energy dependency is excluded for simplification. Note that the mean $\mu_{R,P}(r; E_0)$ can be obtained by convolving the model for single particles, given in equation (16), with the actual number of particles coming from the spot, which includes the lateral fluence kernel $K_{w,P}(\rho; z)$ as shown in equation (4). Again, the mean value at each point for the overall layer can be obtained by convolving equation (16) with the spot weights map:

$$\mu_{R,P}(r;E_0)=\int\mu_{R,P}^{spot}(x',y',z;E_0)w(x-x',y-y')dx'dy' \quad (18)$$

In contrast with the mean value, in order to reduce the complexity of the model, standard deviation can be considered as constant laterally, i.e. $\sigma_{R,P}(r; E_0)=\sigma_{R,P}(z; E_0)$. This parameter, again, can be modeled in depth as a polynomial function.

Application to a Particular Quantity: Dose-Averaged LET Calculation

Consider the case of calculating dose-averaged LET using the fluence kernel proposed above. Dose-average LET can be defined as[20]

$$\bar{L}_D(r) = \frac{\int S^2(E)\phi_E(E;r)dE}{\int S(E)\phi_E(E;r)dE} = \frac{\overline{S^2}(r)}{\overline{S}(r)} \quad (19)$$

where S(E) is the electronic stopping power of the considered particle as a function of its kinetic energy. This can be calculated according to Eq. (5) at each point r as, and $$\overline{S^2}(r) = \frac{\int \sum_{P=1}^{N_P} S_P^2(R)\phi_{R,P}(R;r)dR}{\int \sum_{P=1}^{N_P} \phi_{R,P}(R;r)dR} \quad (20)$$

$$\overline{S}(r) = \frac{\int \sum_{P=1}^{N_P} S_P(R)\phi_{R,P}(R;r)dR}{\int \sum_{P=1}^{N_P} \phi_{R,P}(R;r)dR} \quad (21)$$

where all symbols coincide with those in equation (6) exchanging the generic quantity $q_P(R)$ by $S_P^2(R)$ and $S_P(R)$, respectively. Note that now the stopping power $S_P(R)$ for the particle P is expressed in terms of the CSDA range instead of the energy of the particle. It is possible to perform such integrations by using the model presented in the previous section and the stopping power and range data for each energy in the NIST databases[12].

This model has been implemented in C # code and integrated into the Varian Eclipse TPS (version 15) through the Eclipse Scripting Application Programming Interface (ESAPI)[21] in order to calculate 3D distributions in real clinical proton beams. All calculations were performed with a beam model of a pencil beam scanning (PBS) system from IBA. A parallelepiped structure with 10 cm in-length and square base (5.5 cm×5.5 cm) is defined in a large cube of liquid water with its distal face at 20 cm in-depth. A beam is generated in Eclipse to produce a uniform dose over that structure. To benchmark the results, the same geometry is simulated using the fast MC code MCsquare[22] by simulating $10^9$ primary particles. The LETd calculations are computed in MCsquare by using the scoring method labeled as 'C' in Cortes-Giraldo and Carabe's work[23]. We performed two comparisons: (a) only considering primary and secondary protons in both systems and (b) adding just the alpha particles' contribution in our method and in MCsquare, with a specially devoted version for this work.

Finally, calculations can be performed based on a medium different from water. In order to do that, the depth in water, z, can be replaced by the corresponding water-equivalent thickness $Z_{WET}$ resulting from the beam raytracing throughout all the previous equations. One can consider a prostate case treated with two single-field-optimized lateral beams and compare the distributions of $\bar{L}_D$ resulting from our method and MCsquare.

Results

Figure 1B:
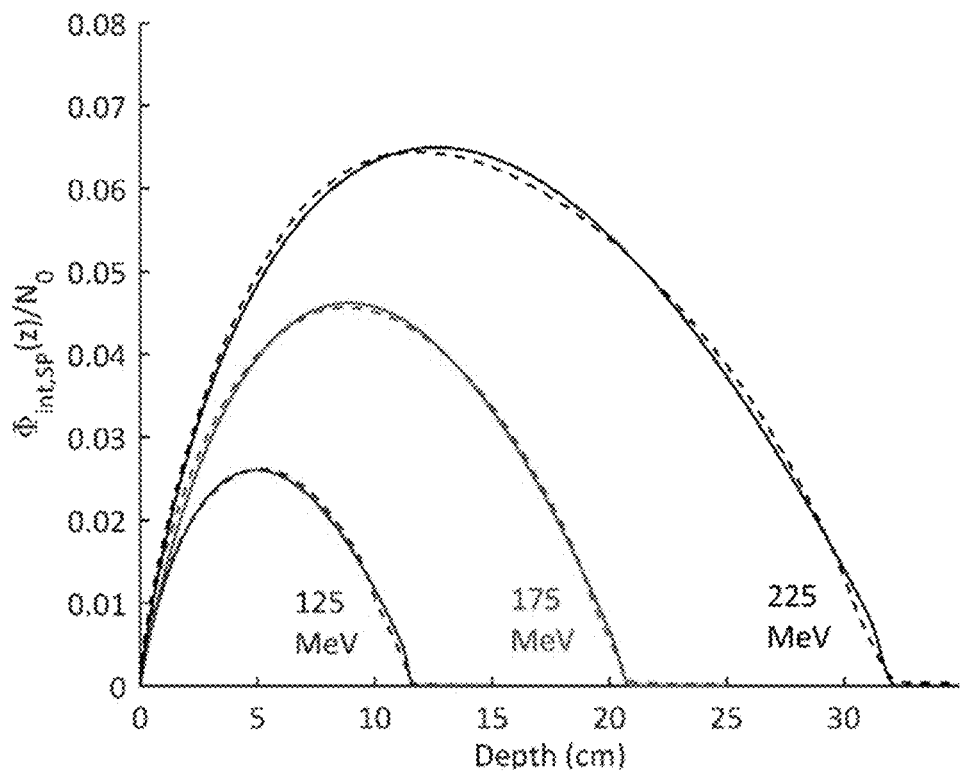
FIG. 1B shows example integrated fluence at each depth for secondary protons obtained from simulations.
Figure 1C:
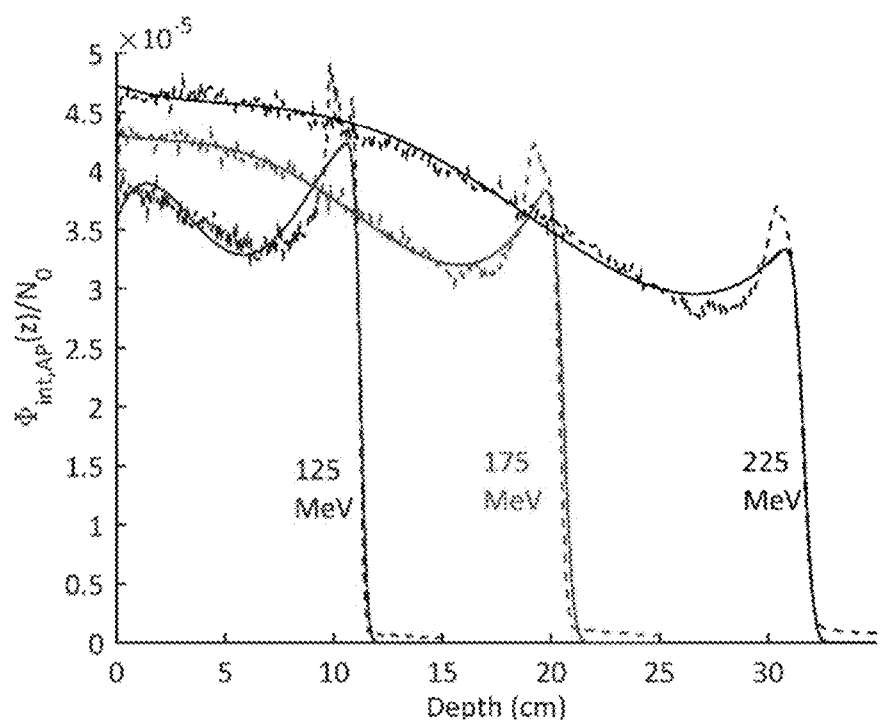
FIG. 1C shows example integrated fluence at each depth for alpha particles obtained from simulations.

FIGS. 1A-C show the integrated fluence at each depth for primary protons, secondary protons and alpha particles obtained from simulations with Geant4. Fits for the functions shown in equations (7), (9) and (10) are also shown. Results for only three energies (125 MeV, 175 MeV and 225 MeV) are shown to ease the visualization. Similar trends are obtained for the rest of the energies. As a measurement of the goodness of the fits, for primary protons the nine simulated energies provide a mean $R^2$=0.998, for secondary protons $R^2$=0.995 and for alpha particles $R^2$=0.986.

FIG. 1A shows fraction of primary protons in depth respect to the number of protons arriving at water surface ($N_0$). FIG. 1B shows the fraction of secondary protons in depth respect to the number of protons arriving at water surface ($N_0$). FIG. 1C shows the fraction of alpha particles in depth respect to the number of protons arriving at water surface ($N_0$). Dashed lines represent the results obtained from Geant4 simulations for protons of 125 MeV (blue), 175 MeV (red) and 225 MeV (black). Solid lines are the fits obtained with the functions shown in equations (7), (9) and (10) for the for FIGS. 1A, 1B, and 1C, respectively.

Figure 2A:
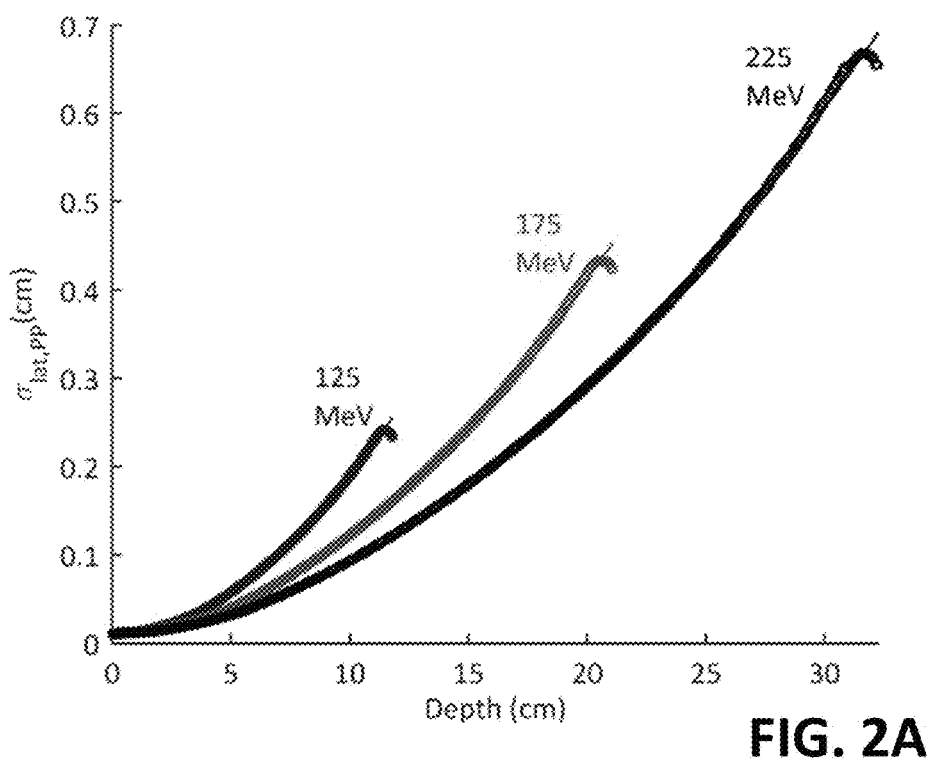
FIG. 2A shows an example parameter for primary protons at the three different energies.
Figure 2B:
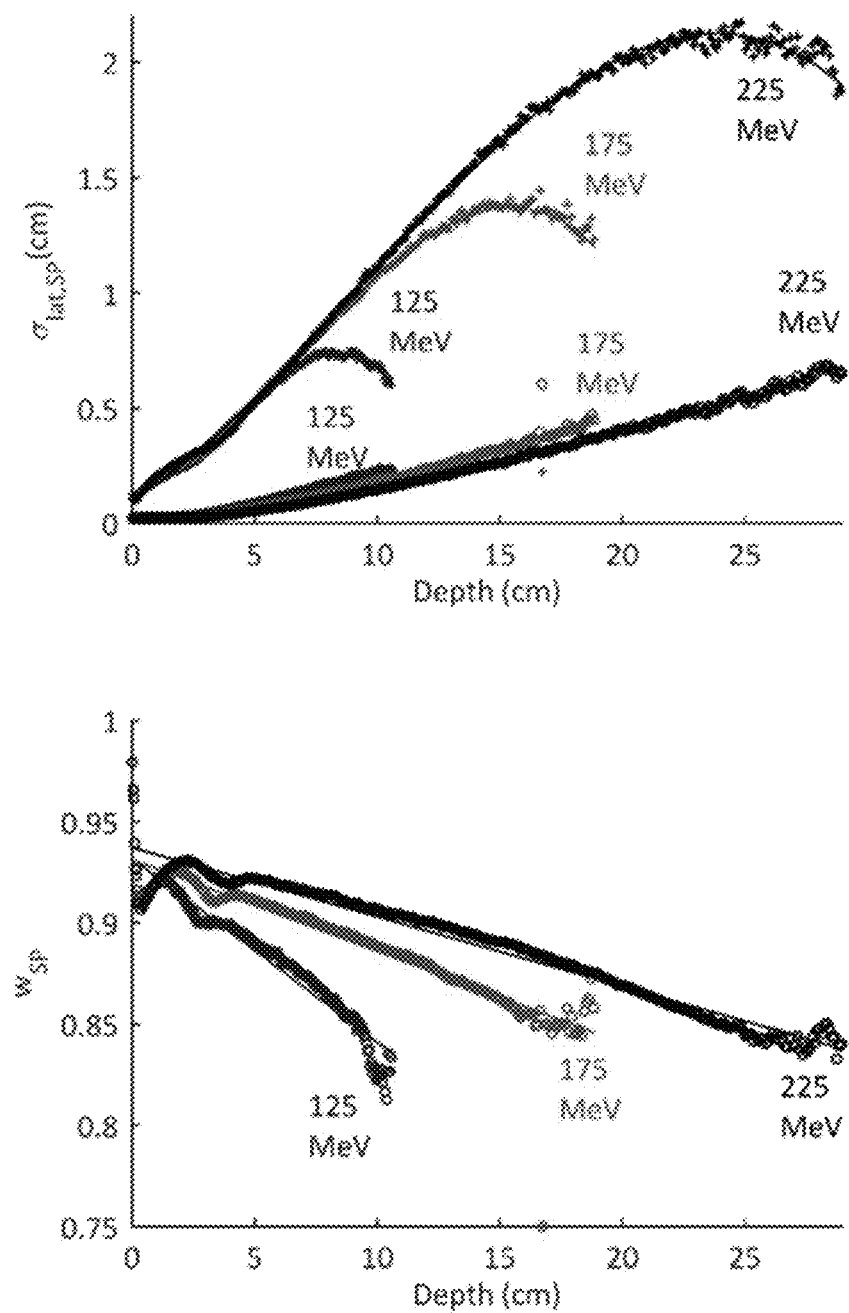
FIG. 2B shows an example parameter for secondary protons at the three different energies.
Figure 2C:
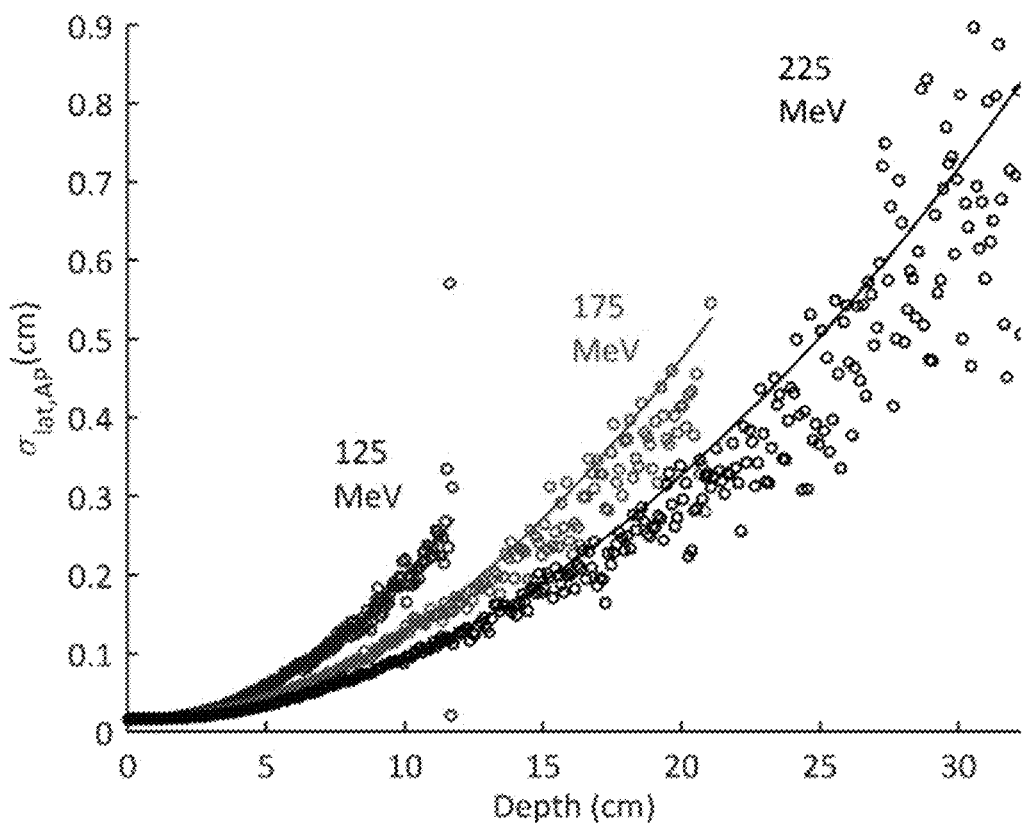
FIG. 2C shows an example parameter for alpha particles.

Lateral distributions for primary protons and secondary alphas are modeled as single Gaussian functions at every individual depth considered. Whereas, for secondary protons, a double Gaussian function is employed. The goodness of these fits can be evaluated through the mean $R^2$ for each one of the nine energies employed. The averages and standard deviations of these sets of nine mean $R^2$ are 0.997±0.0004 for primary protons, 0.982±0.0007 for secondary protons and 0.993±0.003 for alpha particles. FIGS. 2A-C shows the dependency of the lateral a for each case for the same three selected energies than in FIGS. 1A-C.

FIGS. 2A-C show parameters to characterize the lateral distribution for particles for three different energies: 125 MeV (blue), 175 MeV (red) and 225 MeV (black). FIG. 2A shows an example parameter for primary protons at the three different energies. FIG. 2B shows an example parameter for secondary protons at the three different energies. FIG. 2C shows an example parameter for alpha particles. Polynomial functions are fitted to the points, obtained, in turn, by fitting a single Gaussian functions in the cases FIG. 2A and FIG. 2C and Double Gaussian functions for the case FIG. 2B to the lateral profile at each independent depth. These parameters correspond to those in equations (11), (13) and (14) and are used to build the lateral kernels at each depth and for each energy. FIG. 2A shows $\sigma_{lat,PP}$ obtained from Single Gaussian fit to Geant4 data (dots), and Polynomial fit (solid line); Equation (11). FIG. 2B shows $\sigma_{l1,SP}$ and $w_{SP}$ obtained from Double Gaussians fits to Geant4 data (dots), $\sigma_{l2,SP}$ obtained from Double Gaussians fits to Geant4 data (plus signs), and Polynomial fits (solid line). FIG. 2C shows $\sigma_{lat,AP}$ obtained from Single Gaussian fit to MC data (dots), and Polynomial fit (solid lines).

Figure 3A:
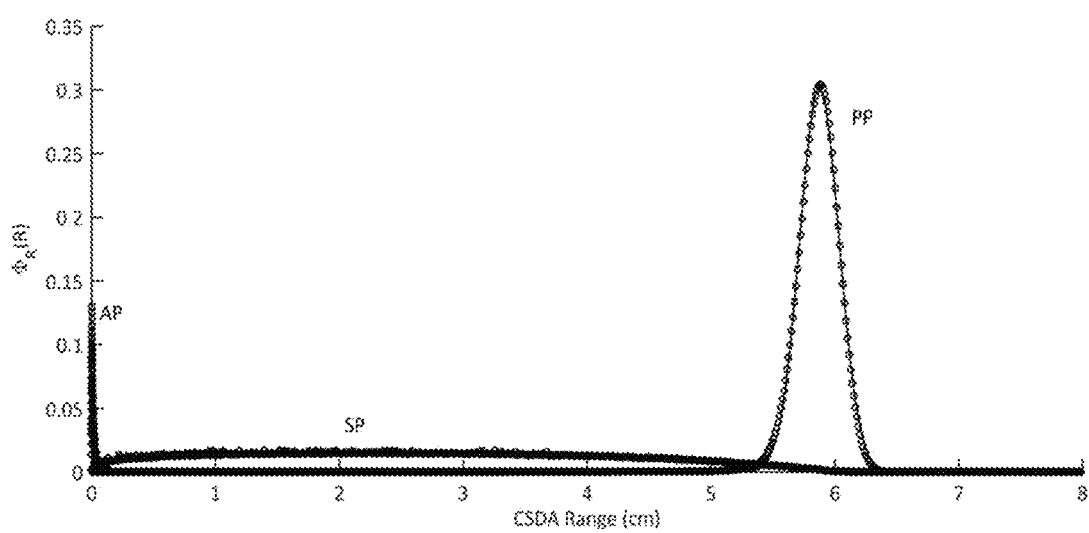
FIG. 3A shows an example of the spectrum obtained from Geant4 MC simulations and the fitted functions (beam energy of 150 MeV at 10 cm in depth).
Figure 3B:
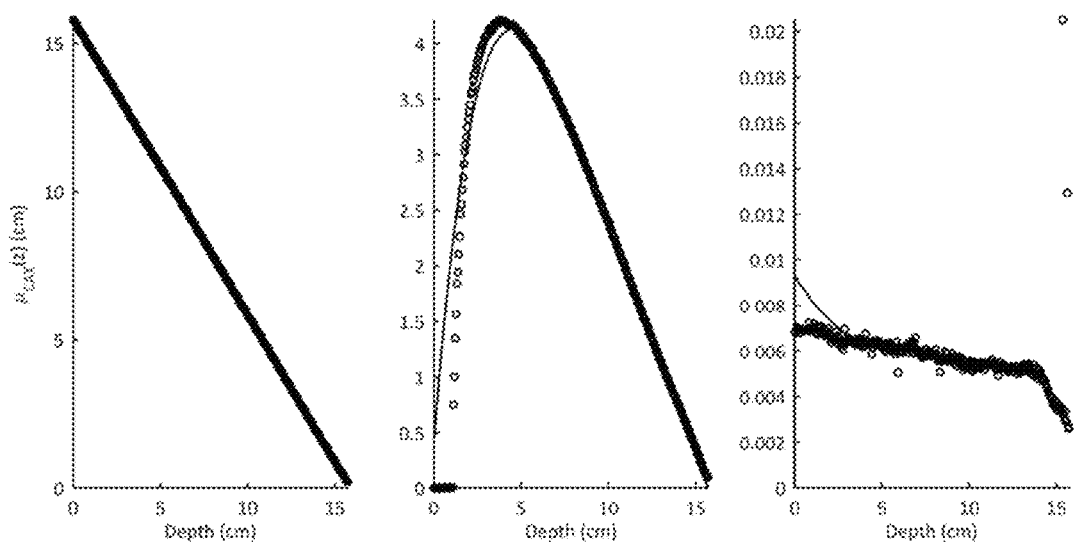
FIG. 3B shows the dependency of the mean range on the depth for the same beam energies.
Figure 3C:
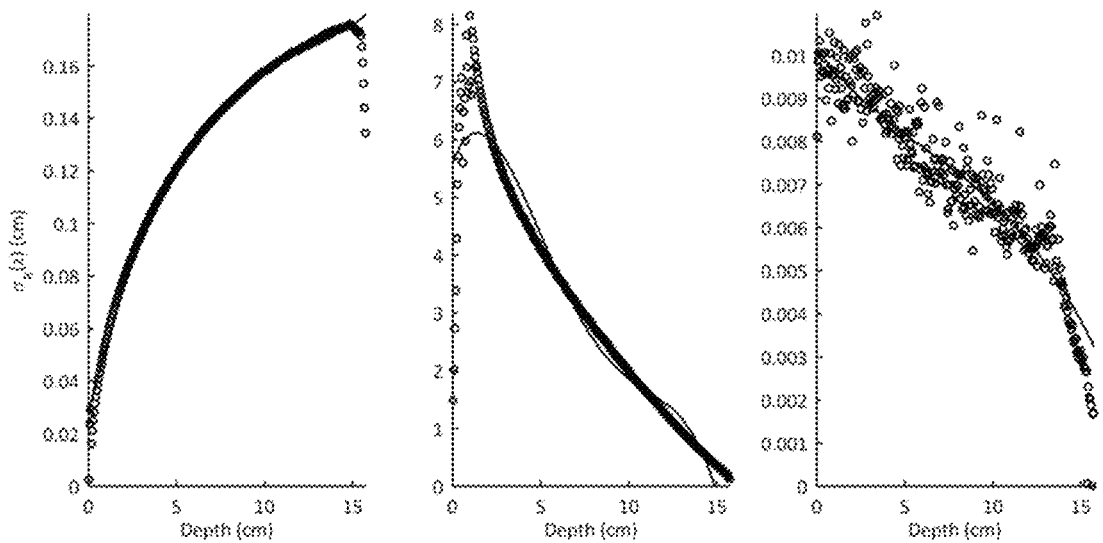
FIG. 3C shows the standard deviation for the Gaussian functions for the same beam as in FIGS. 3A-B.

The spectrum in terms of CSDA range for each component is modeled as a single Gaussian function. FIG. 3A shows an example of the spectrum obtained from Geant4 MC simulations and the fitted functions (beam energy of 150 MeV at 10 cm in depth). The overall goodness of this fits is evaluated through the average of the mean $R^2$ parameters obtained for each energy along all the considered depths: 0.995±0.001 for primary protons, 0.938±0.025 for secondary protons and 0.90±0.02 for alpha particles. FIG. 3B shows the dependency of the mean range on the depth for the same beam energies. Note that the relation between CSDA range and kinetic energy is different for protons and for alpha particles. FIG. 3C shows the standard deviation for the Gaussian functions for the same beam than in FIGS. 3A-B.

FIG. 3A shows examples of spectra for primary protons, secondary protons and alpha particles in terms of CSDA range for a single-layer proton beam of 150 MeV at a depth equal to 10 cm. FIG. 3B shows the mean of the spectra shown in FIG. 3A in depth for each type of particle for a single-layer proton beam of 150 MeV. For primary protons (left), this is modeled as the residual range, whereas for secondary protons (middle) and alpha particles (right) a third-grade polynomial function is used. FIG. 3C shows standard deviation of the spectra shown in FIG. 3A considered as a Gaussian function for a single-layer proton beam of 150 MeV for primary protons (left), secondary protons (middle) and alpha particles (right). Legends: FIG. 3A shows Geant4 simulations (dots), Single Gaussian fits (solid line). FIG. 3B shows mean $\mu_{R,P}$ of the Gaussian function fitted to Geant4 simulations (dots) and Polynomial fits (solid line). FIG. 3C shows sigma $\sigma_{R,P}$ of the Gaussian function fitted to Geant4 simulations (dots), and Polynomial fits (solid line).

Figure 4A:
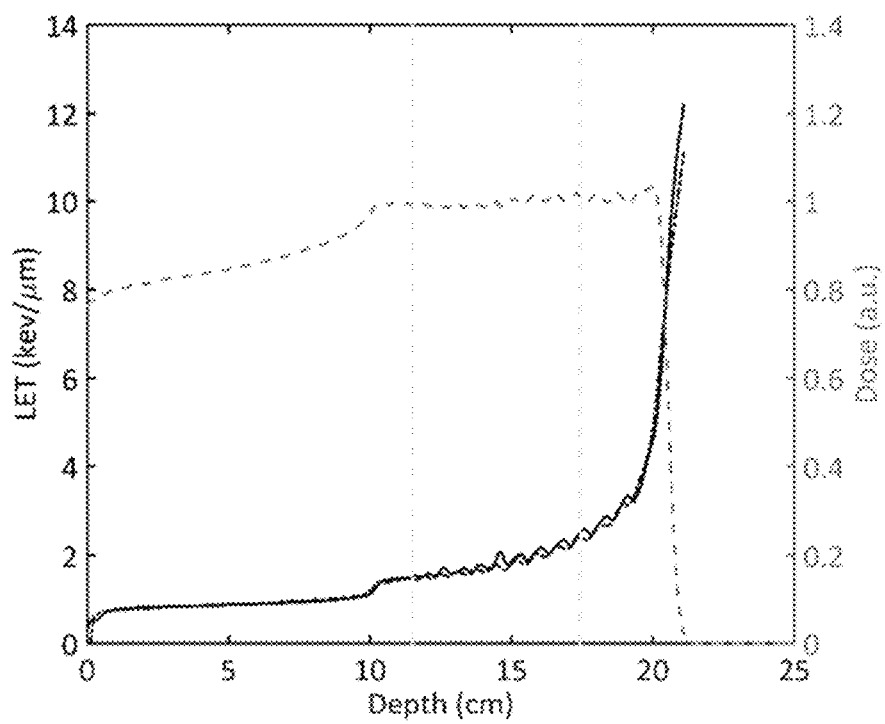
FIG. 4A shows calculated values of LETd along the central axis.
Figure 4B:
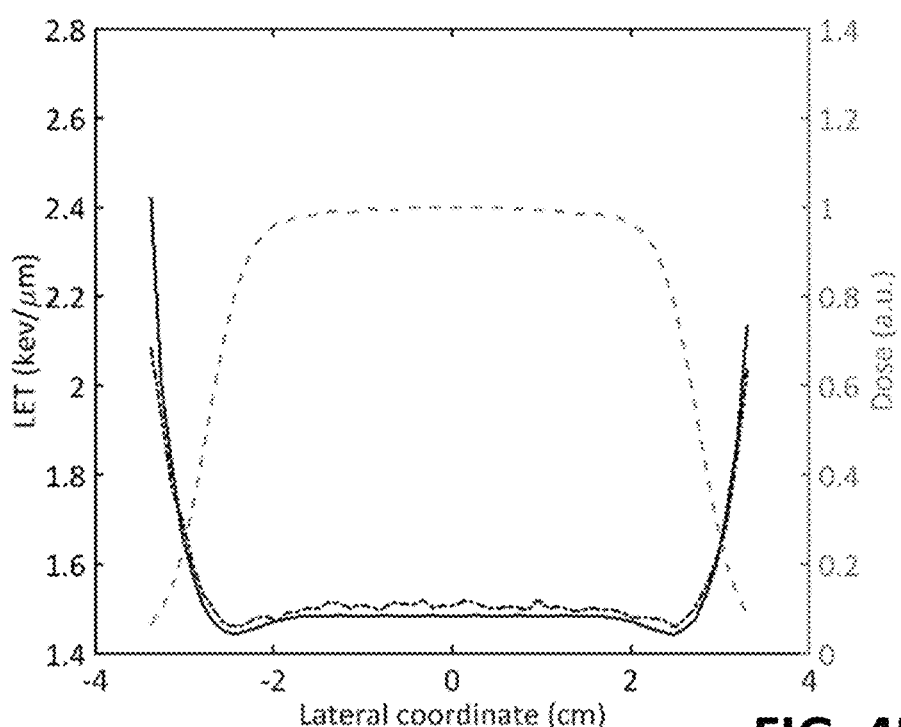
FIG. 4B shows calculated values of LETd along a lateral profile at depth of 11.5 CM.
Figure 4C:
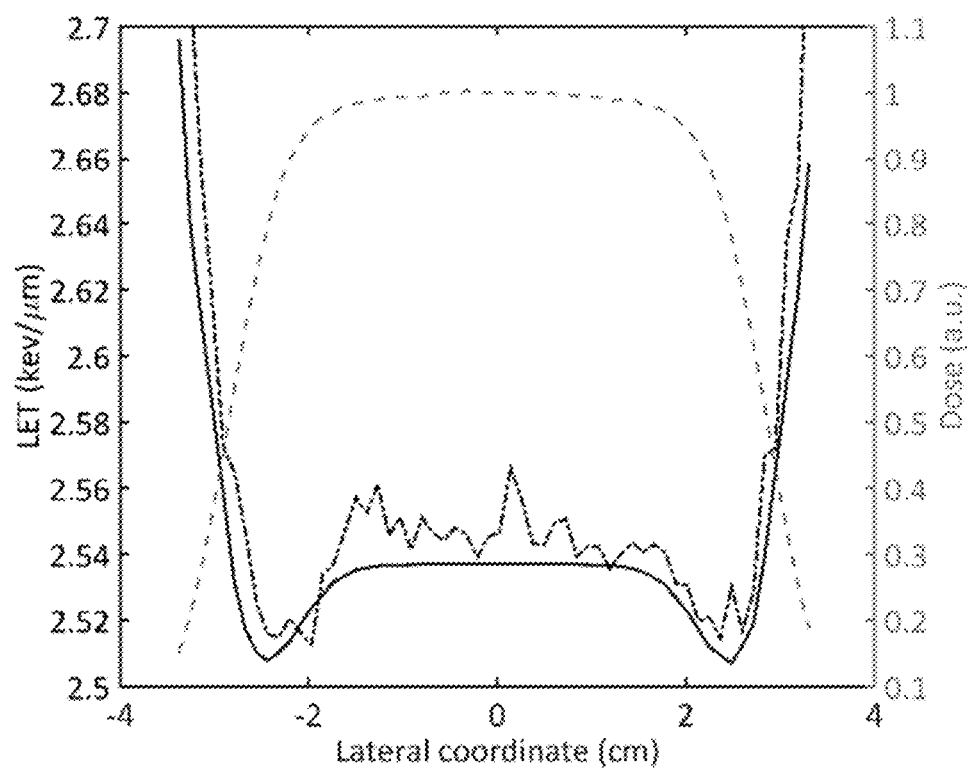
FIG. 4C shows calculated values of LETd along another lateral profile at depth of 17.44 cm.

FIGS. 4A-C shows the comparison between the calculations for LETd by using the fluence kernel method exposed in this work and by MCsquare only considering primary and secondary protons. Results at the central axis are shown in FIG. 4A whereas FIGS. 4B-C show two lateral profiles at different depths. The mean difference between two results along the central axis, taking samples separated by 1 mm, is −0.29±0.15 keV/µm, where uncertainty is expressed as one standard deviation of the mean difference. For the whole three-dimensional distribution, we find a mean difference of −0.007±0.008 keV/µm. Points with a number of particles less than 1% of the total number of particles coming for each layer are excluded from this computation.

FIGS. 4A-C show calculations of LETd considering only protons with our fluence kernel-based method and with MCsquare ($10^9$ protons simulated) for a spread-out Bragg peak with maximum range of 20 cm and 10 cm of modulation at the central axis (FIG. 4A), a lateral profile at depth=11.5 cm (FIG. 4B), and another lateral profile at depth=17.44 cm (FIG. 4C). The positions of the lateral profiles are marked in FIG. 4A with gray vertical lines. Dose calculations with MCsquare are shown in gray dashed lines. Legend: Fluence kernel-based calculation (solid line), and MCsquare (gray dashed lines).

Figure 5A:
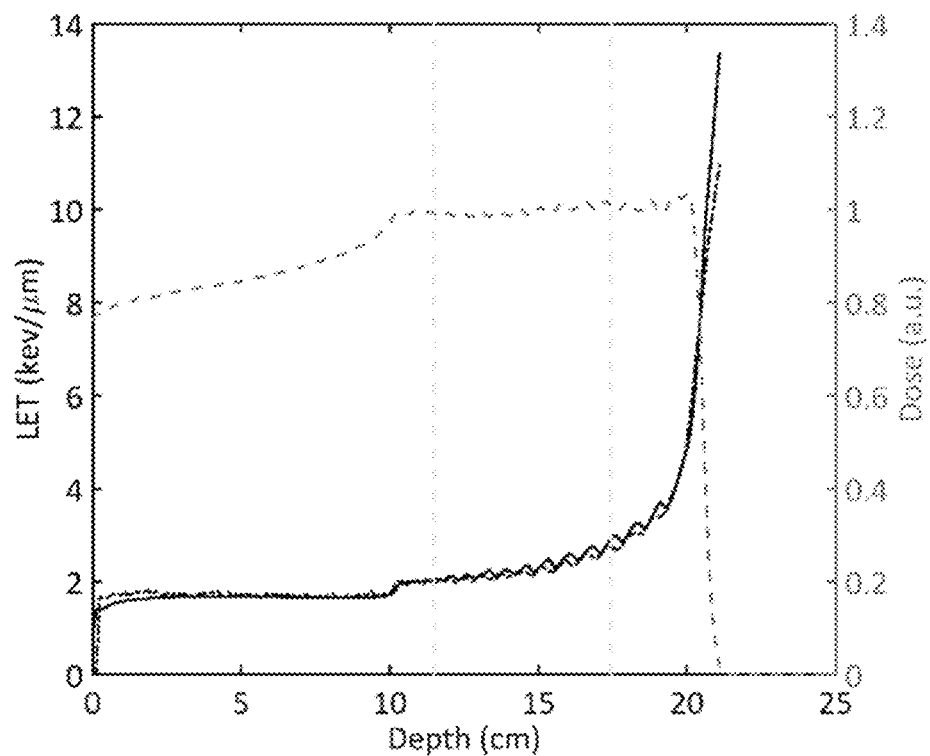
FIG. 5A shows example LETd calculations for a central axis.
Figure 5B:
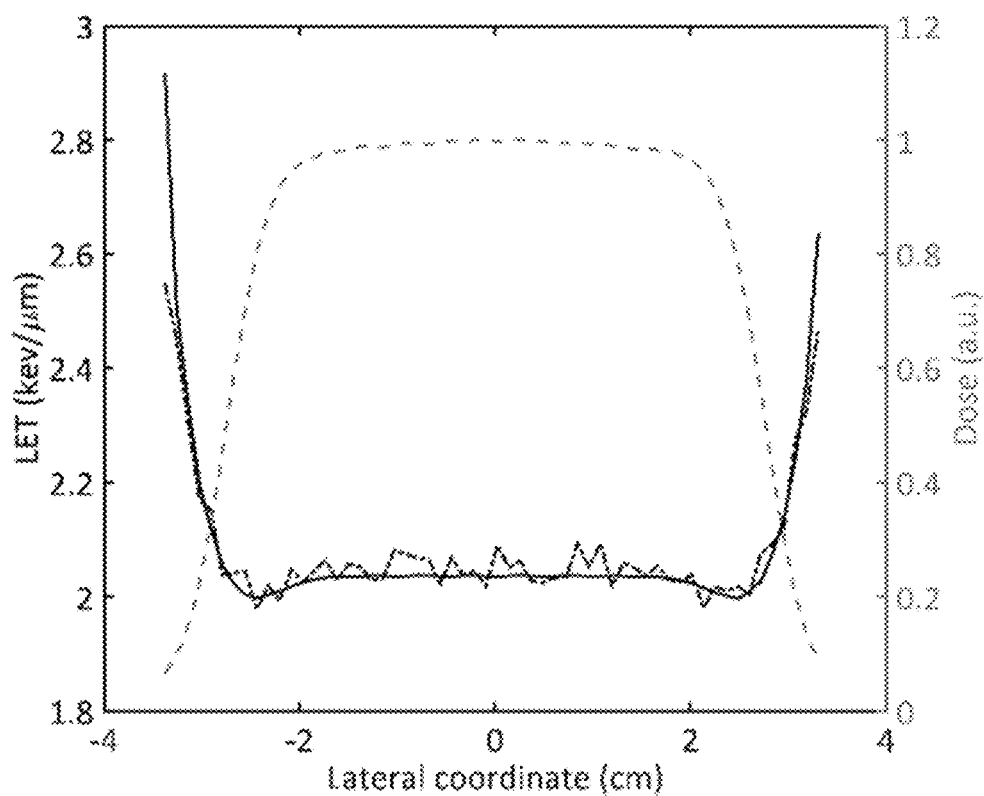
FIG. 5B shows example LETd calculations for a lateral profile at a depth of 11.5 CM.
Figure 5C:
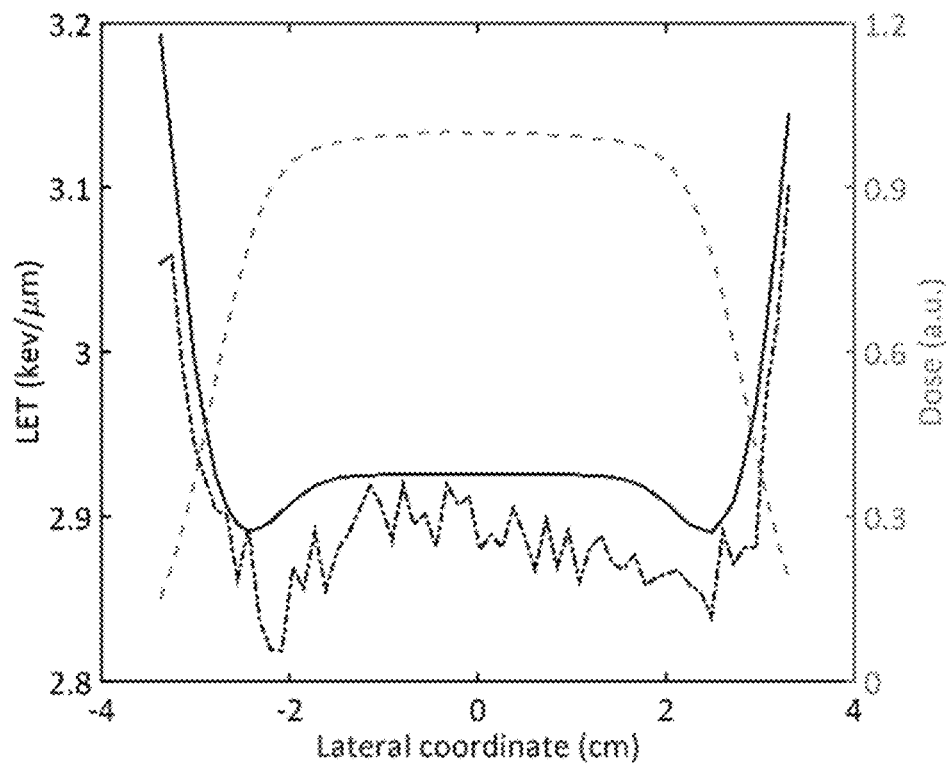
FIG. 5C shows example LETd calculations for another lateral profile at a depth of 17.44 cm.

The same case but adding the alpha particles' contribution to the fluence kernel and all the secondary heavier particles in MCsquare is shown in FIGS. 5A-C. In this case, the mean deviation at the central axis is found as −0.24±0.14 keV/µm, meanwhile for the complete distribution it now goes to −0.022±0.007 keV/µm.

FIGS. 5A-C shows calculations of LETd considering protons and alpha particles with our fluence kernel-based method and a specially compiled version of MCsquare that includes only primary protons, secondary protons and secondary alpha particles ($10^9$ primary particles simulated) for a spread-out Bragg peak with maximum range of 20 cm and 10 cm of modulation. FIG. 5A shows example LETd calculations for a central axis. FIG. 5B shows example LETd calculations for a lateral profile at depth=11.5 cm. FIG. 5C shows example LETd calculations for another lateral profile at depth=17.44 cm. The positions of the lateral profiles are marked in FIG. 5A with gray vertical lines. Dose calculations with MCsquare are shown in gray dashed lines. Legend: Fluence kernel-based calculation (solid line), MCsquare (dashed lines).

Results of the calculations for $\overline{L}_D$ in a prostate case are shown in FIGS. 6A-D. Besides the $\overline{L}_D$ distributions calculated with MCsquare and our method and their differences, dose distribution obtained with MCsquare is also provided to contrast areas in which $\overline{L}_D$ may result high but dose is very low. Mean difference between MCsquare and our method in all the volume irradiated above 5% of the dose is equal to 0.28 keV±0.23 keV/µm. However, for the voxels comprised in the PTV, this mean difference decreases to 0.07±0.11 keV/µm. In the rectum, in turn, mean difference is 0.0±0.8 keV/µm.

Figure 6A:
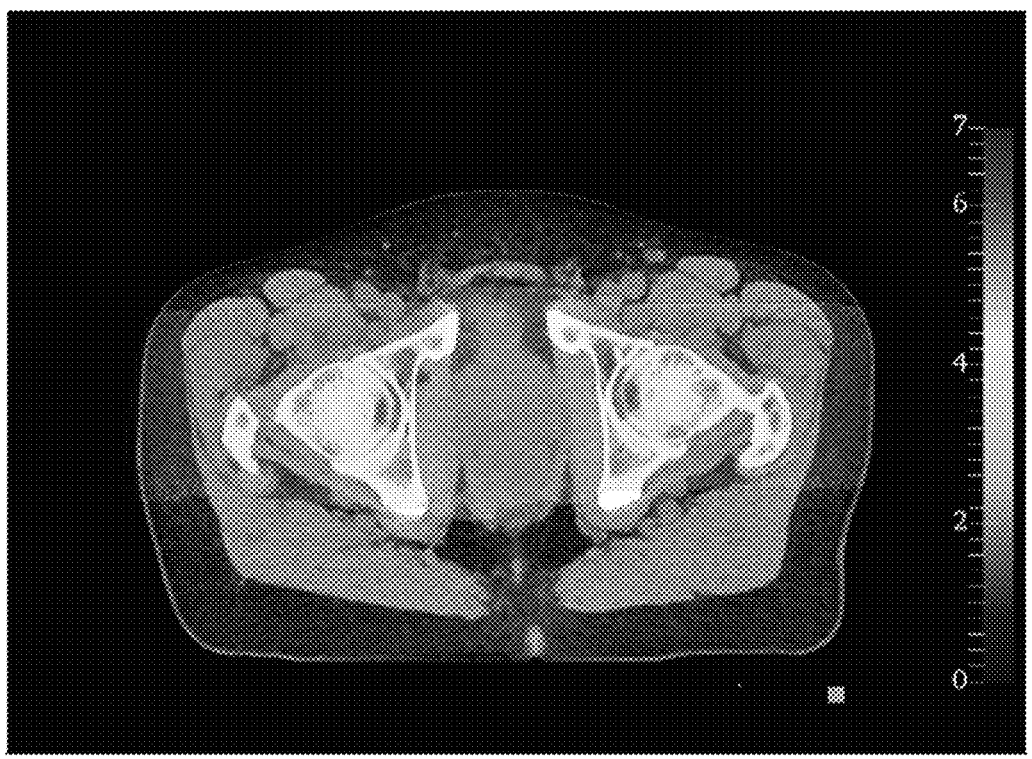
FIG. 6A shows $\overline{L}_D$ calculated with MCsquare.
Figure 6B:
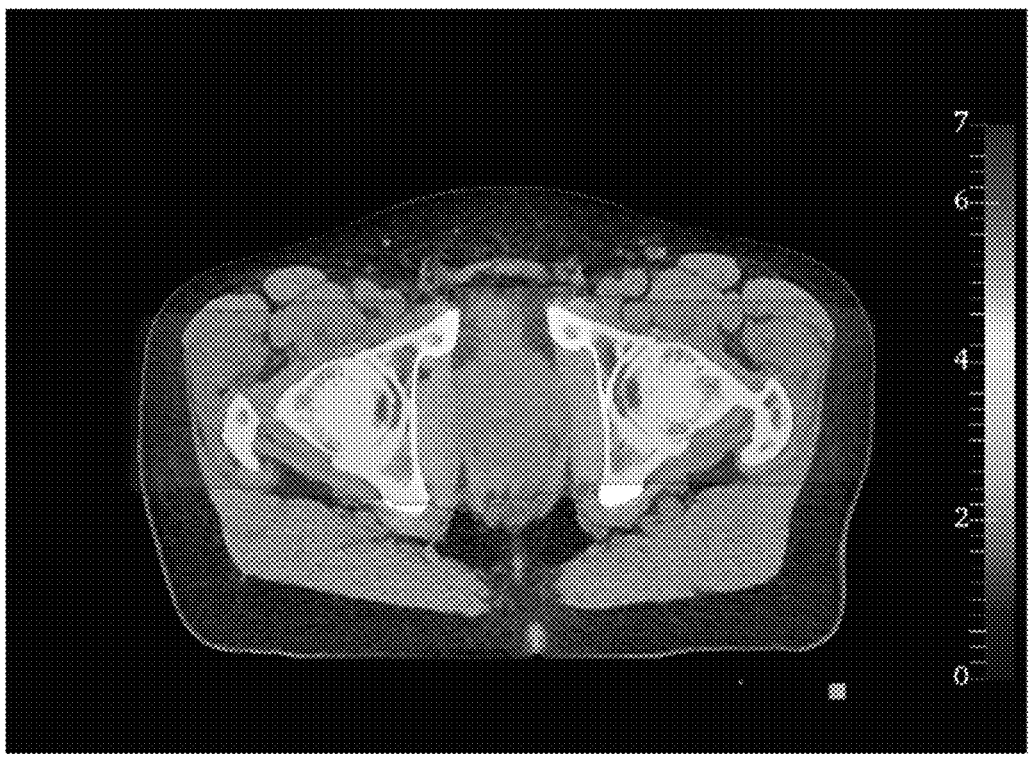
FIG. 6B shows $\overline{L}_D$ calculated the disclosed techniques.
Figure 6C:
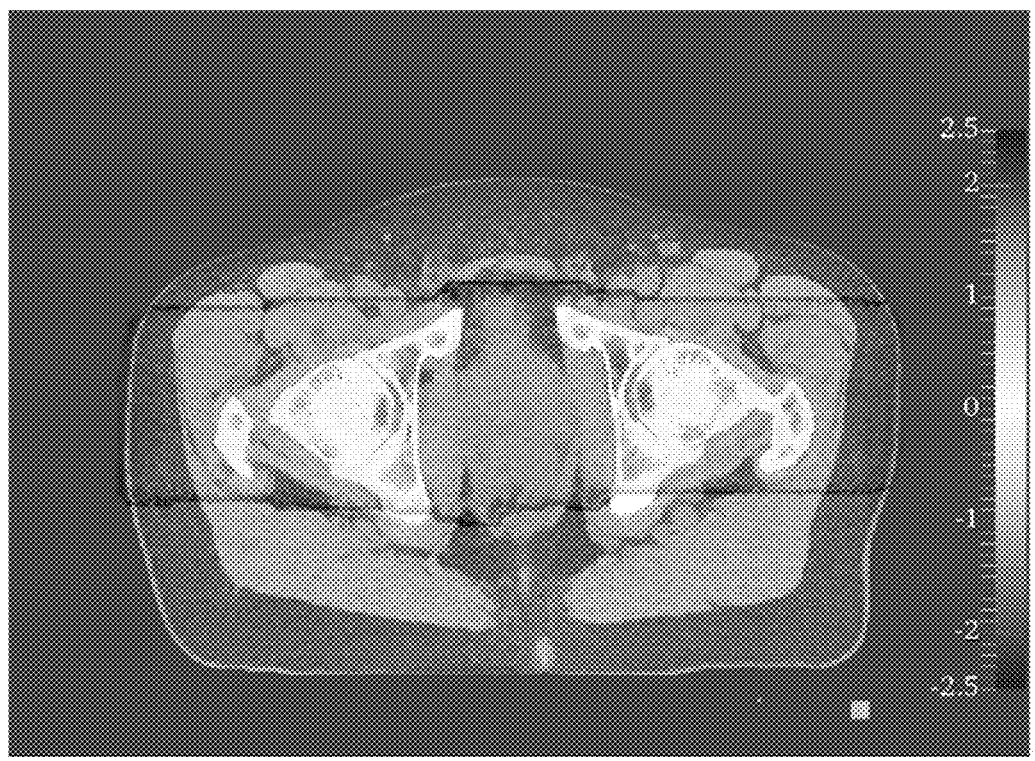
FIG. 6C shows differences between $\overline{L}_D$ calculated with MCsquare and with the disclosed techniques.
Figure 6D:
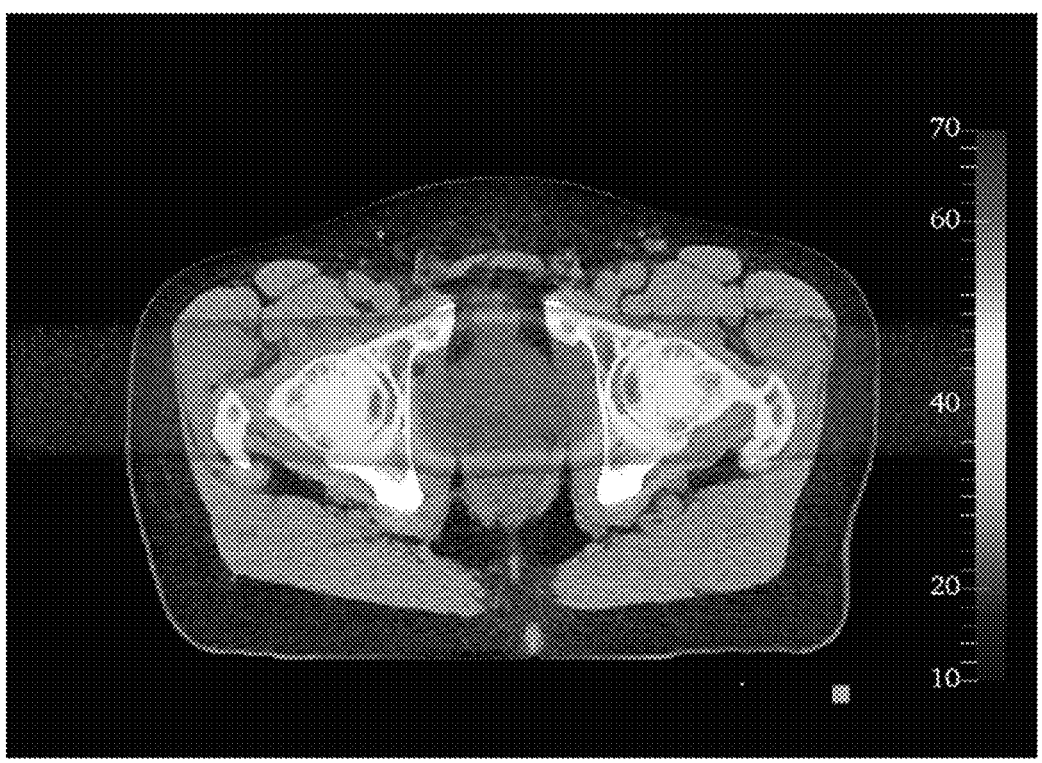
FIG. 6D shows dose distribution calculated with MCsquare.

FIGS. 6A-D show calculations on a central axial plane for prostate case with two lateral beams and a prescribed dose of 70.2 Gy. FIG. 6A shows $\overline{L}_D$ calculated with MCsquare. FIG. 6B shows $\overline{L}_D$ calculated with our method. FIG. 6C shows differences between $\overline{L}_D$ calculated with MCsquare and with our method. FIG. 6D shows dose distribution calculated with MCsquare. For FIGS. A-C, color bars are specified in keV/µm. For FIG. 6D, values on the color bar indicate Gy.

Discussion

Results for LETd calculation show a good performance of our fluence model, especially when only protons are considered (e.g., see FIGS. 4A-C) in which not only central axis profiles tend to coincide but also the characteristic lateral curvature is met at any depth. We have chosen specifically LETd to assess our method for two reasons: (i) the values for the stopping power are extensively validated and (ii) it is a quantity strongly dependent on the spectrum and the relative number of particles from each category rather than on the overall number of particles, which would be the case of quantities as energy or dose absorbed. Because of that dependency, every part of the method can be correctly modeled so that acceptable agreements with MC calculations can be found.

Even though our methodology uses convolution-superposition principles, as pencil beam algorithms do, the main difference here resides in the quantities to be superposed. While dose or LETd-specific kernels directly convolve and superpose curves of those quantities, we sum, on the one hand, the number of particles produced by each beamlet in a spot, and average, on the other hand, the mean energy of the particles traveling in that beamlet. These quantities can naturally be superposed under any condition whereas for dose, some assumptions can be done: the energy deposition can be concentrated close around the particle track. The case of LETd is even worse: the non-linear component on the squared stopping power may not be superposed in this way and artificial workarounds can be incorporated to the lateral kernels.

However, some major deviations from the fluence data computed by Geant4 are observed in some cases. This is especially the case for the number of alpha particles in depth, as seen in FIG. 1C, in which equation (9) appreciably deviates from the curve obtained from Geant4 around the end of the beam range. Nonetheless, the impact of these deviations is reduced since, as protons' stopping power increases in that area, the relative contribution to the LETd of alpha particles becomes small. Our models for secondary protons do not seem accurate at the entrance region (see FIG. 2B and FIG. 3B and FIG. 3C). This can be explained by the small number of secondary protons produced there (e.g., see FIG. 1B), which makes unstable the Gaussian fits and, in turn, makes the values erratic for the parameters. Yet, precisely due to its relatively small number, the weight of these deviations in the calculations is limited. Finally, the relatively low $R^2$ values for the fits of Gaussian functions to the alpha particles are acceptable as a compromise for a simple meaningful function with few parameters, with the mean allowed to vary laterally.

Alpha particles can be included in the disclosed formalism as they represent the main secondary contributor, besides protons, in clinical proton beams. Deuterons, for example, contributes to dose deposition by less than 0.1%, roughly an order of magnitude less than alpha[19]. However, deuterons and other particles might be incorporated following the same methodology to develop kernels for their fluence and spectral fluence. The contribution of alpha particles makes LETd increase especially at the entrance region, although our method seems to slightly underestimate this compared to MCsquare (e.g., see FIGS. 5A-C). However, the general agreement is remarkable and the entrance area is not expected to be particularly relevant to assess biological effect since LETd is relatively low there. In any case, as shown with alpha particles as an example, the contribution of any other particle can be added to the model by following a similar process: (i) obtaining the 3D distributions (number of particles and energy spectrum) for production of that particle in proton beams of a range of energies; (ii) model the functions for the number of particles in depth and laterally; and (iii) model the functions for the spectrum at the central axis and laterally.

It is important to remark that the method to consider inhomogeneous media here presented is a simple displacement of the calculated fluence according to the water-equivalent depth. This may result in errors for the lateral contribution of each beamlet to an adjacent point, especially around edges between two media highly inhomogeneous. Therefore, a more sophisticated method to overcome these situations is desirable. However, as shown in FIGS. 6A-D, average differences in $L_D$ calculation as a surrogate of spectral fluence do not tend to be high, especially in areas in which dose, i.e. fluence, is large.

Only LETd calculations are shown in this work as an example of the potential of this method. It should be noted, though, that an advantage here is the ability to simultaneously calculate a number of QOIs. For instance, if a function for the dependency of the dose on the energy of a particle, $D=D(E)$, can be found, then the same framework can be used to compute dose and LETd, which may lead to an efficient optimization process based on distributions of both quantities. Additionally, as mentioned before, our published microdosimetric functions[11] can be employed in order to generate three-dimensional distributions for them in commercial TPS.

Conclusion

A new analytical method to reproduce the three-dimensional distributions of spectral fluence in particle therapy is disclosed and particularized for the proton therapy case. The advantage of this spectral fluence-based approach is that several quantities of interest can be derived from the spectral fluence by means of a convolution integral as long as the dependency of those with the energy of the involved particles is known. As a specific application, LETd results with this approach look remarkably good even though only protons and alpha particles are taken into consideration. The philosophy of the method includes the potential of extending the considered particles by following a process similar to presented here.

References for Main Text (Above)

1. Hong L, Goitein M, Bucciolini M, et al. A pencil beam algorithm for proton dose calculations. Phys Med Biol. 1996; 41:1305-1330.
2. Soukup M, Fippel M, Alber M. A pencil beam algorithm for intensity modulated proton therapy derived from Monte Carlo simulations. Phys Med Biol. 2005; 50(21): 5089-5104. doi:10.1088/0031-9155/50/21/010
3. Pedroni E, Scheib S, Bohringer T, et al. Experimental characterization and physical modelling of the dose distribution of scanned proton pencil beams. Phys Med Biol. 2005; 50(3):541-561. doi:10.1088/0031-9155/50/3/011
4. Ulmer W. Theoretical aspects of energy-range relations, stopping power and energy straggling of protons. Radiat Phys Chem. 2007; 76(7):1089-1107. doi:10.1016/j.radphyschem.2007.02.083
5. Kimstrand P, Traneus E, Ahnesjo A, Grusell E, Glimelius B, Tilly N. A beam source model for scanned proton beams. Phys Med Biol. 2007; 52(11):3151-3168. doi: 10.1088/0031-9155/52/11/015
6. Wilkens J J, Oelfke U. Analytical linear energy transfer calculations for proton therapy. Med Phys. 2003; 30(5): 806-815. doi:10.1118/1.1567852
7. Marsolat F, De Marzi L, Pouzoulet F, Mazal A. Analytical linear energy transfer model including secondary particles: Calculations along the central axis of the proton pencil beam. Phys Med Biol. 2016; 61(2):740-757. doi: 10.1088/0031-9155/61/2/740
8. Sanchez-Parcerisa D, Cortés-Giraldo M A, Dolney D, Kondrla M, Fager M, Carabe A. Analytical calculation of proton linear energy transfer in voxelized geometries including secondary protons. Phys Med Biol. 2016; 61(4): 1705-1721. doi:10.1088/0031-9155/61/4/1705
9. Hirayama S, Matsuura T, Ueda H, et al. An analytical dose-averaged LET calculation algorithm considering the off-axis LET enhancement by secondary protons for spot-scanning proton therapy. Med Phys. 2018; 45(7):3404-3416. doi:10.1002/mp.12991
10. Bertolet A, Baratto-Roldan A, Barbieri S, Baiocco G, Carabe A, Cortés-Giraldo M A. Dose-averaged LET calculation for proton track segments using microdosimetric Monte Carlo simulations. Med Phys. 2019; 46(9):4184-4192. doi:10.1002/mp.13643
11. Bertolet A, Baratto-Roldan A, Cortés-Giraldo M A, Carabe-Fernandez A. Segment-averaged LET concept and analytical calculation from microdosimetric quantities in proton radiation therapy. Med Phys. 2019; 46(9): 4204-4214. doi:10.1002/mp.13673
12. Berger M J, Coursey J S, Zucker M A, Chang J. Stopping-Power; Range Tables for Electrons, Protons, and Helium Ions|NIST. NIST Standard Reference Database 124. https://www.nist.gov/pml/stopping-power-range-tables-electrons-protons-and-helium-ions. Published 2017. Accessed Dec. 19, 2018.
13. ICRU. Report 90: Key Data for Ionizing Radiation Dosimetry: Measurement Standards and Applications. Vol 14.; 2016.
14. Ulmer W, Matsinos E. Theoretical methods for the calculation of Bragg curves and 3D distributions of proton beams. Eur Phys J Spec Top. 2010; 190(1):1-81. doi: 10.1140/epjst/e2010-01335-7
15. Huang S, Kang M, Souris K, et al. Validation and clinical implementation of an accurate Monte Carlo code for pencil beam scanning proton therapy. J Appl Clin Med Phys. 2018; 19(5):558-572. doi:10.1002/acm2.12420
16. Agostinelli S, Allison J, Amako K, et al. Geant4—a simulation toolkit. Nucl Instruments Methods Phys Res Sect A Accel Spectrometers, Detect Assoc Equip. 2003; 506(3):250-303. doi:10.1016/50168-9002(03)01368-8
17. Allison J, Amako K, Apostolakis J, et al. Geant4 developments and applications. IEEE Trans Nucl Sci. 2006; 53(1):270-278. doi:10.1109/TNS.2006.869826
18. Allison J, Amako K, Apostolakis J, et al. Recent developments in Geant4. Nucl Instruments Methods Phys Res Sect A Accel Spectrometers, Detect Assoc Equip. 2016; 835:186-225. doi:10.1016/J.NIMA.2016.06.125

19. Grassberger C, Paganetti H. Elevated LET components in clinical proton beams. Phys Med Biol. 2011; 56(20): 6677-6691. doi:10.1088/0031-9155/56/20/011
20. ICRU. Report 16. Linear Energy Transfer. Vol 9. Oxford University Press; 1970. doi:10.1093/jicru/os9.1.Report16
21. Varian Medical Systems. Eclipse Scripting API Reference Guide. Version 15.; 2015.
22. Souris K, Lee J A, Sterpin E. Fast multipurpose Monte Carlo simulation for proton therapy using multi- and many-core CPU architectures. Med Phys. 2016; 43(4): 1700-1712. doi:10.1118/1.4943377
23. Cortés-Giraldo M A, Carabe A. A critical study of different Monte Carlo scoring methods of dose average linear-energy-transfer maps calculated in voxelized geometries irradiated with clinical proton beams. Phys Med Biol. 2015; 60(7):2645-2669. doi:10.1088/0031-9155/60/7/2645

ADDITIONAL EXAMPLES

The following examples show additional aspects and applications of the general approach described above. Any of the aspects of the examples below can be combined with each other and/or with the techniques described elsewhere herein.

Example 1: Calculation of Clinical Dose Distributions in Proton Therapy from Microdosimetry Disclosed herein is the introduction of a new algorithm—MicroCalc—for dose calculation by modeling microdosimetric energy depositions and the spectral fluence at each point of a particle beam. Proton beams are considered as a particular case of the general methodology. By comparing the results obtained against Monte Carlo computations, we aim to validate the microdosimetric formalism presented here and in previous works.

In previous works, we developed a function on the energy for the average energy imparted to a microdosimetric site per event and a model to compute the energetic spectrum at each point of the patient image. The number of events in a voxel is estimated assuming a model in which the voxel is completely filled by microdosimetric sites. Then, dose at every voxel is computed by integrating the average energy imparted per event multiplied by the number of events per energy beam of the spectral distribution within the voxel. Our method is compared with the proton convolution superposition (PCS) algorithm implemented in Eclipse™ and the fast Monte Carlo code MCsquare, which is here considered the benchmark, for in-water calculations, using in both cases clinically validated beam data. Two clinical cases are considered: a brain and a prostate case.

For a SOBP beam in water, the mean difference at the central axis found for MicroCalc is of 0.86% against 1.03% for PCS. Three-dimensional gamma analyses in the PTVs compared with MCsquare for criterion (3%, 3 mm) provide gamma index of 95.07% with MicroCalc vs 94.50% with PCS for the brain case and 99.90% vs 100.00%, respectively, for the prostate case. For selected organs at risk in each case (brainstem and rectum), mean and maximum difference with respect to MCsquare dose are analyzed. In the brainstem, mean differences are 0.25 Gy (MicroCalc) vs 0.56 Gy (PCS), whereas for the rectum, these values are 0.05 Gy (MicroCalc) vs 0.07 Gy (PCS).

The accuracy of MicroCalc seems to be, at least, not inferior to PCS, showing similar or better agreement with MCsquare in the considered cases. Additionally, the algorithm enables simultaneous computation of other quantities of interest. These results seem to validate the microdosimetric methodology in which the algorithm is based on.

Introduction

Microdosimetry is the study of the energy deposited by the charged particles in microscopic structures. This framework was originally developed to evaluate the effects of radiation on cells and sub-structures of cells.[1-3] Due to the stochastic nature of the interaction between charged particles, microdosimetry theory deals with the distributions, rather than the deterministic values, of energy imparted to such structures.[4] On the one hand, lineal energy (y) is a microdosimetric quantity, defined as the quotient between the energy imparted to a certain structure, called site, and the mean chord length of the particle in that site.[5] The average of the weighted distribution of this quantity is related to the macroscopic concept of linear energy transfer (LET).[6] Finally, LET is considered as one of the factors impacting the relative biological effectiveness (RBE) for each kind of radiation.[7-9]

On the other hand, specific energy (z) is a different stochastic quantity, defined as the energy imparted to the site divided by the site mass. The average of the microdosimetric distribution of z coincides with the macroscopic concept of absorbed dose.[10] Traditionally, distributions of specific energies for different types of radiation have been applied, for instance, to obtain radiobiological parameters defining the effect of a given test radiation[11] or to characterize the detectors responses.[12] However, it has never been used to calculate three-dimensional (3D) dose distributions in a treatment planning system (TPS) for ion therapy. We present a general methodology to analytically calculate the dose based on the specific energy, particularized to the proton radiotherapy case.

Materials and Methods

Starting from the previous works,[13,14] we have created an analytical model for the dependency of the frequency average of the single-event distribution of specific energy $\bar{z}_F$ on the proton kinetic energy, that is, a function $\bar{z}_F=\bar{z}_F(E)$. The sub-script F indicates frequency average, that is, the average of the frequencies of appearances for each possible specific energy value in a single event. This subscript is traditionally included in contraposition to the dose-weighted average, $\bar{z}_D$, which results from weight each specific energy value for a single event according to the dose imparted during that event. $\bar{z}_F(E)$ can be integrated over the number of events occurred for each proton energy at each point of the calculation grid. Therefore, a dose distribution can be calculated as long as the information of the number of events per energy is known.

Definitions in Microdosimetry Theory

Given a beam of charged particles passing through matter, an event in microdosimetry is the process in which each independent particle track deposits energy by interacting with the atoms of the matter.[15] The event, by definition, includes the depositions of energy from the secondary particles (mainly electrons) generated along the particle track. A site is a subregion of the matter traversed by the radiation beam in which energy deposits are scored. Sites can take different shapes and sizes and allows for characterizing the way in which energy is deposited spatially. The sum of all energy deposits in a site per each independent particle track is called single-event energy imparted, $\varepsilon_s$, and it is a stochastic quantity, whose actual value for each event depends on several factors.[16] Therefore, after a number of events, it is possible to obtain the single-event distribution of energy imparted, in terms of its probability density function, $f(\varepsilon_s)$, by counting the relative frequency of events with each value of energy imparted.

The quotient between the energy imparted $\varepsilon$ after a number of events and the mass m of the site is called specific energy, $z=\varepsilon/m$. Then, the probability density function of the single-event distribution of specific energy, $f_1(z)$ can be obtained from $f(\varepsilon_s)$. The average of the single-event distribution of specific energy is noted by $\bar{z}_F$, where F denotes the frequency. For a given number of events, the specific energy for a site is obtained as the sum of the specific energies at each event. Therefore, as z is also a stochastic quantity, if we consider different series of events, with average v, the distribution of the total specific energy can be expressed in terms of its probability density function, $f(z; v)$. The dose absorbed by the site is not a stochastic quantity and coincides with the average of $f(z; v)$, that is $$D = \int dz f(z;v) = \bar{z} \quad (A1)$$

It is more interesting to consider the distribution of specific energy for a given dose D, $f(z; D)$, rather than in terms of the average number of events v. This distribution gives the probability of obtaining a specific energy z after a series of events when the absorbed dose is D. This distribution can be obtained from the single-event distribution of specific energy, $f_1(z)$, since the interactions between particles and matter can be described by a compound Poisson process.[10] Hence, the absorbed dose can be expressed in terms of the average of the single-event distribution of specific energy as $$D = v\bar{z}_F \quad (A2)$$

Accordingly, if the number of events occurring in a site and the mean specific energy per event are known, it is possible to calculate the corresponding absorbed dose.

Spectral Decomposition

Equation (A2) is valid for any beam regardless its particles or spectrum. However, it is challenging to analytically model $\bar{z}_F$ for such a broad range of possibilities. A good approach consists of considering the single-event distributions of specific energy for monoenergetic beams of energy E, with average $\bar{z}_F = \bar{z}_F(E)$. Then, if the number of events $v(E)$ from particles with energy E is known, the absorbed dose can be calculated as $$D = \int v(E) \bar{z}_F(E) dE \quad (A3)$$

Model for $\bar{z}_F$ (E)

As said above, the single-event specific energy is related to $\bar{\varepsilon}_s$. Equivalently, the average of its single-event distribution is given by $$\bar{z}_F(E) = \frac{\bar{\varepsilon}_s(E)}{m} \quad (A4)$$

The average energy imparted to a site at each particle energy depends on three factors: (a) the stopping power of the particle, (b) how long is the particle track within the site—segment length—, and (c) the probability that secondary electrons generated by the particle leave the site. The trial function for $\bar{\varepsilon}_s(E)$ should be, firstly, proportional to the stopping power, which in turn depends on the particle energy. It also can comprise a term to consider the losses of energy imparted when the range of secondary electrons is larger than the site dimensions. And finally, it can be constrained to decrease as the particle track becomes shorter. In previous works we have explored how to use Monte Carlo simulations to produce microdosimetric data[13] and what functions can be used to characterize the microdosimetric quantities.[14] A function meeting all the referred requirements is:

$$\bar{\varepsilon}_s(E) = C \cdot \mathrm{erf}(kE^q) \cdot \log(h_{P,m}E + b) \cdot \frac{\alpha_{P,m} \cdot E^{(p_{P,m}-1)} + e}{\alpha_{P,m} \cdot E^{p_{P,m}} + 2D_s/3}, \quad (A5)$$

where C, b, and e are free parameters of the function whereas $h_{P,m}$, $\alpha_{P,m}$, and $p_{P,m}$ depend on the considered particle and medium and $D_s$ depends on the site dimension.

The mass of the site can be obtained from its volume and the density of the considered medium. Since dose to water is the quantity normally used in a TPS for dose calculations, the site is considered to be made of liquid water.

Number of Events Per Energy, v(E): A Model for the Voxel-Site Relation

Figure 7:
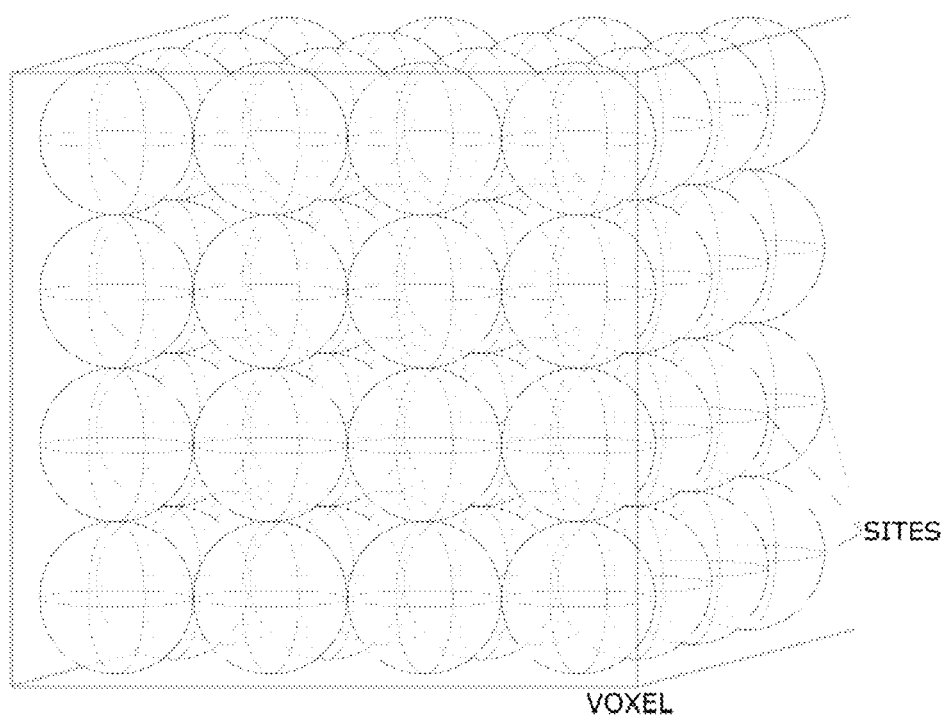
FIG. 7 shows a model for the internal structure of a voxel composed by spherical sites.

By definition, the distribution of average number of events per energy v(E) should coincide with the spectral distribution at the site, that is, the number of particles of each energy impinging on the site. However, we are normally interested in calculating a dose in a voxelized geometry, being the voxel considerably larger than the typical microscopic sites. Therefore, we can firstly consider the number of events occurring in the voxel. For this, we assume the voxel is represented by an arrangement of sites in a rectangular grid, as FIG. 7 shows for the case of spherical sites. Let $N_t$ be the number of sites in the voxel comprised on a layer perpendicular to the particle track, where t stands for transversal. Then, if the transversal cross section of a site is $\sigma_s$, the total cross section in which events are produced is $N_t \sigma_s$ so that the number of events in the voxel is proportional to $\Phi_E(E) N_t \sigma_s$, where $\Phi_E(E)$ is the spectral fluence of particles. Note that this is valid as long as we can assume that the number of indirect events (i.e., produced just by secondary particles) is negligible with respect to the number of direct events (i.e., produced by primary protons), which is expected to be the case for any voxel with dose relevant in radiotherapy.

An additional aspect can be taken into consideration. Let $d_V$ be the dimension of the voxel parallel to the direction of the particle tracks and $d_s$ the maximum dimension of the site in the same direction. Then, the number of sites aligned within the voxel will be $N_l = d_V/d_s$, where l stands for longitudinal. If the incidental particle energy is such that its range is longer than $d_V$, then it will exit the voxel producing an event in each site on its way. Therefore, the number of events will be $v = N_l$. However, if the range of the particle is shorter than $d_V$, the number of events produced by that particle is fewer since the proton stops before reaching the final sites. We assume, in that case, that the number of events produced by that particle is proportional to its CSDA range, R(E), so the number of events in the voxel per energy, $v_V(E)$, is:

$$v_V(E) = \Phi_E(E) N_t \sigma_s \max\left(\frac{d_V}{d_s}, \left\lceil \frac{R(E)}{d_s} \right\rceil \right), \quad (A6)$$

where $\lceil x \rceil$ means the least integer greater than or equal to x, since the number of events is an integer quantity. However, according to Eq. (A2), we are interested in the average number of events per site rather than in the complete voxel. As the total number of sites in the voxel is $N_t N_l$, the average number of events per site is given by $$v(E) = \frac{v_T(E)}{N_t N_l} = \frac{1}{N_l}\Phi_E(E)\sigma_s \max\left(\frac{d_V}{d_s}, \left\lceil\frac{R(E)}{d_s}\right\rceil\right) \quad (A7)$$

A Particular Case: Protons in Spherical Sites

All shown so far remains as valid regardless the particle species, and the site's shape or dimension considered. Now, we introduce a particular case to illustrate the performance of the method. The analysis beyond this point is focused on the proton clinical beams and spherical sites with diameter d. For this specific case, the longitudinal length of the site equals to the site diameter, $d_s$=d, and so it is the site-dependent parameter on the expression for $\bar{\varepsilon}_s$ in Eq. (A5)— $d_s$=d.[14] In order to obtain the rest of parameters in Eq. (A5), we performed simulations with Geant4-DNA[17-20] of monoenergetic protons in spherical sites made of liquid water up to 100 MeV, which is the upper limit the code has for proton transport. To assess the influence of the site dimension in the calculation, we have considered three different cases for the site diameter: 1, 5, and 10 μm. To calculate $\bar{\varepsilon}_s(E)$, for proton energies higher than 100 MeV we assume the validity of Eq. (A5) can be extrapolated to those energies, as our trial function has a smooth behavior at such energies.

Kernel for the Spectral Fluence of Proton Beams

Once $\bar{\varepsilon}_s$, and therefore $\bar{z}_F$, is obtained, the only quantity remaining to be determined is the spectral fluence density, $\Phi_E(E)$. Again, this means the number of protons of each energy per unit area traversing each voxel in which the CT image of a patient is divided. This information can be obtained through Monte Carlo simulations of the proton transport in the patient. Some TPSs are able to provide that information.[21,22] However, we have developed a kernel-based algorithm for the spectral fluence at each point given a proton arriving to the patient surface. Here we provide an outline of this, although it is fully presented in a separate work.[23] Different simulations of the transport of protons in water were carried out by an application based on the Monte Carlo toolkit Geant4.[24-26] Several values for the energy have been selected in the range of clinical use in proton radiotherapy—from 50 MeV up to 250 MeV.

FIG. 7 shows a model for the internal structure of a voxel composed by spherical sites. Protons characterized by a given fluence density impinge on the frontal face of the voxel and particles interact with the row of sites along their track.

A distinction between primary and secondary protons is made to develop independent models for their transport in water. Primary protons are those which only undergo elastic collisions with the atoms of matter meanwhile secondary protons are those coming from inelastic collisions with nuclei. For each one, the model is composed of the following three elements: (a) given an initial fluence of protons $\Phi_0$ penetrating in water, the fraction of primary $\Phi_{PP}(d)/\Phi_0$ and secondary protons $\Phi_{SP}(d)/\Phi_0$ in a whole transversal plane at a given depth d; (b) the lateral distribution of primary $d\phi_{PP}(r; d)/dr$ and secondary protons $d\phi_{SP}(r; d)/dr$ at each depth and each distance r to the central axis of the beam; and (c) the energy spectrum for primary $d\phi_{PP}(E; r, d)/dE$ and secondary $d\phi_{SP}(E; r, d)/dE$ at each lateral position and each depth. For the first case, we use the function proposed in the work of Ulmer[27] for the primary protons, whereas the proportion of secondary protons at each depth $\Phi_{SP}(d)$ is modeled by a phenomenological function[23]:

$$\frac{\Phi_{SP}(d)}{\Phi_0} = (ad - bd^c) \cdot \frac{1}{2}\left(1 + \text{erf}\left(\frac{R(E) - d}{\sqrt{2}\tau}\right)\right), \quad (A8)$$

where a, b, and c are parameters to be fitted dependent on the beam energy, R(E) is the CSDA range corresponding to the initial beam energy and T is the same parameter than used by Ulmer,[27] related to the range straggling of the beam.

For the lateral distribution, we assume that a single Gaussian centered at the beam axis is enough to model the spread in the fluence of primary protons, but not for the secondary ones. Hence, a Double Gaussian is proposed as a better function to model the latter case. Finally, for the sake of simplicity, the energy spectrum for both primaries and secondaries is modeled as a single Gaussian whose mean energy is given by the residual range (i.e., R(E)-d). Then, the kernel of spectral distribution at a voxel with entrance surface dS at the position (d, r) is given by $$\Phi_E^{Kernel}(E; d, r)dS = \sum_{i=PP,SP}\frac{\Phi_i(d)}{\Phi_0}\frac{d\Phi_i(r; d)}{dr}\frac{d\Phi_i(E; r, d)}{dE}dS \quad (A9)$$

where i refers to primary and secondary protons. Note that both $d\Phi_i(r; d)/dr$ and $d\Phi_i(E; r, d)/dE$ are normalized to the unit so that the argument in the summation provides the probability for a proton to have an energy E at the position (d, r). Finally, to obtain the spectral fluence density for a broad beam, it is necessary to convolve two-dimensionally the spectral fluence density of the broad beam coming onto the patient surface, $\Phi_E^{Surface}(E; r)$, with the kernel presented in Eq. (A9):

$$\Phi_E(E; d, r) = \int_E \Phi^{Surface}(E; r')\Phi_E^{Kernel}(E; d, r - r')dr'. \quad (A10)$$

This model for the proton transport only considers liquid water. Transport through other media is here considered by replacing in Eq. (A9) the depth in water, d, by the corresponding water-equivalent thickness $d_{WET}$ resulting from the beam ray tracing.

Dose Distributions Comparisons

All above have been implemented in a script for the Eclipse™ TPS v 15.6 (Varian Medical Systems, Palo Alto, Calif., USA) for Proton Beam Scanning (PBS) treatments, called hereinafter "MicroCalc" or "μCalc." This allows us for producing actual dose calculations in 3D geometries. The TPS provides the information about the beam lateral width—to be convolved with our lateral model. The number of protons prior to arrive to the patient surface can be estimated according to the number of monitor units (MU) for each spot[21] so that we can obtain $\Phi_E^{Surface}(E; r)$. We present comparisons of dose distributions obtained by the: (a) microdosimetric method presented in Eqs. (A3)-(A7) together with the kernel for the proton fluence summarized in Eq. (A9); (b) analytical proton convolution superposition (PCS) algorithm[28] provided by Eclipse; and (c) Monte Carlo simulations with the open source fast MC code MCsquare,[29] which is used as a benchmark in this work as it has been validated elsewhere.[30,31]

We have considered three different situations with different complexities: (a) single energy beams broad enough to provide lateral equilibrium at the central axis, computed in water; (b) a single beam conforming a spread-out Bragg peak (SOBP) with energy layers from 118 to 175 MeV in a water box; and (c) clinical plans for a brain cancer case with three beams and a prostate case with two lateral beams. In the last cases, global 3D gamma analyses in the PTV structures with interpolation are performed to evaluate the differences between analytical methods (MicroCalc and PCS) and the MC calculation (MCsquare) with the MATLAB-based environment OpenREGGUI. The criterion for those gamma analyses is (3%, 3 mm) considering the MCsquare distribution as the reference in all cases. To evaluate the accuracy of the dose calculations in organs at risk, we select an adjacent structure to the PTV in each case to compute the differences with respect to MCsquare—brainstem in the brain case and rectum in the prostate case.

Results

Figure 8:
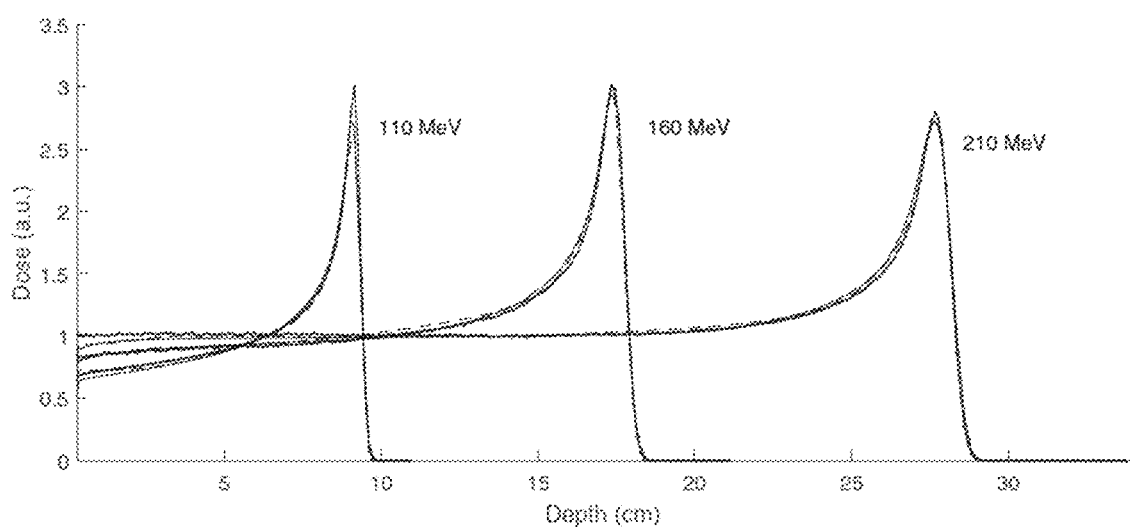
FIG. 8 shows dose profiles for three different beams at central axis for single energy layers of 110, 160, and 210 MeV.

FIG. 8 shows dose profiles for three different beams at central axis for single energy layers of 110, 160, and 210 MeV.

Figure 9:
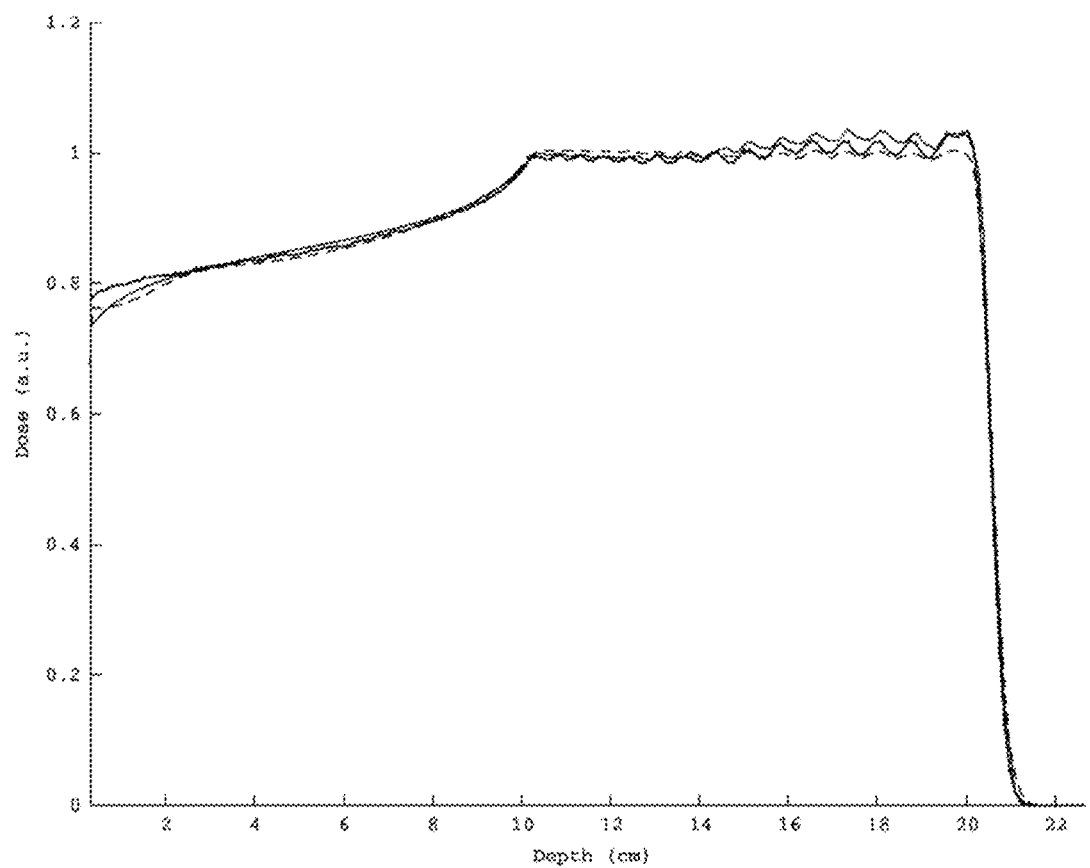
FIG. 9 shows the dose profiles at the central axis for a beam with energy layers from 118 to 175 MeV optimized in Eclipse™ to produce a uniform dose distribution in a target of 10 cm in length and whose distal edge is placed at 20 cm in depth.

FIG. 9 shows the dose profiles at the central axis for a beam with energy layers from 118 to 175 MeV optimized in Eclipse™ to produce a uniform dose distribution in a target of 10 cm in length and whose distal edge is placed at 20 cm in depth. The mean absolute difference along the profile between MCsquare and MicroCalc is 0.86% while the mean difference between MCsquare and PCS algorithm is 1.03%.

Figure 10C:
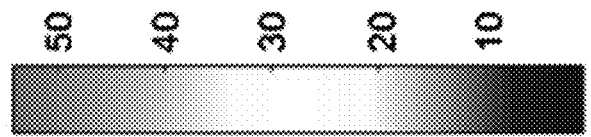
FIG. 10C shows dose distributions for PCS on an axial plane located at the middle of the PTV.
Figure 10C:
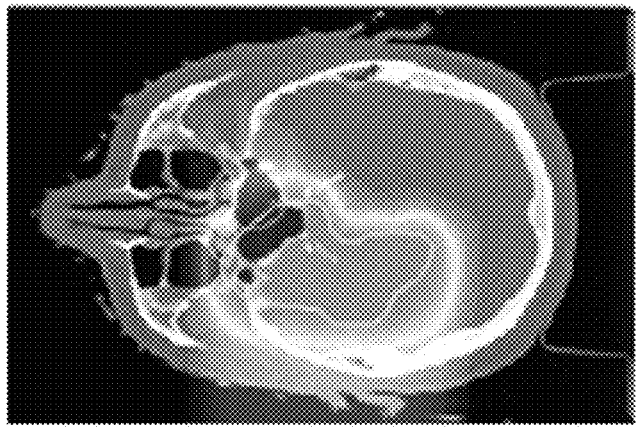
Figure 10B:
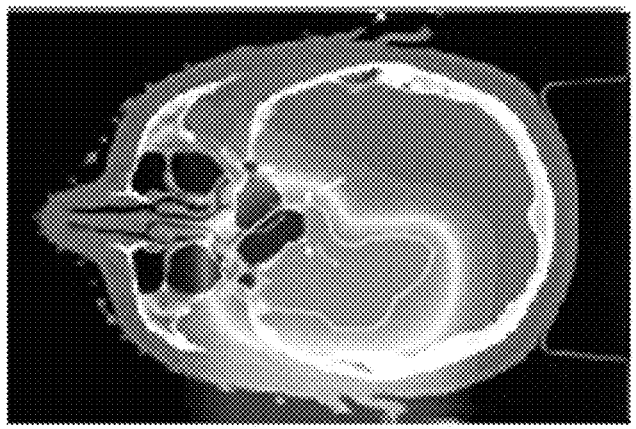
FIG. 10B shows dose distributions for MicroCalc on an axial plane located at the middle of the PTV.
Figure 10A:
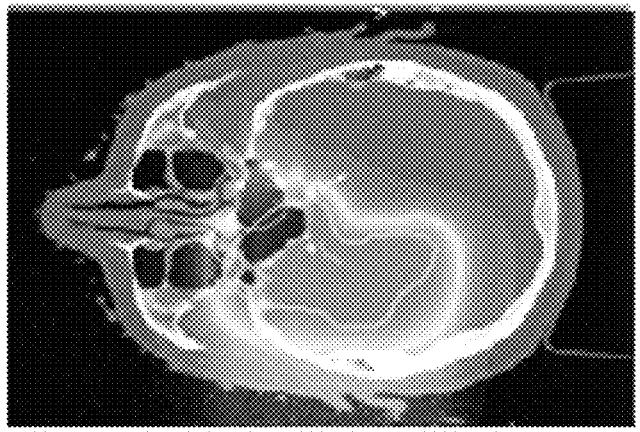
FIG. 10A shows dose distributions for MCsquare on an axial plane located at the middle of the PTV.
Figure 10E:
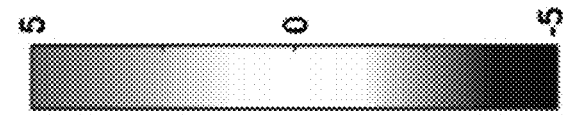
FIG. 10E shows differences between MCsquare and PCS.
Figure 10E:
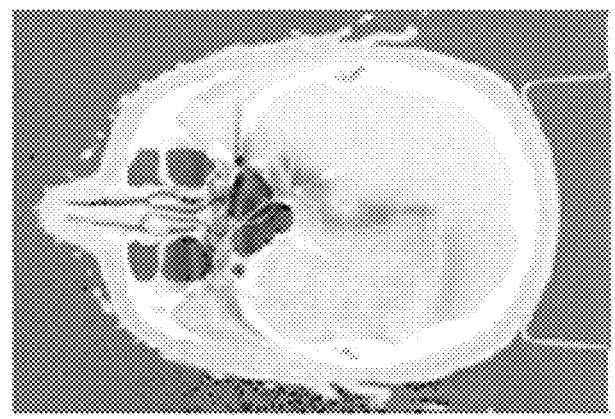
Figure 10D:
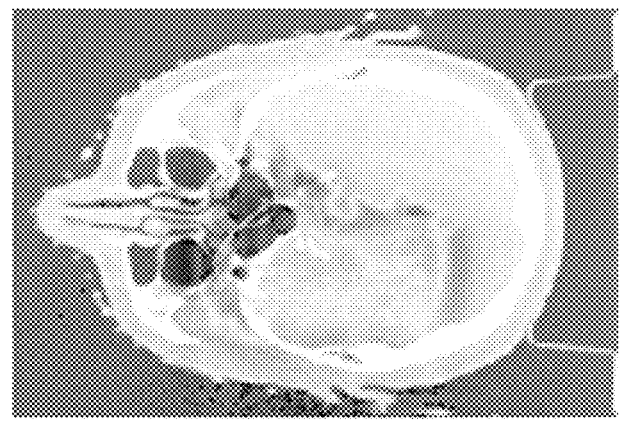
FIG. 10D shows differences between MCsquare and MicroCalc.

A clinical case for brain cancer is shown in FIGS. 10A-E. FIG. 10A shows dose distributions for MCsquare on an axial plane located at the middle of the PTV. FIG. 10B shows dose distributions for MicroCalc on an axial plane located at the middle of the PTV. FIG. 10C shows dose distributions for PCS on an axial plane located at the middle of the PTV. FIG. 10D shows differences between MCsquare and MicroCalc. FIG. 10E shows differences between MCsquare and PCS. 3D gamma analysis with criterion (3 mm, 3%) in the PTV between MicroCalc and MCsquare shows a gamma index of 95.07% while the gamma analysis for differences between PCS and MCsquare is 94.50%. The same procedure in the CTV produces results of 95.10% and 95.03%, respectively. Mean differences in the dose distribution for the brainstem structure are found to be 0.25 Gy between MicroCalc and MCsquare and 0.56 Gy between PCS and MCsquare, respectively.

A similar analysis is shown in FIGS. 11A-E for a prostate case. Results for dose distributions for an axial plane, located at the middle of the PTV are shown for MCsquare, MicroCalc, and PCS calculations, respectively. Again, 3D gamma analysis in the PTV contour with criterion (3%, 3 mm) is performed by comparing MCsquare to MicroCalc and PCS, respectively. The gamma index is 99.90% for the comparison MCsquareMicroCalc and 100% for the comparison MCsquare-PCS. In the rectum, the mean differences in dose between MicroCalc or PCS and MCsquare are 0.05 and 0.07 Gy.

FIG. 8 shows dose profiles at the central axis for single energy layer beams with energies 110, 160, and 210 MeV calculated by employing the MicroCalc script, the proton convolution superposition algorithm in Eclipse™ and the MC code MCsquare. FIG. 8 shows µCalc (solid line); PCS algorithm (dashed line); and MCsquare (dotted line).

Discussion

However, the number of results presented here is not large enough to assess the significance of the goodness for MicroCalc dose calculation, the performance of the proposed model is found comparable to the differences found between MCsquare and the clinically validated algorithm PCS. The ability to reproduce dose ratio between Bragg peak and plateau zone, as well as the beam range, is clearly observable in FIG. 8. When not considering only pristine Bragg peaks, a better agreement with MCsquare is found for MicroCalc at the SOBP than PCS. This better agreement shows up both in the mean difference along the profile at the central axis and the shape of the curve itself, slightly nonuniform as opposed to the PCS algorithm shows. Results shown in FIG. 9 are reproduced in both clinical cases presented (FIGS. 10A-E and 11A-E). Comparable (3%, 3 mm) gamma index is found for the 3D analysis inside the PTV. On the one hand, fewer hot spots are produced beyond that structure for MicroCalc than for PCS, as observable by comparing FIGS. 10A-E and 11D and 11E, even though both analytical algorithms tend to underestimate the dose beyond distal edges. On the other hand, an underestimation of the dose is observed at the penumbra of the beams for both analytical algorithms (e.g., see FIGS. 11D and 11E). However, the beam model employed in Eclipse™ to analytically compute dose uses a single Gaussian to characterize the lateral profile whereas it has been pointed out that might be insufficient to reproduce adequately transversal dose distributions.[32]

FIG. 9 shows dose profiles at central axis for a spread-out Bragg peak with maximum range at 20 cm in depth and modulation of 10 cm calculated by employing the MicroCalc script, the proton convolution superposition (PCS) algorithm in Eclipse™ and the MC code MCsquare. FIG. 9 shows µCalc (solid line), PCS algorithm (dashed line), and MCsquare (dotted line).

FIG. 10A shows dose distributions on an axial plane for a brain case for MCsquare. FIG. 10B shows dose distributions on an axial plane for a brain case for MicroCalc. FIG. 10C shows dose distributions on an axial plane for a brain case for proton convolution superposition (PCS) algorithm. The yellow contour depicts the PTV, with prescription dose of 54 Gy. On the color map, blue color represents low dose (near 0 Gy) while the most intense red color represents 54 Gy. FIG. 10D shows differences between (d) MicroCalc and MCsquare. FIG. 10E shows differences between PCS and MCsquare. In these color maps, the most intense blue shows MCsquare dose is higher by 5 Gy, the most intense red means MCsquare dose is lower by 5 Gy and translucent means no difference.

Figure 11C:
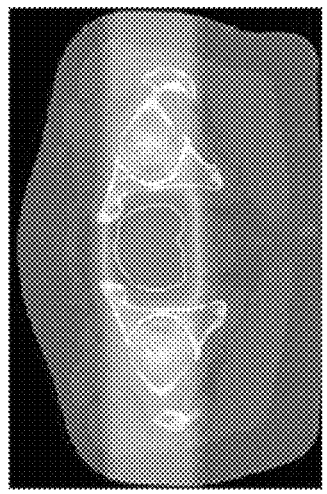
FIG. 11C show dose distributions on an axial plane at the middle of the PTV for a prostate case for proton convolution superposition (PCS) algorithm.
Figure 11B:
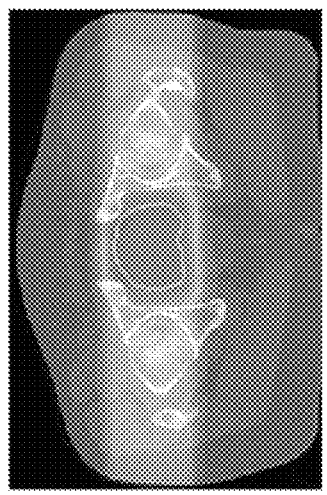
FIG. 11B show dose distributions on an axial plane at the middle of the PTV for a prostate case for MicroCalc.
Figure 11A:
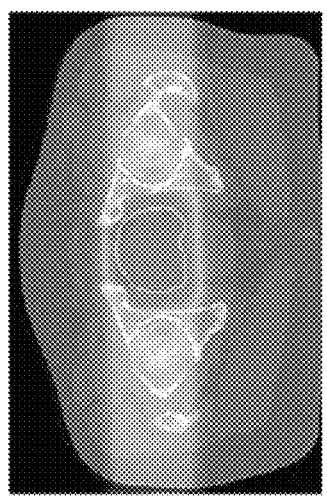
FIG. 11A show dose distributions on an axial plane at the middle of the PTV for a prostate case for MCsquare.
Figure 11E:
FIG. 11E shows differences between PCS and MCsquare.
Figure 11E:
Figure 11D:
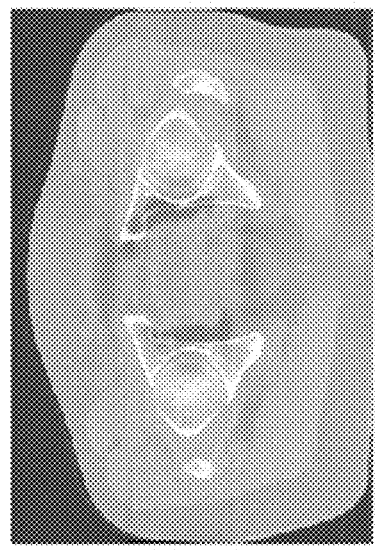
FIG. 11D shows differences between MicroCalc and MCsquare.

FIG. 11A shows dose distributions on an axial plane at the middle of the PTV for a prostate case for MCsquare. FIG. 11B shows dose distributions on an axial plane at the middle of the PTV for a prostate case for MicroCalc. FIG. 11C shows dose distributions on an axial plane at the middle of the PTV for a prostate case for proton convolution superposition (PCS) algorithm. The yellow contour depicts the PTV, with prescription dose of 68 Gy. On the color map, blue color represents low dose (near 0 Gy) while most intense red color represents 68 Gy. FIG. 11D shows differences between MicroCalc and MCsquare. FIG. 11E shows differences between PCS and MCsquare. In these color maps, the most intense blue shows MCsquare dose is lower by 3.5 Gy, the most intense red means MCsquare dose is higher by 3.5 Gy and white means no difference.

As pointed out, the function in Eq. (A5) that characterizes the energy deposition on the proton energy is extrapolated beyond 100 MeV[14] because of the limitation existing in the current version of Geant4-DNA. That lack of actual data for higher energies than this limit is a potential explanation for the observed differences at the entrance with MCsquare in FIG. 9. Besides that, in our current calculations, only protons and alpha particles are considered thus dose coming from heavy particles produced in heavy nuclear interaction is not considered. According to Grassberger and Paganetti,[33] the contribution of those is relatively higher at the entrance so that this effect may also participate on the found differences at that area. An important advantage of MicroCalc is that it allows for incorporating the contributions of different particles independently. This can be done by characterizing the microdosimetric energy depositions in a similar way as for protons.

Even in complex nonhomogeneous cases as shown in FIGS. 10A-E, the dose calculation provided by MicroCalc is able to produce results close to those provided by MCsquare. However, larger inaccuracies may appear when considering greater tissue variabilities along the path beam, as seen at the left posterior cavity in FIG. 10D. Nonetheless, the approach employed to take into consideration lack of homogeneity is relatively simple, that is, only a displacement of the calculated fluence according to the water-equivalent depth. Therefore, a potential improvement in this work consists of implementing a more sophisticated method to overcome the large inhomogeneities situations.

Besides the accuracy of the calculation, at least comparable to other analytical methods, two main reasons make MicroCalc a powerful tool compared to pencil beam algorithms: (a) it can calculate several quantities simultaneously[23] and (b) it is modular, that is different particles can be added independently. Both reasons are based on the idea of trans-porting protons in water while keeping their frequency and spectrum information, which makes MicroCalc closer to actual MC methods. As shown in previous works,[14] not only dose but also 3D distributions of microdosimetric quantities might be obtained in combination with modeled energy-dependent functions in a similar way than shown here. Furthermore, other macroscopic quantities as dose-averaged LET can be also calculated[23] based on stopping power curves, and even combinations of all those functions for optimization purposes (e.g., dose-LET product) may be computed in a straightforward way.

Conclusions

A new analytical algorithm—MicroCalc—to calculate dose is explicitly introduced and detailed in this work. The accuracy of this method is, at least, not inferior to the proton convolution superposition (PCS) algorithm, already clinically validated in Eclipse™. This seems to corroborate the methodology employed in this work as well as, partially the microdosimetric functions developed in our previous work.[14] Also, MicroCalc provides the possibility of separating different particles contributions and simultaneously computing several quantities of interest, which conceptually makes it similar to Monte Carlo techniques.

References for Example 1

1. Rossi H H. Spatial distribution of energy deposition by ionizing radiation source. *Radiat Res.* 1960; 2:290-299.
2. Rossi H H. Microdosimetry. Biophys Asp Radiat Qual IAEA, Tech Reports Ser; 1966:58.
3. Kellerer A M, Rossi H H. The theory of dual radiation action. In: Ebert M, Howard A, eds. *Current Topics in Radiation Research.* Vol. VIII. Manchester, UK: American Elsevier Publishing Company; 1974:85-156.
4. Kellerer A M, Chmelevsky D. Concepts of microdosimetry—II. Probability distributions of the microdosimetry variables. *Radiat Environ Biophys.* 1975; 12:205-216.
5. Kellerer A M, Chmelevsky D. Concepts of microdosimetry—I. Quantities. *Radiat Environ Biophys.* 1975; 12:61-69.
6. Kellerer A M, Chmelevsky D. Concepts of microdosimetry—III. Mean values of the microdosimetric distributions. *Radiat Environ Biophys.* 1975; 12:321-335.
7. Belli M, Cera F, Cherubini R, et al. RBE-LET relationships for cell inactivation and mutation induced by low energy protons in V79 cells: further results at the LNL facility. *Int J Radiat Biol.* 1998; 74:501-509.
8. Hawkins R B. A microdosimetric-kinetic model for the effect of non-poisson distribution of lethal lesions on the variation of RBE with LET. *Radiat Res.* 2003; 160:61-69.
9. Barendsen G W. The relationships between RBE and LET for different types of lethal damage in mammalian cells: biophysical and molecular mechanisms. *Radiat Res.* 1994; 139:257-270.
10. Kellerer A M. Fundamentals of microdosimetry. In: Kase K R, Bjarngard B E, Attix F H, eds. *The Dosimetry of Ionization Radiation*, Vol. I. Cambridge: Academic Press Inc; 1985:77-162.
11. Rossi H H, Zaider M. *Microdosimetry and Its Applications.* Berlin: Springer; 1996.
12. Olko P. The microdosimetric one-hit detector model for calculating the response of solid state detectors. *Radiat Meas.* 2002; 35:255-267.
13. Bertolet A, Baratto-Roldan A, Barbieri S, Baiocco G, Carabe A, Cortés-Giraldo M A. Dose-averaged LET calculation for proton track segments using microdosimetric Monte Carlo simulations. *Med Phys.* 2019; 46:4184-4192.
14. Bertolet A, Baratto-Roldan A, Cortés-Giraldo M A, Carabe-Fernandez A. Segment-averaged LET concept and analytical calculation from microdosimetric quantities in proton radiation therapy. *Med Phys.* 2019; 46:4204-4214.
15. ICRU. Report 36. Microdosimetry; 1983.
16. Kellerer A M. Analysis of patterns of energy deposition. In: Ebert H G, ed. *Second Symposium on Microdosimetry.* Stresa, Italy: Commission of the European Communities; 1970:107-136.
17. Incerti S, Baldacchino G, Bernal M, et al. The Geant4-DNA project. *Int J Model Simul Sci Comput.* 2010; 1:157-178.
18. Incerti S, Ivanchenko A, Karamitros M, et al. Comparison of GEANT4 very low energy cross section models with experimental data in water. *Med Phys.* 2010; 37:4692-4708.
19. Bernal M A, Bordage M C, Brown J M C, et al. Track structure modeling in liquid water: a review of the Geant4-DNA very low energy extension of the Geant4 Monte Carlo simulation toolkit. *Phys Medial.* 2015; 31:861-874.
20. Incerti S, Kyriakou I, Bernal M A, et al. Geant4-DNA example applications for track structure simulations in liquid water: a report from the Geant4-DNA Project. *Med Phys.* 2018; 45:e722-e739.
21. Lin L, Huang S, Kang M, et al. A benchmarking method to evaluate the accuracy of a commercial proton monte carlo pencil beam scanning treatment planning system. *J Appl Clin Med Phys.* 2017; 18:44-49.
22. Saini J, Maes D, Egan A, et al. Dosimetric evaluation of a commercial proton spot scanning Monte-Carlo dose algorithm: comparisons against measurements and simulations. *Phys Med Biol.* 2017; 62: 7659-7681.
23. Bertolet A, Cortés-Giraldo M A, Souris K, Carabe-Fernandez A. A kernel-based algorithm for fluence and spectral fluence in clinical proton beams to calculate dose-averaged LET and other dosimetric quantities of interest. *Med Phys* [SUBMITTED]. 2019.
24. Agostinelli S, Allison J, Amako K, et al. Geant4a simulation toolkit. *Nucl Instruments Methods Phys Res Sect A.* 2003; 506:250-303.
25. Allison J, Amako K, Apostolakis J, et al. Geant4 developments and applications. *IEEE Trans Nucl Sci.* 2006; 53:270-278.

26. Allison J, Amako K, Apostolakis J, et al. Recent developments in Geant4. *Nucl Instruments Methods Phys Res Sect A*. 2016; 835:186-225.
27. Ulmer W. Theoretical aspects of energy-range relations, stopping power and energy straggling of protons. *Radiat Phys Chem*. 2007; 76:1089-1107.
28. Varian. Eclipse Proton Algorithms Reference Guide, v 13.7. 2015.
29. Souris K, Lee J A, Sterpin E. Fast multipurpose Monte Carlo simulation for proton therapy using multi- and many-core CPU architectures. *Med Phys*. 2016; 43:1700-1712.
30. Sorriaux J, Testa M, Paganetti H, et al. Experimental assessment of proton dose calculation accuracy in inhomogeneous media. *Phys Medica*. 2017; 38:10-15.
31. Huang S, Kang M, Souris K, et al. Validation and clinical implementation of an accurate Monte Carlo code for pencil beam scanning proton therapy. *J Appl Clin Med Phys*. 2018; 19:558-572.
32. Bellinzona V E, Ciocca M, Embriaco A, et al. On the parametrization of lateral dose profiles in proton radiation therapy. *Phys Medial*. 2015; 31:484-492.
33. Grassberger C, Paganetti H. Elevated LET components in clinical proton beams. *Phys Med Biol*. 2011; 56:6677-6691.

Example 2: On the Concepts of Dose-Mean Lineal Energy, Unrestricted and Restricted Dose-Averaged LET in Proton Therapy Disclosed herein are techniques for calculating 3D distributions of microdosimetric-based restricted dose-averaged LET (LETd) and dose-mean lineal energy ($y_D$) in order to explore their similarities and differences between each other and with the traditional unrestricted LETd. Additionally, a new expression for optimum restricted LETd calculation is derived, allowing for disregarding straggling-associated functions in the classical microdosimetric theory.

Restricted LETd and $y_D$ for polyenergetic beams can be obtained by integrating previously developed energy-dependent microdosimetric functions over the energetic spectrum of these beams. This calculation is extended to the entire calculation volume using an algorithm to determine spectral fluence. Equivalently, unrestricted LETd can be obtained integrating the stopping power curve on the spectrum. A new expression to calculate restricted LETd is also derived. Results for traditional and new formulas are compared for a clinical 100 MeV proton beam. Distributions of unrestricted LETd, restricted LETd and $y_D$ are analyzed for a prostate case, for microscopic spherical sites of 1 µm and 10 µm in diameter.

Traditional and new expressions for restricted LETd remarkably agree, being the mean differences 0.05±0.04 keV/µm for the 1-µm site and 0.05±0.02 keV/µm for the 10-µm site. In the prostate case, the ratio between the maximum and the central value for central axis (CAX) profiles is around 2 for all the quantities, being the highest for restricted LETd for 1 µm (2.17) and the lowest for $y_D$ for 1 µm (1.78).

Unrestricted LETd, restricted LETd and $y_D$ can be analytically computed and compared for clinical plans. Two important consequences of the calculation of $y_D$ are: 1) its distribution can be verified by directly measuring it in clinical beams; and 2), optimization of proton treatments based on these quantities is enabled as well as future developments of RBE models based on them.

Introduction

The importance of the biophysical properties of proton therapy beams have been substantially considered due to the variability of the relative biological effectiveness (RBE)[1,2] and its potential clinical consequences. The use of intensity modulated techniques in proton therapy (IMPT) is becoming the standard of care, and these types of techniques produce non-homogeneous dose-averaged LET (LETd) distributions[3] that have been shown to be correlated with clinical outcomes[4]. While the large variability of RBE in vitro experiments makes its determination, in general, indistinguishable from its associated uncertainty, LETd is a physical quantity accurately computable[5,6] and directly correlated with RBE. This correlation may lead to a practical biophysical optimization of proton therapy treatments[7-15].

The concept of LETd, nonetheless, comprises some simplifications and disregards relevant aspects of the patterns of energy imparted in matter. LETd is traditionally calculated by employing data for collision stopping power or unrestricted LET[16-19], which is defined as the mean energy lost by the proton in electronic collision processes per unit path length[20]. Nevertheless, to better characterize the concentration or density of energy deposition in biological structures, energy carried out away from them should be taken off this computation. In this context, the concept of restricted LET, $L_\Delta$ arises, normally defined by using a threshold kinetic energy for secondary delta-rays, $\Delta$, above which those are disregarded[20]. However, in this work the restriction is defined spatially as explained below.

By using the microdosimetry formalism[21,22] and the concept of site, spatially-restricted LETd can be calculated. Furthermore, the microdosimetric concept of lineal energy (y) and its equivalent version of LETd, called dose-mean lineal energy ($y_D$) might better represent microscopic distribution of the energy depositions since they comprise the information of the imparted energy patterns in small volumes instead of per track length as done with the macroscopic concept of LET. In this sense, $y_D$ has been also related to RBE by means of the Microdosimetric-Kinetic Model (MKM)[23,24] and their subsequent modifications[25,36]. In fact, efforts have lately been put to establish this connection[27,28] and enable the biophysical optimization of proton radiotherapy treatments in terms of $y_D$. Nevertheless, determination of $y_D$ in clinical cases would require extremely lengthy Monte Carlo (MC) simulations down to microscopic level, which has made its use impractical so far.

In previous articles, we have presented models to calculate microdosimetric quantities such as $y_D$ and restricted LETd in monoenergetic beams[29]. Independently, we have developed and introduced an analytical algorithm to determine the energetic spectrum for proton therapeutic beams in each voxel inside a calculation volume within a patient[30]. Here, we combine these two works to produce distributions of restricted LETd and $y_D$ in clinical proton therapy cases. This has led us to propose a simplified and optimized expression for restricted LETd. Analogies and differences between distributions of unrestricted LETd, restricted LETd and $y_D$ are here explored.

Methods and Materials

In order to clarify the notation employed throughout this work and make the reading easier, Table 1 shows a list of relevant variables, their symbols and their nature. For LETwise quantities, the combination of the subscripts here shown combine their nature: for example, $L_{\Delta,D}$ is the dose-average spatially restricted linear energy transfer.

TABLE 1

| Symbol | Quantity | Nature |
| --- | --- | --- |
| $\varepsilon_s$ | Energy imparted per event | Stochastic (event-wise) |
| $\bar{\varepsilon}_s$ | Mean energy imparted per event | Average of distribution of $\varepsilon_s$ per event |
| $\sigma_{\varepsilon_s}^2$ | Variance of the energy imparted per event | Variance of distribution of $\varepsilon_s$ per event |
| $s$ | Segment length for an event | Stochastic (event-wise) |
| $\bar{s}$ | Mean segment length | Average of distribution of $s$ per event |
| $\bar{s}_D$ | Weighted-average segment length | Weighted average of distribution of $s$ per event |
| $y$ | Lineal energy for an event | Stochastic (event-wise) |
| $\bar{y}_D$ | Dose-mean lineal energy | Weighted average of distribution of $y$ per event |
| $\varepsilon_c$ | Energy imparted per collision | Stochastic (collision-wise) |
| $\bar{\varepsilon}_c \equiv \delta_1$ | Mean energy imparted per collision | Average of distribution of $\varepsilon_c$ per collision |
| $\delta_2$ | Weighted-average energy imparted per collision | Weighted average of distribution of $\varepsilon_c$ per collision |
| $S(E)$ | Stopping power for protons of energy $E$ | Function of proton energy |
| $\bar{\varepsilon}_s(E)$ | Mean energy imparted per event for protons of energy $E$ | Function of proton energy |
| $\sigma_{\varepsilon_s}^2(E)$ | Variance of the energy imparted per event for protons of energy $E$ | Function of proton energy |
| $\phi_E(E)$ | Differential spectrum for a beam: distribution of particles with energy $E$ | Distribution per proton energy |
| $\overline{\bar{\varepsilon}_s} \equiv \overline{\bar{\varepsilon}_s(E)}$ | Average of mean energy imparted per event for a polyenergetic beam | Average of distribution of $\bar{\varepsilon}_s$ per proton energy |
| $\overline{\sigma_{\varepsilon_s}^2} \equiv \overline{\sigma_{\varepsilon_s}^2(E)}$ | Average of the variance of the energy imparted per event for protons of energy $E$ | Average of distribution of $\sigma_{\varepsilon_s}^2$ per proton energy |
| $\sigma_{\bar{\varepsilon}_s}^2 \equiv \sigma_{\bar{\varepsilon}_s}^2(E)$ | Variance of the mean energy imparted per event | Variance of distribution of $\bar{\varepsilon}_s$ per proton energy |
| $\bar{L}_T$ | Track-average linear energy transfer | Average of distribution of LET per particle |
| $\bar{L}_D$ | Dose-average linear energy transfer | Weighted average of distribution of LET per particle |
| $L_\infty$ | Unrestricted linear energy transfer | Deterministic |
| $L_\Delta$ | Spatially restricted linear energy transfer | Deterministic |

LET and its Relation with Microdosimetry

A site is a certain region of interest, with a given shape and size, in a particular medium in which the energy imparted by a particle in its electronic collisions is scored. Each incident charged heavy particle has a defined track, composed of its trajectory as well as those for the secondary electrons generated along its way. An interaction between a track and a site is called event. The amount of energy imparted to the site in a single event is notated by $\varepsilon_s$. This is a stochastic quantity, i.e. it varies from event to event even when the experimental conditions are the same. Therefore, $\varepsilon_s$ is characterized by a probability distribution $f(\varepsilon_s)$, with certain mean value $\bar{\varepsilon}_s$ and variance $\sigma_{\varepsilon_s}^2$, which provides a measurement of the variability for the value of $\varepsilon_s$ in an experiment. The variability on $\varepsilon_s$ is influenced by three sources[21]: (i) the variability on the average energy imparted per unit length, characterized by means of the linear energy transfer (LET), that represents the ability of the particle to interact with the medium (i.e. interaction cross section); (ii) the variability on the segment length s, which is the distance travelled by the particle within the site[29]; and (iii) the energy straggling, i.e. given an average energy imparted per unit length, the variability on the number of collisions and energy deposited in them due to stochastic nature of interactions between radiation and matter.

The quotient between the energy imparted in a single event $\varepsilon_s$ and the mean segment lengths $\bar{s}$ of tracks in the site is called lineal energy:

$$y = \frac{\varepsilon_s}{\bar{s}} \tag{B1}$$

Consequently, lineal energy is also a stochastic quantity, characterized by a distribution $f(y)$ that includes information about the volumetric pattern of energy deposition. However, the deterministic concept of LET is generally employed instead, since it allows for a more simplistic approach in which track structure can be disregarded. In this context, when dealing with a polyenergetic or multi-particle beam, a distribution of different values for LET arises. In such a situation, it has been shown[31] that for typical doses in proton therapy the dose-weighted average or dose-averaged LET, $\bar{L}_D$, is more representative of the biological effect than the simple average LET, traditionally called track-averaged or fluence-averaged LET, $\bar{L}_T$. To clarify notation employed hereinafter, any weighted-average of stochastic quantity x with distribution $f(x)$ is notated by the subscript D. In other words, $\bar{x}_D$ represents the weighted-average for any stochastic quantity x. For further identification of each variable, see Table 1. Dose-averaged restricted LET is related to dose-mean lineal energy $\bar{y}_D$ by[29]

$$\bar{L}_{\Delta,D} = \frac{\bar{s}}{\bar{s}_D}\bar{y}_D - \frac{\delta_2}{\bar{s}_D} \quad (B2)$$

where $\bar{s}$ and $\bar{s}_D$ are the average and the weighted average of the distribution of segment length, respectively, and $\delta_2$ is the weighted average of the distribution of the energy imparted per electronic collision $\varepsilon_c$.[32] Additionally, the subscript $\Delta$ is added to $\bar{L}_D$ to indicate that, by using this formalism, the obtained LET is restricted to a site dimension noted by $\Delta$.

In previous works, we have developed analytical functions on the proton energy for the averages and variances of the microdosimetric distributions[29]. By using these functions, the mean energy imparted, and the variance of the energy imparted for a polyenergetic proton beam $\sigma_{\varepsilon_s,\phi}^2$ can be obtained, respectively, as $$\bar{\varepsilon}_s = \frac{\int \bar{\varepsilon}_s(E)\phi_E(E)dE}{\int \phi_E(E)dE} \quad (B3)$$

and $$\sigma_{\varepsilon_s,\phi}^2 = \frac{\int \sigma_{\varepsilon_s}^2(E)\phi_E(E)dE}{\int \phi_E(E)dE} + \frac{\int (\bar{\varepsilon}_S(E) - \bar{\varepsilon}_S)^2 \phi_E(E)dE}{\int \phi_E(E)dE} \quad (B4)$$

where $\phi_E(E)$ represents the spectral fluence of the beam as a function of the energy, $\bar{\varepsilon}_s(E)$ and $\sigma_{\varepsilon_s}^2(E)$ are the average and variance of $\varepsilon_s$ calculated for monoenergetic protons of energy E. A demonstration for equation (B4) is included in the Appendix. Similarly, averages and variances of the overall distributions of segment length s and energy imparted per electronic collision can be obtained. In equation (B3) note the double average since the obtained mean energy is the averaged value over the different energies present in the beam, which, in turn, have their own average value for the microdosimetric distribution of energy imparted. Equation (B4), on the other hand, is composed by two terms: the first term is the mean variance across the energies present in the beam, $\overline{\sigma_{\varepsilon_s}^2}$, and the second is the variance of the averages of the microdosimetric distributions of energy imparted, $\sigma 2/\varepsilon_s$.

Unrestricted LETd

Dose-averaged LET can be obtained regardless microdosimetric considerations by employing the concept of collision or electronic stopping power S or unrestricted LET, $\bar{L}_\infty$, in which the energy lost by the particle in electronic collisions is considered instead of the energy imparted in a certain region as microdosimetry does. Stopping power is a deterministic concept, which means it has no stochastic variability. Therefore, given a particle with energy E, we can note it as $$S(E) = \frac{d\varepsilon_\infty(E)}{ds} \quad (B5)$$

where $d\varepsilon_\infty(E)$ is the mean energy lost by the particle in an infinitesimal distance c/s. Note that $d\varepsilon_\infty$ here is a deterministic quantity. As the dose imparted by a particle with a given stopping power S can be considered proportional to S, the dose-averaged electronic stopping power or unrestricted dose-averaged LET can be obtained by weighting the electronic stopping power by itself so that $$\bar{L}_{\infty,D} = \frac{\int S^2(E)\phi_E(E)dE}{\int S(E)\phi_E(E)dE} \quad (B6)$$

where $\phi_E(E)$ represents again the spectral fluence.

Connection Between Restricted and Unrestricted Dose-Averaged LET

If we consider a virtual site that is infinitely large to comprise all the energy lost by the particle, then $\Delta \to \infty$, and $d\varepsilon_\infty$ in equation (B5) coincides with the microdosimetric mean energy imparted, $\bar{\varepsilon}_s \to d\varepsilon_\infty$. This situation occurs as long as secondary electrons do not travel a distance from the primary track comparable with the dimensions of the site. Equivalently, if a virtual site infinitely small is considered, then $\bar{s} \to 0$. In practice, this happens if stopping value does not appreciably change along the path of the particle within the site. Now, in the case of this double-ideally virtual site, equation (B6) can be expressed in terms of microdosimetric quantities means as $$\bar{L}_{\infty,D} = \lim_{\substack{\Delta \to \infty \\ \bar{s} \to 0}} \frac{1}{\bar{s}} \frac{\int \bar{\varepsilon}_S^2(E)\phi_E(E)dE}{\int \bar{\varepsilon}_S(E)\phi_E(E)dE} = \lim_{\substack{\Delta \to \infty \\ \bar{s} \to 0}} \frac{1}{\bar{s}} \frac{\sigma_{\varepsilon_S}^2 + \bar{\varepsilon}_S^2}{\bar{\varepsilon}_S} = \lim_{\substack{\Delta \to \infty \\ \bar{s} \to 0}} \frac{\bar{\varepsilon}_S}{\bar{s}} \left(1 + \frac{\sigma_{\varepsilon_S}^2}{\bar{\varepsilon}_S^2}\right) \quad (B7)$$

where we have used the general relation $\sigma_x^2 = \overline{x^2} - \bar{x}^2$, applied for the case $x = \bar{\varepsilon}_s$, so that we have $$\overline{\bar{\varepsilon}_S^2} = \sigma\frac{2}{\varepsilon_S} + \bar{\varepsilon}_S^2.$$

As, by definition $$\bar{L}_{\infty,D} = \lim_{\substack{\Delta \to \infty \\ \bar{s} \to 0}} \bar{L}_{\Delta,D},$$

it follows $$\bar{L}_{\Delta,D} = \frac{\bar{\varepsilon}_S}{\bar{s}}\left(1 + \frac{\sigma\frac{2}{\varepsilon_S}}{\bar{\varepsilon}_S^2}\right) \quad (B8)$$

Note that the microscopic spatially-restricted $\bar{L}_{\Delta,D}$ from equation (B8) will differ from the macroscopic unrestricted $\bar{L}_{\infty,D}$ in equation (B7) as much as the real microdosimetric site considered deviates from the doubly ideal situation represented by the twofold limit in equation (B7). The expression in equation (B8) according to the equations (B3) and (B4), can comprise two microdosimetric energy-dependent functions: the average energy imparted per event $\bar{\varepsilon}_s(E)$ and the average segment length $\bar{s}(E)$, instead of the six functions necessary to compute $\bar{L}_{\Delta,D}$ through equation (B2).

Note that, according to y definition in equation (B1), the expression for $\bar{y}_D \equiv \bar{y}_F(1+\sigma_y^2/\bar{y}_F^2)$ is quite similar to equation (B8):

$$\bar{y}_D \equiv \frac{\overline{\varepsilon_S}}{\bar{s}}\left(1+\frac{\sigma_{\varepsilon_S,\phi}^2}{\overline{\varepsilon_S}^2}\right) = \frac{\overline{\varepsilon_S}}{\bar{s}}\left(\frac{\overline{\sigma_{\varepsilon_S}^2}+\sigma^2_{\overline{\varepsilon_S}}}{\overline{\varepsilon_S}^2}\right) \quad (B9)$$

where the second equality is obtained directly from equation (B4) and segment length is now double-averaged to take into account the most general case, in which it can depend on the particle energy: $\bar{s}=\int \bar{s}(E)\phi_E \, dE$. However, this can be approximated by simply $\bar{s}$ as long as the fraction of particles with range shorter than the site dimension is negligible, which turns out to be most of the cases for typical energies and site dimensions in proton radiotherapy. Under this assumption, an expression for $\delta_2$ can be obtained from equations (B2), (B8) and (B9) as $$\delta_2 = \frac{\overline{\sigma_{\varepsilon_S}^2}}{\overline{\varepsilon_S}} - \frac{\sigma_{\bar{s}}^2}{\bar{s}^2}\left(\bar{\varepsilon}_S + \frac{\sigma^2_{\overline{\varepsilon_S}}}{\overline{\varepsilon_S}}\right) \quad (B10)$$

As seen in equation (B8) a third microdosimetric energy-dependent function can be incorporated to consider the spread of the energy imparted around its mean value: the variance of the energy imparted per event $\sigma_\varepsilon^2(E)$ or, equivalently, its squared root.

Revision of the Microdosimetric Functions to be Modeled

In Bertolet et al., 2019a[29] we presented analytical models to recreate the microdosimetric quantities correspondent to different monoenergetic proton beams. The microdosimetric patterns of energy deposition were obtained by using MC simulations, done with Geant4-DNA, of monoenergetic proton beams up to 100 MeV penetrating into spherical sites of 1 μm, 5 μm and 10 μm in-diameter. From these results, a series of analytical functions of the beam energy were derived. Namely, analytical forms for those site dimensions were obtained for the quantities $\bar{\varepsilon}_s(E)$, $\sigma_{\varepsilon_s}(E)$, $\bar{s}(E)$, $\bar{s}_D(E)$, $\delta_1(E)$ and $\sigma_\delta(E)$, where the two latter are the average and standard deviation of the distribution of energy imparted per collision, respectively. Note that, as shown in that work, $\delta_2 = \delta_1(1+\sigma_\delta^2/\delta_1^2)$ and, therefore, from the six previous functions, it is possible to calculate $\overline{L}_{\Delta,D}$ according to equation (B2).

Now, according to equation (B8), three functions modelled in that work are not necessary anymore: $\bar{s}_D(E)$, $\delta_1(E)$ and $\sigma_\delta(E)$, being the latter two the average and standard deviation of the distribution of energy imparted per collision, respectively. This is especially convenient since that distribution can be obtained from monoenergetic independent simulations[32]. In this work, we show that equation (B8) is equivalent to equation (B2) to obtain restricted LETd from microdosimetry in a more efficient and compact way.

Furthermore, we calculate three-dimensional distributions of $\bar{y}_D$ according to equation (B9). The interest on $\bar{y}_D$ is twofold: first, $\bar{y}_D$ is a measurable quantity as long as a microdosimeter capable to store energy deposition distributions is available, while $\overline{L}_{\Delta,D}$ is not. This can be understood just looking at the difference between equations (B8) and (B9): $\sigma_{\varepsilon_s}^2$ is the actual variance of the measured distribution whereas $\sigma 2/\varepsilon_s$ is the variance of the mean energies imparted if the problem is decomposed in its spectral components, which can be based on the knowledge of the specific energetic spectrum measured by the microdosimeter. Second, as it has been pointed out[31], $\bar{y}_D$ can be a more representative quantity to characterize the energy imparted and eventual biological damage in patients than $\overline{L}_{\Delta,D}$, which, indeed, disregards the volumetric pattern of deposition of energy reducing the problem to a unidimensional one. Nevertheless, as multiple models for biological effect are based on LETd, we keep calculating this quantity in its two versions, unrestricted and restricted; their differences between each other and with respect to $\bar{y}_D$ are here explored.

MicroCalc: An Analytical Algorithm Based on Spectral Fluence Models

In order to obtain the integrations over the spectrum given in equations (B3), (B4) and (B6), we have developed an analytical algorithm to reproduce the spectra at the voxel level in proton particle therapy. This algorithm has been presented in previous articles[30,33], in which calculations of unrestricted LETd as well as dose are shown and benchmarked against Monte Carlo computations, and can be briefly summarized as follows:

Transport of monoenergetic proton beams with energies in the clinical range (50-250 MeV) in water was calculated by means of MC simulations. Different types of particles are separated depending on their spectra: primary protons, secondary protons and other secondary particles. The dependency of the fluence of each one both on depth and laterally was modeled using analytical functions. At the same time, spectra for each one is assumed to be Gaussian and the mean and the standard deviation of these Gaussian spectra are, respectively, analytically modeled as functions of the depth and the lateral distance to the beam axis. The combination of these two models yields the spectral fluence for each species. Then, the integration given in equation (B6) can be performed for each one of the species. The average LET is obtained as the fluence-weighted average of these results. More details can be obtained elsewhere[30].

Here, we reproduce the unrestricted LETd calculation done in Bertolet et al., 2019b[30]. The above algorithm is now used to obtain $\phi_E(E)$ at each position to perform the integrations in equations (B3) and (B4) to eventually calculate restricted LETd and $\bar{y}_D$ for spherical sites of 1 μm and 10 μm using the microdosimetric functions developed in Bertolet et al., 2019a[29]. These functions are valid up to a beam energy of 100 MeV, being extrapolated beyond this point. The algorithm is already deployed as a script in the treatment planning system (TPS) Eclipse v 15.6 of Varian Medical Systems, which allows for calculations in clinical cases. This script is used to produce results for: (i) $\overline{L}_{\Delta,D}$ according to equation (B2) and to equation (B8); (ii) $\overline{L}_{\infty,D}$ according to equation (B6); and (iii) $\bar{y}_D$ according to equation (B9).

To assess the equivalency between equations (B2) and (B8), a simple case is evaluated: a pristine Bragg peak for a beam with nominal energy equal to 100 MeV produced with the Ion Beam Applications (IBA) Pencil Beam Scanning (PBS) system installed in Roberts Proton Center at the Hospital of the University of Pennsylvania. This energy is selected to disregard possible discrepancies coming from the extrapolation of the microdosimetric functions for beam energies beyond 100 MeV.

On the other hand, a prostate cancer clinical case is considered to illustrate and analyze the different distributions of unrestricted LETd, restricted LETd and $\bar{y}_D$. The calculated plan can comprise two lateral beams optimized individually to produce a uniform dose distribution over the target, with a prescription dose of 70.2 Gy in 39 fractions. Although MicroCalc considers non-homogeneities in the fluence model, results for $\overline{L}_{\Delta,D}$, $\overline{L}_{\infty,D}$ and $\bar{y}_D$ are referred to water. Additionally, results shown here only encompass primary and secondary protons.

Results

Figure 12:
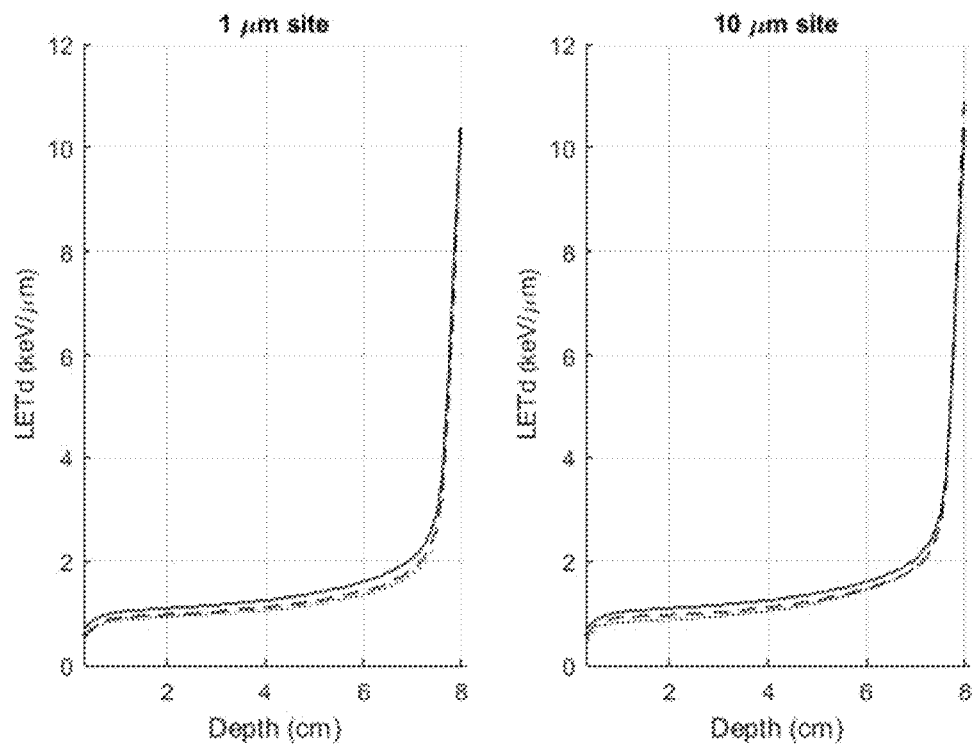
FIG. 12 shows profiles at the central axis for unrestricted LETd and restricted LETd calculations using the MicroCalc algorithm and considering only primary and secondary protons.

FIG. 12 shows the profiles for LETd at the central axis for a beam of 100 MeV as nominal energy as well as for a SOBP beam with range 20 cm and 10 cm of modulation. Three different calculations are presented: unrestricted LETd or $\overline{L}_{\infty,D}$ according to equation (B6) and restricted $\overline{L}_{\Delta,D}$ for two different microdosimetric sites, both spherical and with diameter of 1 μm and respectively. Results corresponding to equations (B2) and (B8) are compared to assess the equivalency of the methods. The mean difference along the profiles taking samples stepped by 1 mm, between these two curves, are 0.05±0.04 keV/μm for the 1-μm case and 0.05±0.02 keV/μm for the 10-μm case, respectively, where the uncertainties correspond to the standard deviation of the difference samples.

FIG. 12 shows profiles at the central axis for unrestricted LETd and restricted LETd calculations using the MicroCalc algorithm and considering only primary and secondary protons, using equations (B6) for unrestricted LETd, and (B2) and (B8) for restricted LETd, respectively for a beam with nominal energy equal to 100 MeV. Left panel is obtained using the microdosimetric models for spherical sites of 1 μm in diameter meanwhile right panel shows the same results for spherical sites of 10 μm in diameter. Legends: $\overline{L}_{\infty,D}$ from equation (B6) (solid line); $\overline{L}_{\Delta,D}$ from equation (B2) (dotted line); $\overline{L}_{\Delta,D}$ from equation (B8) (dashed line).

Figure 13:
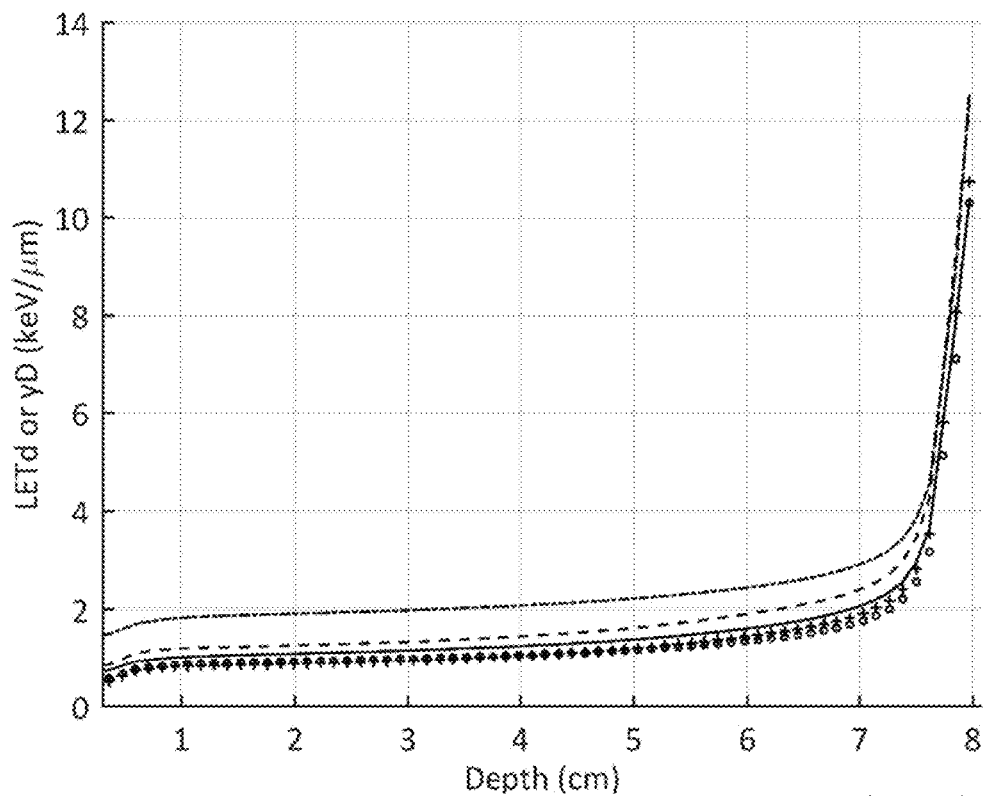
FIG. 13 shows profiles at the central axis for unrestricted LETd, restricted LETd and dose-mean lineal energy for two different microdosimetric sites.

Differences between $\overline{y}_D$ and both versions of LETd are illustrated in FIG. 13 for the same 100-MeV proton beam. While $\overline{L}_{\Delta,D}$ remains almost independent of the site dimension, $\overline{y}_D$ is clearly higher for the 1 μm case than for the 10 μm case.

FIG. 13 shows profiles at the central axis for unrestricted LETd, restricted LETd and dose-mean lineal energy for two different microdosimetric sites, spheres with diameters of 1 μm and 10 μm, for a 100-MeV beam considering only primary protons and secondary protons. Unrestricted LETd, restricted LETd and $\overline{y}_D$ are calculated according to equation (B6), (B8) and (B9), respectively. Legends: $\overline{L}_{\infty,D}$ (solid line); $\overline{L}_{\Delta,D}$ –1-μm site (dotted line); $\overline{L}_{\Delta,D}$ –10-μm site (lines with plus signs); $\overline{y}_D$-1-μm site (dotted and dashed line); $\overline{y}_D$-10-μm site (dashed line).

An axial plane at the middle of the prostate is selected to show the computed distributions. Dose and unrestricted LETd are the same for the two considered sites, meanwhile restricted LETd and $\overline{y}_D$ distributions are different depending on the site dimension selected. FIG. 14 shows the projection of the mentioned distributions upon the chosen axial plane.

Figure 14A:
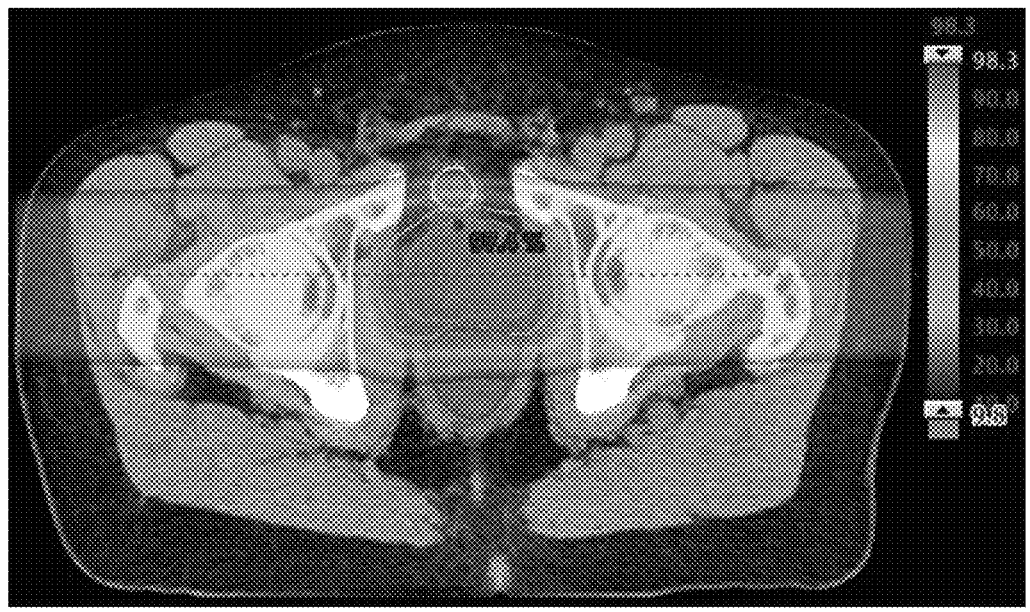
FIG. 14A shows projections of the calculated distributions with the MicroCalc algorithm as a script in Eclipse for dose on an axial plane for a prostate cancer clinical case with two lateral beams.
Figure 14B:
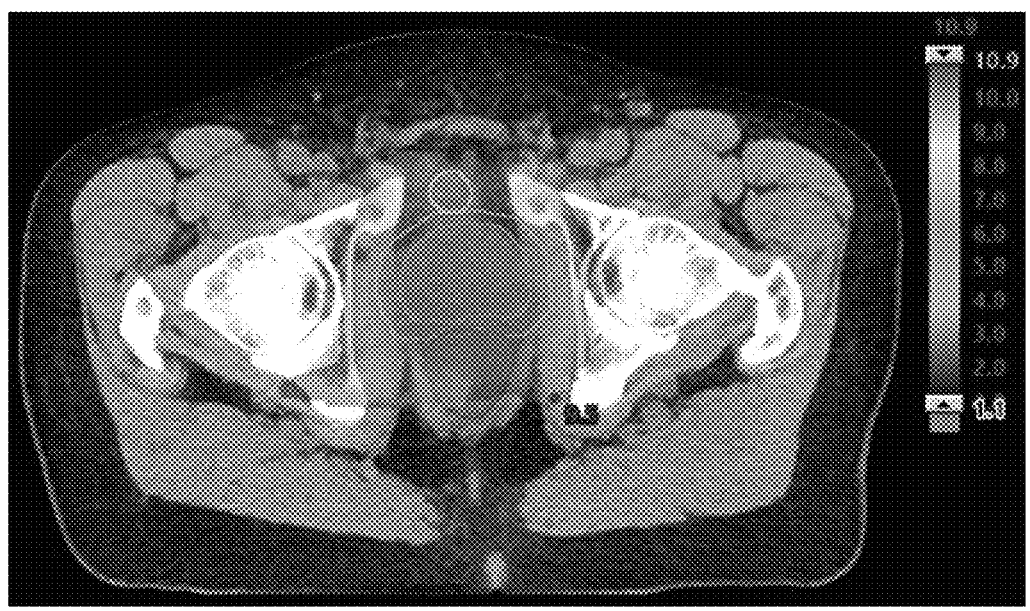
FIG. 14B shows projections of the calculated distributions with the MicroCalc algorithm as a script in Eclipse for $\bar{L}_{\infty,D}$ on an axial plane for a prostate cancer clinical case with two lateral beams.
Figure 14C:
FIG. 14C shows projections of the calculated distributions with the MicroCalc algorithm as a script in Eclipse for $\bar{L}_{\Delta,D}$-1-μm site on an axial plane for a prostate cancer clinical case with two lateral beams.
Figure 14D:
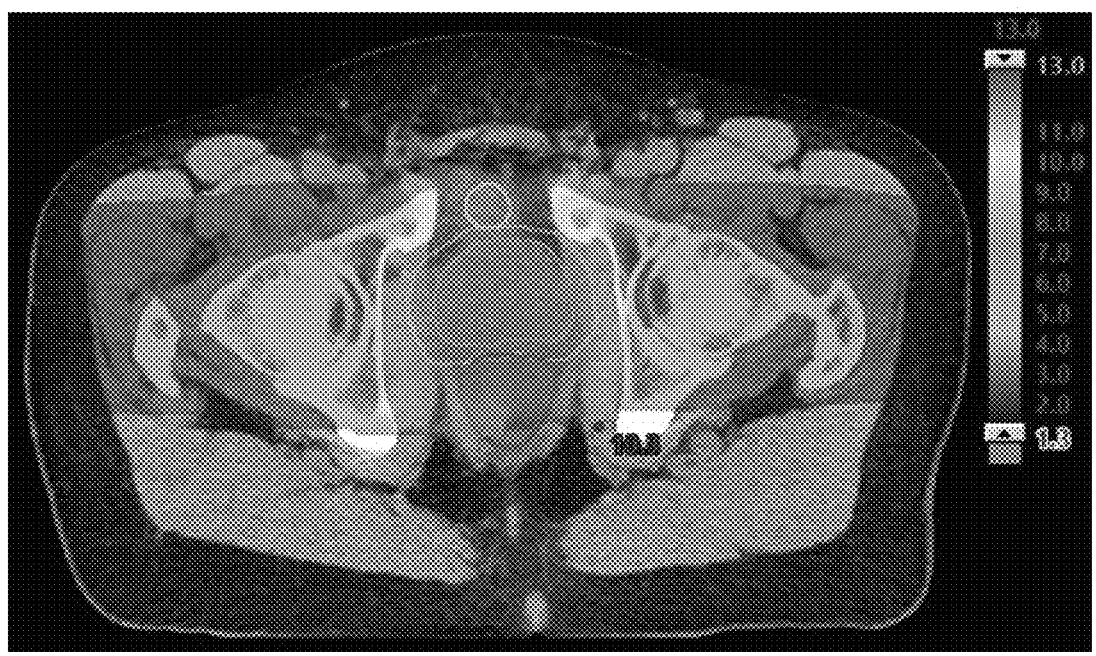
FIG. 14D shows projections of the calculated distributions with the MicroCalc algorithm as a script in Eclipse for $\bar{y}_D$-1-μm site on an axial plane for a prostate cancer clinical case with two lateral beams.
Figure 14E:
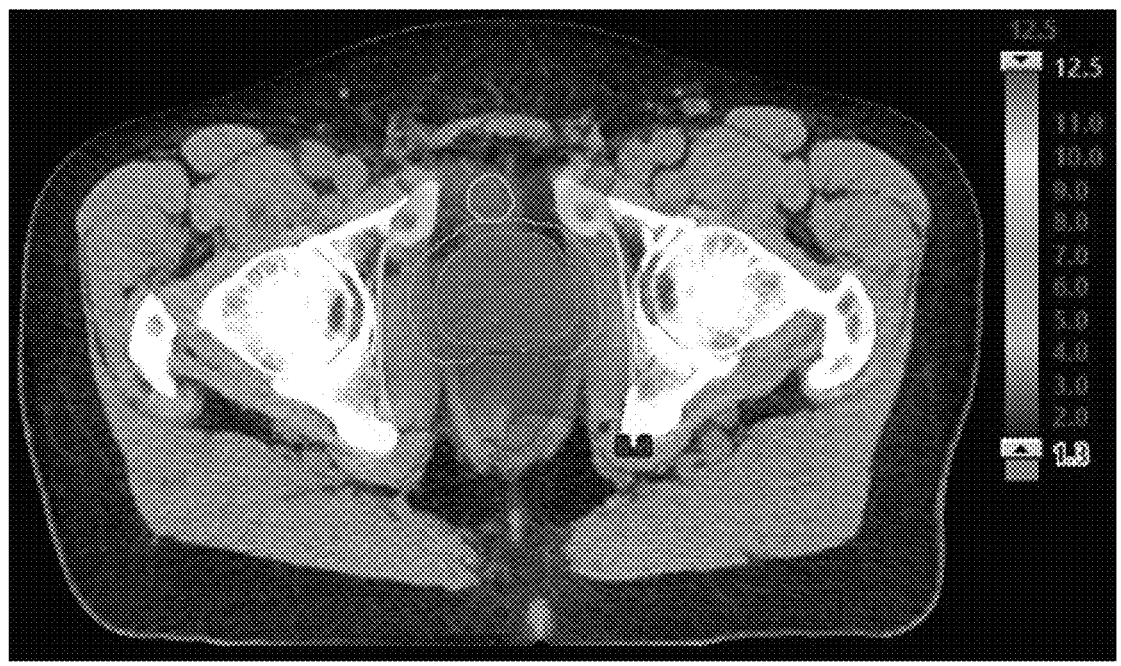
FIG. 14E shows projections of the calculated distributions with the MicroCalc algorithm as a script in Eclipse for $\bar{L}_{\Delta,D}$-10-μm site on an axial plane for a prostate cancer clinical case with two lateral beams.
Figure 14F:
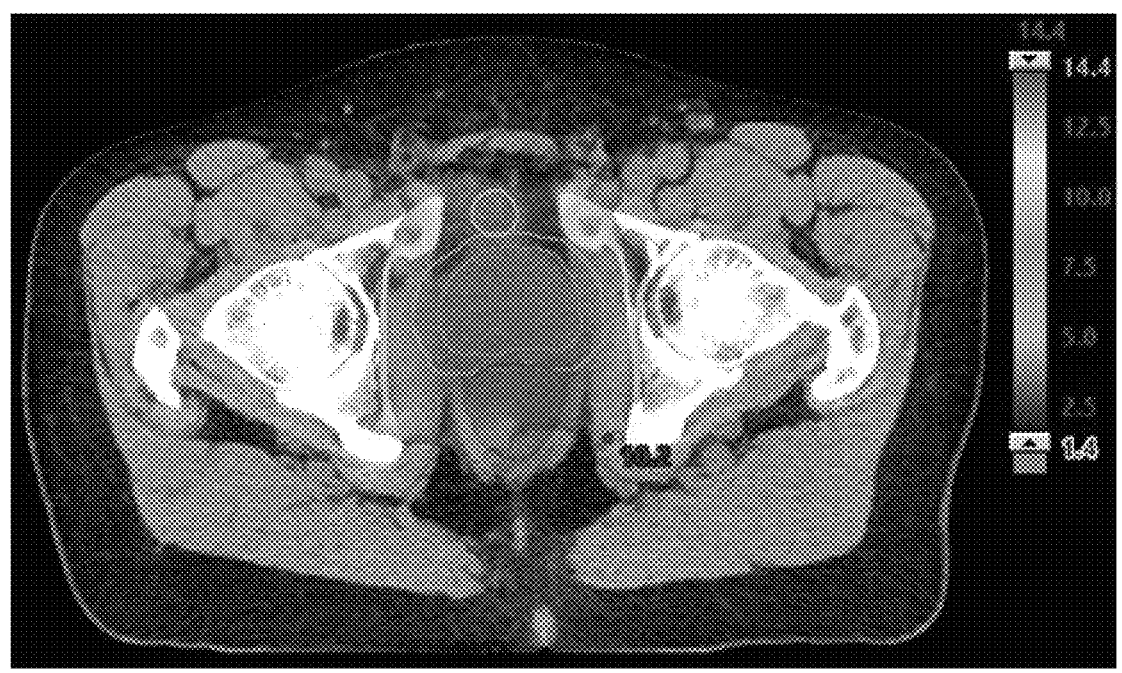
FIG. 14F shows projections of the calculated distributions with the MicroCalc algorithm as a script in Eclipse for $\bar{y}_D$-10-μm site on an axial plane for a prostate cancer clinical case with two lateral beams.

FIG. 14A shows projections of the calculated distributions with the MicroCalc algorithm as a script in Eclipse for dose on an axial plane for a prostate cancer clinical case with two lateral beams. FIG. 14B shows projections of the calculated distributions with the MicroCalc algorithm as a script in Eclipse for $\overline{L}_{\infty,D}$ on an axial plane for a prostate cancer clinical case with two lateral beams. FIG. 14C shows projections of the calculated distributions with the MicroCalc algorithm as a script in Eclipse for $\overline{L}_{\Delta,D}$ –1-μm site on an axial plane for a prostate cancer clinical case with two lateral beams. FIG. 14D shows projections of the calculated distributions with the MicroCalc algorithm as a script in Eclipse for $\overline{y}_D$-1-μm site on an axial plane for a prostate cancer clinical case with two lateral beams. FIG. 14E shows projections of the calculated distributions with the MicroCalc algorithm as a script in Eclipse for $\overline{L}_{\Delta,D}$ –10-μm site on an axial plane for a prostate cancer clinical case with two lateral beams. FIG. 14F shows projections of the calculated distributions with the MicroCalc algorithm as a script in Eclipse for $\overline{y}_D$-10-μm site on an axial plane for a prostate cancer clinical case with two lateral beams.

$\overline{L}_{\Delta,D}$ distributions are calculated using equation (B8). Structures present in this plane are represented by color lines: CTV orange; PTV purple; Bladder yellow; Whole rectum brown; Rectal anterior wall pink. Color maps represent, in each case, the values given by the scale at the right of the figures. The maximum value for the plane is indicated in red in keV/μm, except for the dose distribution (a), in which case is given in percentage of dose prescription. The dashed line in the dose distribution (a) indicates the position of the lateral profiles shown in FIG. 15.

Figure 15A:
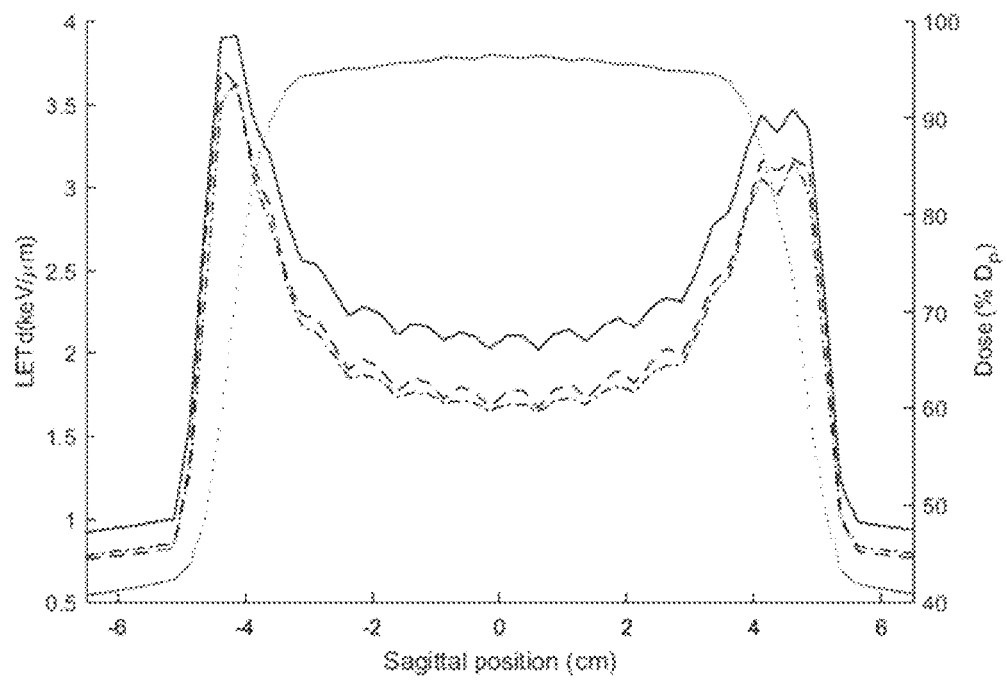
FIG. 15A shows profiles for unrestricted LETd and restricted LETd.
Figure 15B:
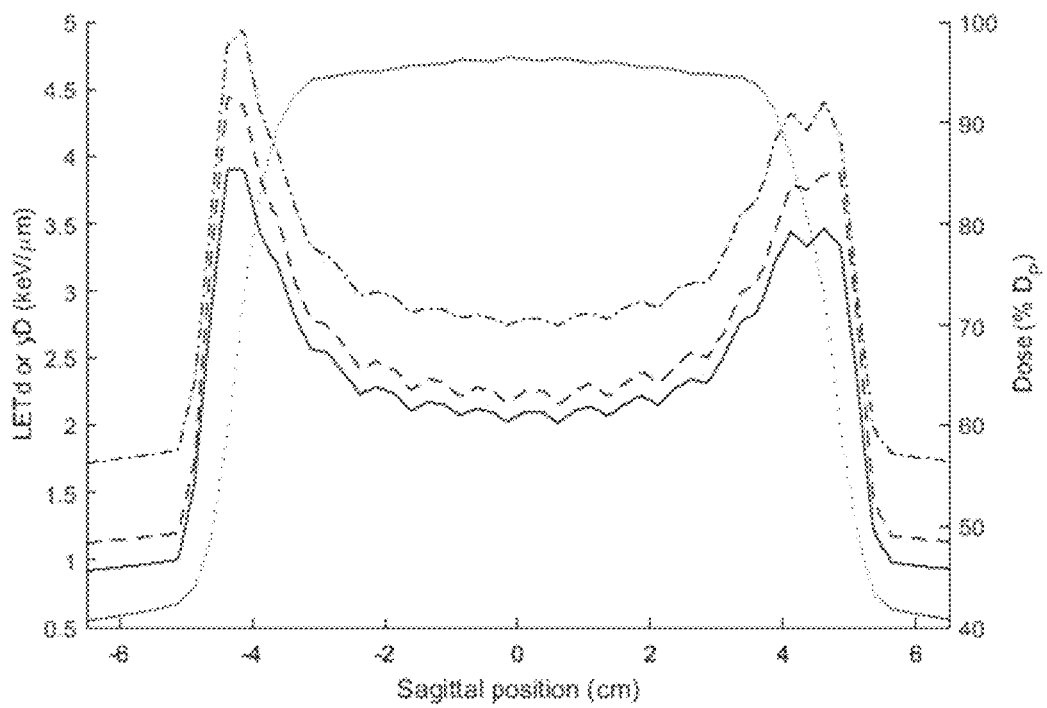
FIG. 15B shows profiles for unrestricted LETd and $\bar{y}_D$ for spherical sites of 1 μm and 10 μm in diameter.

The profiles along the dashed line marked in FIG. 14A for these quantities are shown in FIGS. 15A-B. Two types of comparisons are shown: on the one hand, restricted and unrestricted LETd are displayed in FIG. 15A. Unrestricted LETd is markedly higher along the whole profile than both restricted versions of LETd, being the 10 μm-site-restricted LETd curve slightly above the 1 μm-site-restricted LETd. On the other hand, FIG. 15(b) shows the differences between unrestricted LETd and $\overline{y}_D$. In this case, $\overline{y}_D$ for the site of 1 μm in diameter is clearly superior to $\overline{y}_D$ for the site of 10 μm. As expected according to equations (B2) and (B9), curve is above $\overline{L}_D$ curves at every point. To evaluate the relative shape of each distribution, the ratio between the peaks and the plateau, at the center of the profiles, yields the values: (a) 1.90 for $\overline{L}_{\infty,D}$; (b) 2.17 for $\overline{L}_{\Delta,D}$(1 μm); (c) 2.15 for $\overline{L}_{\Delta,D}$(10 μm); 1.78 for $\overline{y}_D$ (1 μm); and 2.01 for $\overline{y}_D$ (10 μm).

FIGS. 15A-B show sagittal profiles for the distributions in the prostate case shown in FIG. 14. FIG. 15A shows profiles for unrestricted LETd and restricted LETd. FIG. 15B shows profiles for unrestricted LETd and $\overline{y}_D$ for spherical sites of 1 μm and 10 μm in diameter. In both cases, the dose profile is also shown. Legends: FIG. 15A—Dose (dotted line); $\overline{L}_{\infty,D}$(solid line); $\overline{L}_{\Delta,D}$ –1-μm site (dotted and dashed line); $\overline{L}_{\Delta,D}$-10-μm site (dashed line); FIG. 15B—Dose (dotted line); $\overline{L}_{\infty,D}$(solid line); $\overline{y}_D$-1-μm site (dotted and dashed line); $\overline{y}_D$-10-μm site (dashed line).

Discussion

Results in FIG. 12 seem to endorse the expression for restricted LETd from microdosimetry given in equation (B8). Although both calculations share, essentially, the models for single-event average energy imparted per event e(E) and mean segment length $\overline{s}$(E), the use of equation (B2) includes the other four quantities modelled in Bertolet et al., 2019[29], i.e. standard deviation for the single-event energy imparted in the site $\sigma_\varepsilon$(E), weighted-mean segment length $\overline{s}_D$(E) and average and standard deviation for the energy imparted in the site per collision, $\delta_1$(E) and $\sigma_\delta$(E), respectively. These latter two are obtained from independent MC simulations[32], making results from equation (B2) and equation (B8) independent as well. Since our models were developed up to 100 MeV, it looks fair to restrict the comparison between these two equations until that limit. Otherwise, spurious differences due to extrapolations of the different functions would miss-represent the equivalency of the two equations.

Although results here shown only consider primary and secondary protons, disregarding the contribution from heavier nuclear fragments, our algorithm allows for further incorporation of different particle species, as shown in Bertolet et al, 2019b[30]. The process to add the contribution from any other particle p is essentially the same as for protons: (a) model the spectral fluence $\phi_E$(E; p); and (b) model the microdosimetry patterns of energy deposition, characterized by the functions $\bar{\varepsilon}_s(E; p)$, $\sigma_{\varepsilon_s}^2(E; p)$, etc. No other particles apart from protons are here considered because of simplicity. Comparative analysis between relative $\bar{y}_D$, $\bar{L}_{\infty,D}$, and $\bar{L}_{\infty,D}$ is expected to stand as valid, since other particles' contributions should affect similarly to the three quantities. However, if absolute values of any of these quantities are applied to clinical models, relevant contributions from other particles, such as alpha particles and deuterons[31], can be included in the calculation. Thus, a limitation of this work in its current version is the lack of consideration for these secondary contributions.

All results here shown are reported in terms of energy imparted to liquid water. Unrestricted LET in terms of energy imparted to other media can be obtained by using the stopping power ratio for each energy integrated along the pre-calculated beam spectrum. However, the correct calculations of restricted LET and microdosimetric quantities may require models for the functions $\bar{\varepsilon}(E)$, $\sigma_\varepsilon^2(E)$, etc. after MC simulations in those media. This represents another limitation of our method for now, although it is a potential future improvement to implement. In any case, the trends observed here are not expected to be substantially different, thus we can use similar concepts for such improvements."

Restricted LETd is logically below unrestricted LETd, although no great differences are observed between the restrictions for 1 µm and for 10 µm. Differences between restricted and unrestricted LETd tend to disappear when LET grows, i.e., near the end of the range, due to the short range of the secondary electrons around the proton track. However, when superposing beams, as in FIGS. 14 and 15, restriction on the energy has an impact on the curves for $\bar{L}_{\Delta,D}$ due to the contribution from the low LET part of each beam to the high LET part (end of the range) of the opposing beam. This effect also produces the different ratio peak-plateau in the sagittal profiles for the two opposed beams in FIG. 15 for restricted and unrestricted LETd.

An important element to the discussion of the results is related to the use of these parameters for biophysical optimization of proton plans. Whether they all equivalent or there is a more optimal configuration, it is logical to think that, if biological damage (end point) is related to the deposition of energy in a given volume, the specification of the dose quality inducing such effect should reflect the dimension of the volume, and for that reason restricted magnitudes should be better equipped to represent optimization biological damage that ultimately should represent an increase of the therapeutic window. Furthermore, when considering the difference in peak-to-plateau ratios, it seems that restricted LET provides the highest ratios, which translates into this parameter providing the highest gradients for biophysical optimization purposes. However, previous works[31] have indicated that $\bar{y}_D$ would be a more representative quantity to characterize biological effect.

Looking at equation (B9), it can be argued that while $\bar{y}_D$ includes: (a) the variability in the energy imparted in a site for a monoenergetic beam, due to straggling and chord length variability, expressed in the term $$\overline{\sigma_{\varepsilon_S}^2};$$

and (b) the variability in the energy imparted due to different beam energies, i.e. beams with different LET, given by the term $$\sigma_{\bar{\varepsilon}_S}^2.$$

On the other hand, as expectable, $\bar{L}_{\Delta,D}$ only includes the last term, associated to LET variability, according to equation (B8). Thus, $\delta_2$ can be calculated in equation (B10), obtained by comparing equations (B2), (B8) and (B9) without need for specific MC simulations, as done so far.

The extra term $$\overline{\sigma_{\varepsilon_S}^2}$$

in $\bar{y}_D$ with respect to $\bar{L}_{\Delta,D}$ justifies that the first one is larger than the second one in FIGS. 13-15. As mentioned, this term is related to the variability on the energy imparted in a site even when there is no LET variability, i.e. due to energy straggling and different chord lengths in each event. The magnitude of the difference between $\bar{y}_D$ and LETd is thus related to the relative relevancy of those two effects with respect to the variability on particles' LET itself. As LET becomes more spread near the end of the range, its relative importance against the other two effects increases so that $\bar{y}_D$ tends to approximate LETd. Additionally, $\bar{y}_D$ is considerably higher for the smaller site (1 µm) than for the 10 µm-site. This can be explained using the same reasoning: the smaller the site, the more relevant energy straggling becomes with respect to LET variability. This result can be turned around by saying $\bar{y}_D$ tends to restricted LETd as the site dimension increases, so at the macroscopic level, they both coincide.

These considerations should be taken into account when performing experimental measurements for LETd. Usual microdosimeters[34] as tissue-equivalent proportional counters (TEPC) or silicon-based diodes, collect distributions of energy imparted without the ability to discriminate the energetic spectrum so that the distinction between variance terms given in equation (B3) is not available. Therefore, they provide $\bar{y}_D$ measurements according to equation (B9) and, consequently, the expectable value for that quantity should be for considerably small devices higher than the traditionally calculated unrestricted LETd. Nonetheless, our calculation provides with actual values for $\bar{y}_D$ and $\bar{L}_{\infty,D}$ so that difference can be assessed in a straightforward way without needing the knowledge of the energy spectrum.

Finally, the calculation of RBE from the physical quantities computed here is beyond the scope of this work. However, our method is qualified to produce a number of distributions for different quantities directly related with already stablished RBE models. Indeed, not only track-related quantities as the three presented here can be computed from the microdosimetric models: weighted-average specific energy, $\bar{z}_D$ may be obtained from the $\bar{\varepsilon}(E)$ function with an expression similar to equation (B9), as well as combinations of these quantities. As there are RBE models based on $\bar{z}_D$ published in the literature[35,36], this puts forward the possibility of deployments of new models for analytical calculations of RBE in a TPS.

Conclusions

Unrestricted LETd, restricted LETd and $\bar{y}_D$ three-dimensional distributions in clinical cases are analytically computable by using a fluence-based algorithm in combination with our models for microdosimetric functions dependent on the energy. These three distributions are similar, but differences can be observed depending on the size of the microdosimetric site considered. Particularly, $\bar{y}_D$ and LETd are more different as the microdosimetric site becomes smaller. This work provides direct distributions of $\bar{y}_D$ that can be compared with experimental measurements and, at the same time, opens the possibility of using microdosimetric derived quantities—restricted LETd and $\bar{y}_D$— to drive biophysical optimization in proton therapy treatments as well as further development of RBE models for RBE based on them.

Appendix: Demonstration of Equation (B4)

According to equation (B4), the variance of the weighted sum of distributions dependent on the same variable is the mean of the variances of each individual distribution plus the variance of the means of the individual distributions around the global mean. To prove this, let's consider, for the sake of simplicity, just two distributions dependent on the variable x, $f_1(x)$ and $f_2(x)$, and a weighted sum of them:

$$F(x)=\omega_1 f_1(x)+\omega_2 f_2(x) \tag{B11}$$

with the condition $\omega_1+\omega_2=1$. The mean of the individual and the averaged distributions is, respectively:

$$\bar{x}_1 = \int x f_1(x) dx \tag{C2}$$

$$\bar{x}_2 = \int x f_2(x) dx \tag{C3}$$

and $$\bar{x}_F = \int x F(x) dx = \omega_1 \bar{x}_1 + \omega_2 \bar{x}_2 \tag{C4}$$

as shown in equation (B3). The variances of these three distributions are, respectively:

$$\sigma_1^2 = \int x^2 f_1(x) dx - \bar{x}_1^2 = \overline{x_1^2} - \bar{x}_1^2 \tag{C5}$$

$$\sigma_2^2 = \int x^2 f_2(x) dx - \bar{x}_2^2 = \overline{x_2^2} - \bar{x}_2^2 \tag{C6}$$

and $$\sigma_F^2 = \int x^2 F(x) dx - \bar{x}_F^2 = \omega_1 \overline{x_1^2} + \omega_2 \overline{x_2^2} - (\omega_1 \bar{x}_1 + \omega_2 \bar{x}_2)^2 \tag{C7}$$

Using equations (C5)-(C6), equation (C7) becomes $$\sigma_F^2 = \omega_1 \sigma_1^2 + \omega_2 \sigma_2^2 + (\omega_1 - \omega_1^2)\bar{x}_1^2 + (\omega_2 - \omega_2^2)\bar{x}_2^2 - 2\omega_1 \omega_2 \bar{x}_1 \bar{x}_2 \tag{C8}$$

On the one hand, the first two terms summed correspond to the mean of the individual variances, $\overline{\sigma_x^2} = \omega_1 \sigma_1^2 + \omega_2 \sigma_2^2$. On the other hand, the variance of the individual means around the global mean $\bar{x}_F$ is $$\sigma_{\bar{x}}^2 = \omega_1(\bar{x}_1 - \bar{x}_F)^2 + \omega_2(\bar{x}_2 - \bar{x}_F)^2 = \tag{C9}$$
$$\omega_1 \bar{x}_1^2 + \omega_2 \bar{x}_2^2 + (\omega_1 + \omega_2)\bar{x}_F^2 - 2\bar{x}_F(\omega_1 \bar{x}_1 + \omega_2 \bar{x}_2)$$

where using equation (C4) and the condition $\omega_1+\omega_2=1$, it follows $$\sigma_{\bar{x}}^2 = \omega_1 \bar{x}_1^2 + \omega_2 \bar{x}_2^2 - \bar{x}_F^2 = (\omega_1 - \omega_1^2)\bar{x}_1^2 + (\omega_2 - \omega_2^2)\bar{x}_2^2 - 2\omega_1 \omega_2 \bar{x}_1 \bar{x}_2 \tag{C10}$$

where the last equality is obtained by substituting $\bar{x}_F$ by its expression in equation (C4). This expression coincides with the last term in equation (C8), so that we can conclude $$\sigma_F^2 = \overline{\sigma_x^2} + \sigma_{\bar{x}}^2 \tag{C11}$$

result which is recursively applicable to a sum of an arbitrary number of distributions as long as the resulting distribution is normalized (e.g., where the condition $\Sigma\omega_i=1$ is required). This is done in equation (B4) by introducing the denominator $\int \phi_E(E) dE$, that ensures that the resulting distribution is normalized.

References for Example 2

1. Paganetti H, Blakely E, Carabe-Fernandez A, et al. Report of the AAPM T G-256 on the relative biological effectiveness of proton beams in radiation therapy. *Med Phys.* 2019; 46(3):e53-e78. doi:10.1002/mp.13390
2. Paganetti H. Relative biological effectiveness (RBE) values for proton beam therapy. Variations as a function of biological endpoint, dose, and linear energy transfer. *Phys Med Biol.* 2014; 59(22):R419-R472. doi:10.1088/0031-9155/59/22/R419
3. Grassberger C, Trofimov A, Lomax A, Paganetti H. Variations in linear energy transfer within clinical proton therapy fields and the potential for biological treatment planning. *Int J Radiat Oncol Blot Phys.* 2011; 80(5):1559-1566. doi:10.1016/j.ijrobp.2010.10.027
4. Peeler C R, Mirkovic D, Titt U, et al. Clinical evidence of variable proton biological effectiveness in pediatric patients treated for ependymoma. *Radiother Oncol.* 2016; 121(3):395-401. doi:10.1016/j.radonc.2016.11.001
5. Romano F, Cirrone G A P, Cuttone G, et al. A Monte Carlo study for the calculation of the average linear energy transfer (LET) distributions for a clinical proton beam line and a radiobiological carbon ion beam line. *Phys Med Biol.* 2014; 59(12):2863-2882. doi:10.1088/0031-9155/59/12/2863
6. Cortés-Giraldo M A, Carabe A. A critical study of different Monte Carlo scoring methods of dose average linear-energy-transfer maps calculated in voxelized geometries irradiated with clinical proton beams. Phys Med Biol. 2015; 60(7):2645-2669. doi:10.1088/0031-9155/60/7/2645
7. McMahon S J, Paganetti H, Prise K M. LET-weighted doses effectively reduce biological variability in proton radiotherapy planning. *Phys Med Biol.* 2018; 63:225009. doi:10.1088/1361-6560/aae8a5
8. Fager M, Toma-Dasu I, Kirk M, et al. Linear Energy Transfer Painting With Proton Therapy: A Means of Reducing Radiation Doses With Equivalent Clinical Effectiveness. *Int J Radiat Oncol.* 2015; 91(5):1057-1064. doi:10.1016/j.ijrobp.2014.12.049
9. Unkelbach J, Botas P, Giantsoudi D, Gorissen B L, Paganetti H. Reoptimization of Intensity Modulated Proton Therapy Plans Based on Linear Energy Transfer. *Int Radiat Oncol Blot Phys.* 2016; 96(5):1097-1106. doi: 10.1016/j.ijrobp.2016.08.038
10. Giantsoudi D, Grassberger C, Craft D, Niemierko A, Trofimov A, Paganetti H. Linear energy transfer-guided optimization in intensity modulated proton therapy: Feasibility study and clinical potential. *Int J Radiat Oncol Biol Phys.* 2013; 87(1):216-222. doi:10.1016/j.ijrobp.2013.05.013
11. Sánchez-Parcerisa D, López-Aguirre M, Dolcet Llerena A, Udias J M, Llerena A D, Ud M. MultiRBE: Treatment planning for protons with selective radiobiological effectiveness. *Med Phys.* 2019. doi:10.1002/mp.13718
12. Guan F, Geng C, Ma D, et al. RBE model-based biological dose optimization for proton radiobiology studies. *Int J Part Ther.* 2019; 5(1):160-171. doi:10.14338/IJPT-18-00007.1
13. Cao W, Khabazian A, Yepes P P, et al. Linear energy transfer incorporated intensity modulated proton therapy optimization. *Phys Med Biol.* 2018; 63:015013(10 pp).

Figure 16:
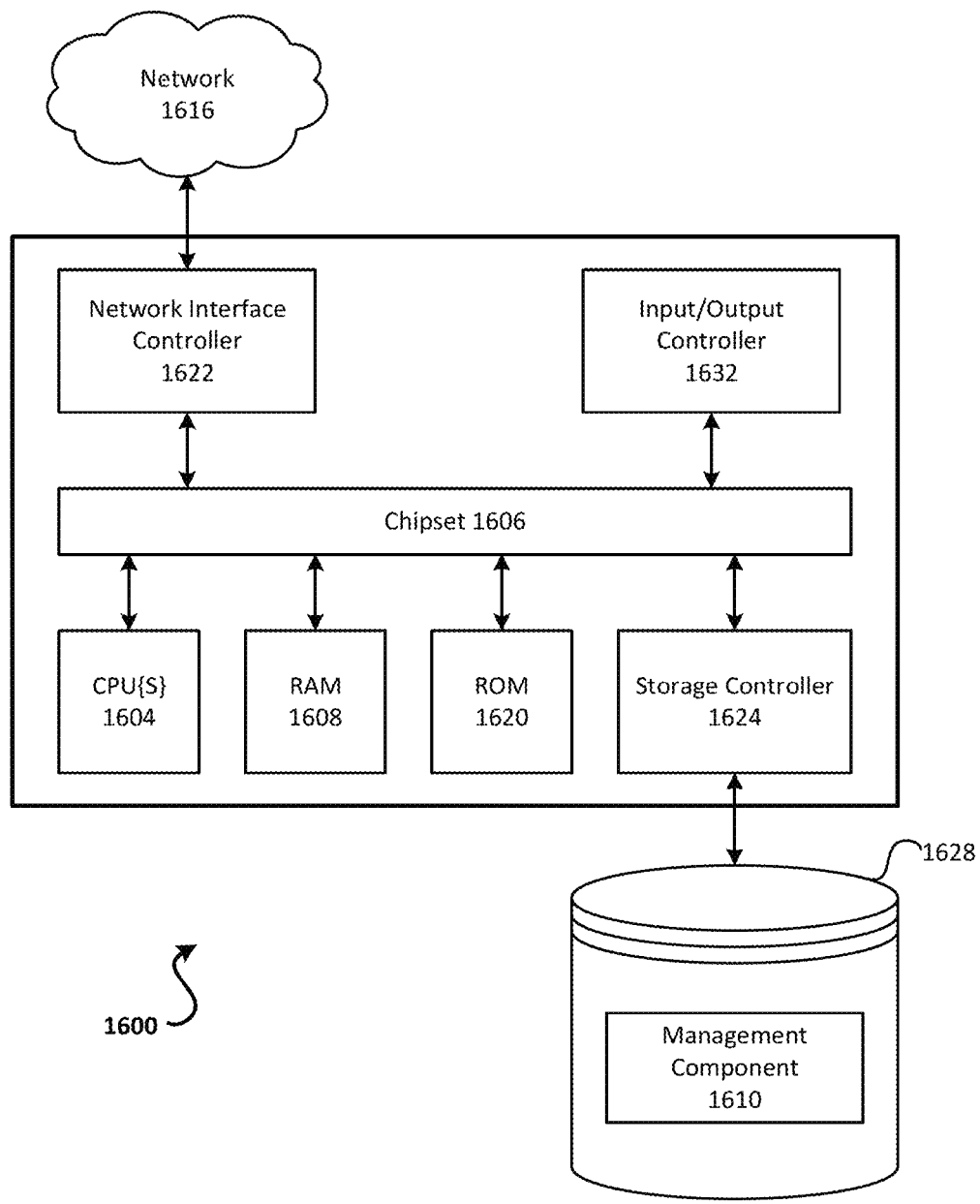
FIG. 16 is a block diagram illustrating an example computing device.

14. An Y, Shan J, Patel S H, et al. Robust intensity-modulated proton therapy to reduce high linear energy transfer in organs at risk: Med Phys. 2017; 44(12):6138-6147. doi:10.1002/mp.12610
15. Inaniwa T, Kanematsu N, Noda K, Kamada T. Treatment planning of intensity modulated composite particle therapy with dose and linear energy transfer optimization. Phys Med Biol. 2017; 62(12):5180-5197. doi:10.1088/1361-6560/aa68d7
16. Wilkens J J, Oelfke U. Analytical linear energy transfer calculations for proton therapy. Med Phys. 2003; 30(5):806-815. doi:10.1118/1.1567852
17. Wilkens J J, Oelfke U. Three-dimensional LET calculations for treatment planning of proton therapy. Z Med Phys. 2004; 14(1):41-46. doi:10.1078/0939-3889-00191
18. Marsolat F, De Marzi L, Pouzoulet F, Mazal A. Analytical linear energy transfer model including secondary particles: Calculations along the central axis of the proton pencil beam. Phys Med Biol. 2016; 61(2):740-757. doi:10.1088/0031-9155/61/2/740
19. Deng W, Ding X, Younkin J E, et al. Hybrid 3D analytical linear energy transfer calculation algorithm based on precalculated data from Monte Carlo simulations. Med Phys. 2019. doi:10.1002/mp.13934
20. ICRU. *Report 90: Key Data for Ionizing Radiation Dosimetry: Measurement Standards and Applications*. Vol 14.; 2016.
21. Kellerer A M. Fundamentals of microdosimetry. In: Kase K R, Bjarngard B E, Attix F H, eds. *The Dosimetry of Ionization Radiation. Volume I*. Academic Press, Inc.; 1985:77-162.
22. ICRU. *Report 36. Microdosimetry.*; 1983.
23. Hawkins R B. A microdosimetric-kinetic model of cell death from exposure to ionizing radiation of any LET, with experimental and clinical applications. Int J Radiat Biol. 1996; 69(6):739-755. doi:10.1080/095530096145481
24. Hawkins R B. A Microdosimetric-Kinetic Model for the Effect of Non-Poisson Distribution of Lethal Lesions on the Variation of RBE with LET. Radiat Res. 2003; 160 (1):61-69. doi:10.1667/RR3010
25. Kase Y, Kanai T, Matsufuji N, Furusawa Y, Elsässer T, Scholz M. Biophysical calculation of cell survival probabilities using amorphous track structure models for heavy-ion irradiation. Phys Med Biol. 2008; 53(1):37-59. doi:10.1088/0031-9155/53/1/003
26. Kase Y, Yamashita W, Matsufuji N, et al. Microdosimetric calculation of relative biological effectiveness for design of therapeutic proton beams. J Radiat Res. 2013; 54(3):485-493. doi:10.1093/jrr/rrs110
27. Newpower M, Patel D, Bronk L, et al. Using the Proton Energy Spectrum and Microdosimetry To Model Proton Relative Biological Effectiveness. Int J Radiat Oncol•Biol•Phys. 2019; 104(2):316-324. doi:10.1016/j.ijrobp.2019.01.094
28. Perales Á, Baratto-Roldan A, Kimstrand P, Cortés-Giraldo M A, Carabe A. Parameterising microdosimetric distributions of mono-energetic proton beams for fast estimates of yD and y*. Biomed Phys Eng Express. 2019; 5(4). doi:10.1088/2057-1976/ab236a
29. Bertolet A, Baratto-Roldán A, Cortés-Giraldo M A, et al. Segment-averaged LET concept and analytical calculation from microdosimetric quantities in proton radiation therapy. Med Phys. 2019; 46(9):4204-4214. doi:10.1002/mp.13673
30. Bertolet A, Cortés-Giraldo M A, Souris K, Carabe A. A kernel-based algorithm for the spectral fluence of clinical proton beams to calculate dose-averaged LET and other dosimetric quantities of interest. Med Phys [ACCEPTED]. 2020.
31. Grassberger C, Paganetti H. Elevated LET components in clinical proton beams. Phys Med Biol. 2011; 56(20):6677-6691. doi:10.1088/0031-9155/56/20/011
32. Bertolet A, Baratto-Roldan A, Barbieri S, Baiocco G, Carabe A, Cortés-Giraldo M A. Dose-averaged LET calculation for proton track segments using microdosimetric Monte Carlo simulations. Med Phys. 2019; 46(9):4184-4192. doi:10.1002/mp.13643
33. Bertolet A, Cortés-Giraldo M A, Souris K, et al. Calculation of clinical dose distributions in proton therapy from microdosimetry. Med Phys. 2019; 46(12):5816-5823. doi:10.1002/mp.13861
34. Lindborg L, Waker A. *Microdosimetry. Experimental Methods and Applications*. CRC Press; 2017.
35. Kase Y, Kanai T, Matsumoto Y, et al. Microdosimetric Measurements and Estimation of Human Cell Survival for Heavy-Ion Beams. Radiat Res. 2006; 166(4):629-638. doi:10.1667/RR0536.1
36. Inaniwa T, Kanematsu N, Inaniwa T. Adaptation of stochastic microdosimetric kinetic model for charged-particle therapy treatment planning. Phys Med Biol. 2018; 63(9):0-17. doi:10.1088/1361-6560/aabede Additional Aspects and Information FIG. 16 depicts a computing device that may be used in various aspects, such as implementing any of the methods, techniques, and/or the like described herein, such as determining one or more first functions, and determining quantities of interest. The computer architecture shown in FIG. 16 shows a conventional server computer, workstation, desktop computer, laptop, tablet, network appliance, PDA, e-reader, digital cellular phone, or other computing node, and may be utilized to execute any aspects of the computers described herein, such as to implement the methods described herein.

The computing device 1600 may include a baseboard, or "motherboard," which is a printed circuit board to which a multitude of components or devices may be connected by way of a system bus or other electrical communication paths. One or more central processing units (CPUs) 1604 may operate in conjunction with a chipset 1606. The CPU(s) 1604 may be standard programmable processors that perform arithmetic and logical operations necessary for the operation of the computing device 1600.

The CPU(s) 1604 may perform the necessary operations by transitioning from one discrete physical state to the next through the manipulation of switching elements that differentiate between and change these states. Switching elements may generally include electronic circuits that maintain one of two binary states, such as flip-flops, and electronic circuits that provide an output state based on the logical combination of the states of one or more other switching elements, such as logic gates. These basic switching elements may be combined to create more complex logic circuits including registers, adders-subtractors, arithmetic logic units, floating-point units, and the like.

The CPU(s) 1604 may be augmented with or replaced by other processing units, such as GPU(s) 1605. The GPU(s) 1605 may comprise processing units specialized for but not necessarily limited to highly parallel computations, such as graphics and other visualization-related processing.

A chipset 1606 may provide an interface between the CPU(s) 1604 and the remainder of the components and devices on the baseboard. The chipset 1606 may provide an interface to a random access memory (RAM) 1608 used as the main memory in the computing device 1600. The chipset 1606 may further provide an interface to a computer-readable storage medium, such as a read-only memory (ROM) 1620 or non-volatile RAM (NVRAM) (not shown), for storing basic routines that may help to start up the computing device 1600 and to transfer information between the various components and devices. ROM 1620 or NVRAM may also store other software components necessary for the operation of the computing device 1600 in accordance with the aspects described herein.

The computing device 1600 may operate in a networked environment using logical connections to remote computing nodes and computer systems through local area network (LAN) 1616. The chipset 1606 may include functionality for providing network connectivity through a network interface controller (NIC) 1622, such as a gigabit Ethernet adapter. A NIC 1622 may be capable of connecting the computing device 1600 to other computing nodes over a network 1616. It should be appreciated that multiple NICs 1622 may be present in the computing device 1600, connecting the computing device to other types of networks and remote computer systems.

The computing device 1600 may be connected to a mass storage device 1628 that provides non-volatile storage for the computer. The mass storage device 1628 may store system programs, application programs, other program modules, and data, which have been described in greater detail herein. The mass storage device 1628 may be connected to the computing device 1600 through a storage controller 1624 connected to the chipset 1606. The mass storage device 1628 may consist of one or more physical storage units. A storage controller 1624 may interface with the physical storage units through a serial attached SCSI (SAS) interface, a serial advanced technology attachment (SATA) interface, a fiber channel (FC) interface, or other type of interface for physically connecting and transferring data between computers and physical storage units.

The computing device 1600 may store data on a mass storage device 1628 by transforming the physical state of the physical storage units to reflect the information being stored. The specific transformation of a physical state may depend on various factors and on different implementations of this description. Examples of such factors may include, but are not limited to, the technology used to implement the physical storage units and whether the mass storage device 1628 is characterized as primary or secondary storage and the like.

For example, the computing device 1600 may store information to the mass storage device 1628 by issuing instructions through a storage controller 1624 to alter the magnetic characteristics of a particular location within a magnetic disk drive unit, the reflective or refractive characteristics of a particular location in an optical storage unit, or the electrical characteristics of a particular capacitor, transistor, or other discrete component in a solid-state storage unit. Other transformations of physical media are possible without departing from the scope and spirit of the present description, with the foregoing examples provided only to facilitate this description. The computing device 1600 may further read information from the mass storage device 1628 by detecting the physical states or characteristics of one or more particular locations within the physical storage units.

In addition to the mass storage device 1628 described above, the computing device 1600 may have access to other computer-readable storage media to store and retrieve information, such as program modules, data structures, or other data. It should be appreciated by those skilled in the art that computer-readable storage media may be any available media that provides for the storage of non-transitory data and that may be accessed by the computing device 1600.

By way of example and not limitation, computer-readable storage media may include volatile and non-volatile, transitory computer-readable storage media and non-transitory computer-readable storage media, and removable and non-removable media implemented in any method or technology. Computer-readable storage media includes, but is not limited to, RAM, ROM, erasable programmable ROM ("EPROM"), electrically erasable programmable ROM ("EEPROM"), flash memory or other solid-state memory technology, compact disc ROM ("CD-ROM"), digital versatile disk ("DVD"), high definition DVD ("HD-DVD"), BLU-RAY, or other optical storage, magnetic cassettes, magnetic tape, magnetic disk storage, other magnetic storage devices, or any other medium that may be used to store the desired information in a non-transitory fashion.

A mass storage device, such as the mass storage device 1628 depicted in FIG. 16, may store an operating system utilized to control the operation of the computing device 1600. The operating system may comprise a version of the LINUX operating system. The operating system may comprise a version of the WINDOWS SERVER operating system from the MICROSOFT Corporation. According to further aspects, the operating system may comprise a version of the UNIX operating system. Various mobile phone operating systems, such as IOS and ANDROID, may also be utilized. It should be appreciated that other operating systems may also be utilized. The mass storage device 1628 may store other system or application programs and data utilized by the computing device 1600.

The mass storage device 1628 or other computer-readable storage media may also be encoded with computer-executable instructions, which, when loaded into the computing device 1600, transforms the computing device from a general-purpose computing system into a special-purpose computer capable of implementing the aspects described herein. These computer-executable instructions transform the computing device 1600 by specifying how the CPU(s) 1604 transition between states, as described above. The computing device 1600 may have access to computer-readable storage media storing computer-executable instructions, which, when executed by the computing device 1600, may perform the methods described herein.

A computing device, such as the computing device 1600 depicted in FIG. 16, may also include an input/output controller 1632 for receiving and processing input from a number of input devices, such as a keyboard, a mouse, a touchpad, a touch screen, an electronic stylus, or other type of input device. Similarly, an input/output controller 1632 may provide output to a display, such as a computer monitor, a flat-panel display, a digital projector, a printer, a plotter, or other type of output device. It will be appreciated that the computing device 1600 may not include all of the components shown in FIG. 16, may include other components that are not explicitly shown in FIG. 16, or may utilize an architecture completely different than that shown in FIG. 16.

As described herein, a computing device may be a physical computing device, such as the computing device 1600 of FIG. 16. A computing node may also include a virtual machine host process and one or more virtual machine instances. Computer-executable instructions may be executed by the physical hardware of a computing device indirectly through interpretation and/or execution of instructions stored and executed in the context of a virtual machine.

It is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Components are described that may be used to perform the described methods and systems. When combinations, subsets, interactions, groups, etc., of these components are described, it is understood that while specific references to each of the various individual and collective combinations and permutations of these may not be explicitly described, each is specifically contemplated and described herein, for all methods and systems. This applies to all aspects of this application including, but not limited to, operations in described methods. Thus, if there are a variety of additional operations that may be performed it is understood that each of these additional operations may be performed with any specific embodiment or combination of embodiments of the described methods.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described herein with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, may be implemented by computer program instructions. These computer program instructions may be loaded on a general-purpose computer, special-purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that may direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

The various features and processes described above may be used independently of one another, or may be combined in various ways. All possible combinations and sub-combinations are intended to fall within the scope of this disclosure. In addition, certain methods or process blocks may be omitted in some implementations. The methods and processes described herein are also not limited to any particular sequence, and the blocks or states relating thereto may be performed in other sequences that are appropriate. For example, described blocks or states may be performed in an order other than that specifically described, or multiple blocks or states may be combined in a single block or state. The example blocks or states may be performed in serial, in parallel, or in some other manner. Blocks or states may be added to or removed from the described example embodiments. The example systems and components described herein may be configured differently than described. For example, elements may be added to, removed from, or rearranged compared to the described example embodiments.

It will also be appreciated that various items are illustrated as being stored in memory or on storage while being used, and that these items or portions thereof may be transferred between memory and other storage devices for purposes of memory management and data integrity. Alternatively, in other embodiments, some or all of the software modules and/or systems may execute in memory on another device and communicate with the illustrated computing systems via inter-computer communication. Furthermore, in some embodiments, some or all of the systems and/or modules may be implemented or provided in other ways, such as at least partially in firmware and/or hardware, including, but not limited to, one or more application-specific integrated circuits ("ASICs"), standard integrated circuits, controllers (e.g., by executing appropriate instructions, and including microcontrollers and/or embedded controllers), field-programmable gate arrays ("FPGAs"), complex programmable logic devices ("CPLDs"), etc. Some or all of the modules, systems, and data structures may also be stored (e.g., as software instructions or structured data) on a computer-readable medium, such as a hard disk, a memory, a network, or a portable media article to be read by an appropriate device or via an appropriate connection. The systems, modules, and data structures may also be transmitted as generated data signals (e.g., as part of a carrier wave or other analog or digital propagated signal) on a variety of computer-readable transmission media, including wireless-based and wired/cable-based media, and may take a variety of forms (e.g., as part of a single or multiplexed analog signal, or as multiple discrete digital packets or frames). Such computer program products may also take other forms in other embodiments. Accordingly, the present invention may be practiced with other computer system configurations.

The present disclosure can comprise at least the following aspects:

Aspect 1. A method, comprising, consisting of, or consisting essentially of: determining one or more first functions indicative of spectral fluence associated with a particle therapy, wherein the one or more first functions can be based on a plurality of simulations of a particle beam; determining, based on the one or more first functions and a second function associated with calculating a quantity, data indicative of the quantity; and causing output of the data indicative of the quantity.

The data indicative of the quantity can be output to a display (e.g., in a treatment center), sent (e.g., via a network) to a computing device, and/or the like. The one or more first functions can comprise analytical functions (e.g., once determined, the one or more functions may no longer require data from the plurality of simulations to make calculations, such as the determining of the data indicative of the quantity).

Aspect 2. The method of Aspect 1, wherein the plurality of simulations of the particle beam can comprise a plurality of Monte Carlo simulations indicative of kinetic energy at corresponding locations for corresponding initial energy values.

Aspect 3. The method of any one of Aspects 1-2, wherein each of the plurality of simulations can indicate (e.g., or comprise) an energy of a corresponding particle at a corresponding location. The location can comprise a depth and a lateral location (e.g., a location in a plane transfer to the direction of the beam).

Aspect 4. The method of any one of Aspects 1-3, wherein the one or more first functions can be fitted to one or more distributions of energy comprised in first data indicative of the plurality of simulations. The one or more distributions of energy can be fitted by modeling the one or more distributions on a probability distribution, such as a gaussian distribution, normal distribution, linear distribution, and/or the like.

Aspect 5. The method of any one of Aspects 1-4, wherein the one or more first functions can account for variation in one or more of energy, depth, or lateral position one or more particles of the particle beam. The one or more first functions can comprise a separate function at each of a plurality of depths, lateral positions, and initial energy beam values. For example, in a plane transfer to the direction of the beam, a function can be determined at each of a plurality of locations in the plane. The process can be repeated at different depths and/or for different initial energy levels. The one or more first functions can be comprised in and/or represented by a kernel (e.g., or kernel function). One or more of the one or more first functions can be functions determined by fitting a distribution (e.g., gaussian, or other distribution) to a plurality of data points generated by the simulations.

Aspect 6. The method of any one of Aspects 1-5, wherein the one or more first functions can comprise a kernel function indicative of spectral fluence density.

Aspect 7. The method of Aspect 6, wherein determining, based on the one or more first functions, the data indicative of the quantity can comprise convolving (e.g., or otherwise applying, combining) the kernel function indicative of spectral fluence density and the second function.

Aspect 8. The method of any one of Aspects 1-7, wherein the data indicative of the quantity can comprise one or more of stopping power for the particle therapy, a microdosimetric quantity, a dose, a microdosimetric-based restricted dose-averaged linear energy transfer, data indicative of a quenching effect in radiochromic films, or a combination thereof.

Aspect 9. The method of any one of Aspects 1-8, wherein determining the data indicative of the quantity can comprise calculating, at least partially simultaneously, a plurality of quantities based on corresponding second functions associated with quantities of the plurality of quantities.

Aspect 10. The method of any one of Aspects 1-9, further comprising generating first data indicative of the plurality of simulations of the particle beam, wherein determining the one or more first functions can comprise determining the one or more first functions based on the first data.

Aspect 11. A device, comprising, consisting of, or consisting essentially of: one or more processors; and memory storing instructions that, when executed by the one or more processors, can cause the device to: determine one or more first functions indicative of spectral fluence associated with a particle therapy, wherein the one or more first functions are based on a plurality of simulations of a particle beam; determine, based on the one or more first functions and a second function associated with calculating a quantity, data indicative of the quantity; and cause output of the data indicative of the quantity.

Aspect 12. The device of Aspect 11, wherein each of the plurality of simulations can indicate an energy of a corresponding particle at a corresponding location.

Aspect 13. The device of any one of Aspects 11-12, wherein the one or more first functions can be fitted to one or more distributions of energy comprised in first data indicative of the plurality of simulations.

Aspect 14. The device of any one of Aspects 11-13, wherein the one or more first functions can comprise a kernel function indicative of spectral fluence density.

Aspect 15. The device of Aspect 14, wherein the instructions that, when executed by the one or more processors, cause the device to determine the data indicative of the quantity can comprise instructions that, when executed by the one or more processors, cause the device to convolve the kernel function indicative of spectral fluence density and the second function.

Aspect 16. A system comprising, consisting of, or consisting essentially of: a particle generator (e.g., proton beam generator) configured to generate a particle beam for a therapy; and one or more processors configured to: determine one or more first functions indicative of spectral fluence associated with a particle therapy, wherein the one or more first functions are based on a plurality of simulations of the particle beam; determine, based on the one or more first functions and a second function associated with calculating a quantity, data indicative of the quantity; and cause output of the data indicative of the quantity.

Aspect 17. The system of Aspect 16, wherein each of the plurality of simulations can indicate an energy of a corresponding particle at a corresponding location.

Aspect 18. The system of any one of Aspects 16-17, wherein the one or more first functions can be fitted to one or more distributions of energy comprised in first data indicative of the plurality of simulations.

Aspect 19. The system of any one of Aspects 16-19, wherein the one or more first functions can comprise a kernel function indicative of spectral fluence density.

Aspect 20. The system of Aspect 19, wherein the one or more processors are can be configured to determine the data indicative of the quantity by convolving the kernel function indicative of spectral fluence density and the second function.

While the methods and systems have been described in connection with preferred embodiments and specific examples, it is not intended that the scope be limited to the particular embodiments set forth, as the embodiments herein are intended in all respects to be illustrative rather than restrictive.

It will be apparent to those skilled in the art that various modifications and variations may be made without departing from the scope or spirit of the present disclosure. Other embodiments will be apparent to those skilled in the art from consideration of the specification and practices described herein. It is intended that the specification and example figures be considered as exemplary only, with a true scope and spirit being indicated by the following claims.

What is claimed is:

1. A method, comprising:
   determining, by a computing device, one or more first functions indicative of spectral fluence associated with a particle therapy, wherein the one or more first functions are based on a plurality of simulations of a particle beam;
   determining, by the computing device and based on the one or more first functions and a second function associated with calculating a quantity, data indicative of the quantity; and
   causing, by the computing device, output via a display of the data indicative of the quantity.

2. The method of claim 1, wherein the plurality of simulations of the particle beam comprises a plurality of Monte Carlo simulations indicative of kinetic energy at corresponding locations for corresponding initial energy values.

3. The method of claim 1, wherein each of the plurality of simulations indicates an energy of a corresponding particle at a corresponding location.

4. The method of claim 1, wherein the one or more first functions are fitted to one or more distributions of energy comprised in first data indicative of the plurality of simulations.

5. The method of claim 1, wherein the one or more first functions account for variation in one or more of energy, depth, or lateral position one or more particles of the particle beam.

6. The method of claim 1, wherein the one or more first functions comprise a kernel function indicative of spectral fluence density.

7. The method of claim 6, wherein determining, based on the one or more first functions, the data indicative of the quantity comprises convolving the kernel function indicative of spectral fluence density and the second function.

8. The method of claim 1, wherein the data indicative of the quantity comprises one or more of stopping power for the particle therapy, a microdosimetric quantity, a dose, a microdosimetric-based restricted dose-averaged linear energy transfer, data indicative of a quenching effect in radiochromic films, or a combination thereof.

9. The method of claim 1, wherein determining the data indicative of the quantity comprises calculating, at least partially simultaneously, a plurality of quantities based on corresponding second functions associated with quantities of the plurality of quantities.

10. The method of claim 1, further comprising generating first data indicative of the plurality of simulations of the particle beam, wherein determining the one or more first functions comprises determining the one or more first functions based on the first data.

11. A device, comprising:
   one or more processors; and
   memory storing instructions that, when executed by the one or more processors, cause the device to:
      determine one or more first functions indicative of spectral fluence associated with a particle therapy, wherein the one or more first functions are based on a plurality of simulations of a particle beam;
      determine, based on the one or more first functions and a second function associated with calculating a quantity, data indicative of the quantity; and
      cause output via a display of the data indicative of the quantity.

12. The device of claim 11, wherein each of the plurality of simulations indicates an energy of a corresponding particle at a corresponding location.

13. The device of claim 11, wherein the one or more first functions are fitted to one or more distributions of energy comprised in first data indicative of the plurality of simulations.

14. The device of claim 11, wherein the one or more first functions comprise a kernel function indicative of spectral fluence density.

15. The device of claim 14, wherein the instructions that, when executed by the one or more processors, cause the device to determine the data indicative of the quantity comprises instructions that, when executed by the one or more processors, cause the device to convolve the kernel function indicative of spectral fluence density and the second function.

16. A system comprising:
   a particle generator configured to generate a particle beam for a therapy; and
   one or more processors configured to:
      determine one or more first functions indicative of spectral fluence associated with a particle therapy, wherein the one or more first functions are based on a plurality of simulations of the particle beam;
      determine, based on the one or more first functions and a second function associated with calculating a quantity, data indicative of the quantity; and
      cause output via a display of the data indicative of the quantity.

17. The system of claim 16, wherein each of the plurality of simulations indicates an energy of a corresponding particle at a corresponding location.

18. The system of claim 16, wherein the one or more first functions are fitted to one or more distributions of energy comprised in first data indicative of the plurality of simulations.

19. The system of claim 16, wherein the one or more first functions comprise a kernel function indicative of spectral fluence density.

20. The system of claim 19, wherein the one or more processors are configured to determine the data indicative of the quantity by convolving the kernel function indicative of spectral fluence density and the second function.

* * * * *

UNITED STATES PATENT AND TRADEMARK OFFICE
CERTIFICATE OF CORRECTION

PATENT NO. : 11,701,526 B2
APPLICATION NO. : 16/818683
DATED : July 18, 2023
INVENTOR(S) : Alejandro Carabe-Fernandez et al.

It is certified that error appears in the above-identified patent and that said Letters Patent is hereby corrected as shown below:

In the Specification

Under Column No. 2, Line no. 48, Replace:
"11.5 CM."
With:
--11.5 cm.--

Under Column No. 2, Line no. 54, Replace:
"11.5 CM."
With:
--11.5 cm.--

Under Column No. 3, Line no. 42, Replace:
"$\overline{L}_{A,D}-1-\mu m$"
With:
--$\overline{L}_{\Delta,D}-1-\mu m$--

Under Column No. 3, Line no. 50, Replace:
"$\overline{L}_{A,D}-10-\mu m$"
With:
--$\overline{L}_{\Delta,D}-10-\mu m$--

Under Column No. 5, Line no. 29, Replace:
"p is the physical density"
With:
--$\rho$ is the physical density--

Signed and Sealed this
Ninth Day of September, 2025

Coke Morgan Stewart
*Acting Director of the United States Patent and Trademark Office*

Under Column No. 7, Line no. 58, Replace:
"$\Phi_{int,Py}(z)$ and"
With:
--$\Phi_{int,P}(z)$ and--

Under Column No. 7, Line no. 64, Replace:
"Geant4 v 10.5.0"
With:
--Geant4 v10.5.0--

Under Column No. 9, Line no. 38, Replace:
"$a_{1,PPp}(E_0)z+$"
With:
--$a_{1,PP}(E_0)z+$--

Under Column No. 10, Line no. 52, Replace:
"kernel $K_{w,P}(\rho; z)$"
With:
--kernel $K_w(\rho; z)$--

Under Column No. 12, Line no. 25, Replace:
"lateral a for"
With:
--lateral σ for--

Under Column No. 16, Line no. 7, Replace:
"Ahnesjo A,"
With:
--Ahnesjö A,--

Under Column No. 16, Line no. 60, Replace:
"doi:10.1016/50168-"
With:
--doi:10.1016/S0168- --

Under Column No. 22, Line no. 43, Replace:
"v 15.6(Varian Medical"
With:
--v15.6 (Varian Medical--

Under Column No. 22, Line no. 56, Replace:
"provided by Eclipse; and"
With:
--provided by Eclipse™; and--

CERTIFICATE OF CORRECTION (continued)
U.S. Pat. No. 11,701,526 B2

Under Column No. 23, Line no. 46, Replace:
"comparison MCsquareMicroCalc"
With:
--comparison MCsquare-MicroCalc--

Under Column No. 26, Line no. 43, Replace:
"Phys Medial."
With:
--Phys Medica.--

Under Column No. 26, Line nos. 62-63, Replace:
"Geant4a simulation"
With:
--Geant4—a simulation--

Under Column No. 27, Line nos. 7-8, Replace:
"v 13.7. 2015."
With:
--v13.7. 2015.--

Under Column No. 27, Line no. 22, Replace:
"Phys Medial."
With:
--Phys Medica.--

Under Column No. 28, Line no. 11, Replace:
"associated uncertainty,"
With:
--associated uncertainty$^2$,--

Under Column No. 34, Line no. 46, Replace:
"v 15.6 of Varian Medical"
With:
--v15.6 of Varian Medical--

Under Column No. 37, Line no. 4, Replace:
"$\bar{y}_D$, $\bar{L}_{\infty,D}$, and $\bar{L}_{\infty,D}$"
With:
--$\bar{y}_D$, $\bar{L}_{\infty,D}$, and $\bar{L}_{\Delta,D}$--

Under Column No. 39, Line no. 39, Replace:
"$\omega_1 \bar{x}_1^2 + \omega_1 \bar{x}_2^2$"
With:
--$\omega_1 \bar{x}_1^2 + \omega_2 \bar{x}_2^2$--

CERTIFICATE OF CORRECTION (continued)
U.S. Pat. No. 11,701,526 B2

Under Column No. 39, Line no. 58, Replace:
"$\sigma_{\bar{x}}^2 = \omega_1 \bar{x}_1^2 + \omega_1 \bar{x}_2^2$"
With:
--$\sigma_{\bar{x}}^2 = \omega_1 \bar{x}_1^2 + \omega_2 \bar{x}_2^2$--

Under Column No. 39, Line no. 58, Replace:
"$(\omega_1 - \omega_1^2)\hat{x}_1^2 + (\omega_2 - \omega_2^2)$"
With:
--$(\omega_1 - \omega_1^2)\bar{x}_1^2 + (\omega_2 - \omega_2^2)$--

Under Column No. 39, Line no. 59, Replace:
"$2\omega_1\omega_2\bar{x}_1\bar{x}_1$"
With:
--$2\omega_1\omega_2\bar{x}_1\bar{x}_2$--

Under Column No. 39, Line nos. 48-49, Replace:
"Int Radiat"
With:
--Int J Radiat--